US011746369B2

(12) United States Patent
Moore et al.

(10) Patent No.: US 11,746,369 B2
(45) Date of Patent: Sep. 5, 2023

(54) KETOREDUCTASE POLYPEPTIDES AND POLYNUCLEOTIDES

(71) Applicant: Codexis, Inc., Redwood City, CA (US)

(72) Inventors: Jeffrey C. Moore, Westfield, NJ (US); Jack Liang, South San Francisco, CA (US); Jonathan Penfield, Truckee, CA (US); Jovana Nazor, Milpitas, CA (US); Nikki Dellas, San Carlos, CA (US); Vesna Mitchell, Santa Clara, CA (US); Da Duan, Newark, CA (US); Iman Farasat, Rahway, NJ (US); Agustina Rodriguez-Granillo, Rahway, NJ (US); Grant Murphy, Rahway, NJ (US); Nicholas Marshall, Rahway, NJ (US)

(73) Assignee: Codexis, Inc., Redwood City, CA (US)

(*) Notice: Subject to any disclaimer, the term of this patent is extended or adjusted under 35 U.S.C. 154(b) by 36 days.

(21) Appl. No.: 17/239,953

(22) Filed: Apr. 26, 2021

(65) Prior Publication Data

US 2021/0254119 A1    Aug. 19, 2021

Related U.S. Application Data

(62) Division of application No. 16/605,576, filed as application No. PCT/US2018/027450 on Apr. 13, 2018, now Pat. No. 11,021,729.

(60) Provisional application No. 62/491,161, filed on Apr. 27, 2017.

(51) Int. Cl.
| | |
|---|---|
| *C12P 41/00* | (2006.01) |
| *C12N 9/02* | (2006.01) |
| *C12N 9/04* | (2006.01) |
| *C12N 15/70* | (2006.01) |

(52) U.S. Cl.
CPC .......... *C12P 41/002* (2013.01); *C12N 9/0004* (2013.01); *C12N 9/0006* (2013.01); *C12N 15/70* (2013.01); *C12Y 101/01002* (2013.01); *C12Y 120/01001* (2013.01)

(58) Field of Classification Search
CPC ......... C12P 41/002; C12P 7/02; C12P 17/182; C12N 9/0004; C12N 9/0006; C12N 15/70; C12Y 101/01002; C12Y 120/01001; C12Y 101/01184
See application file for complete search history.

(56) References Cited

U.S. PATENT DOCUMENTS

| | | |
|---|---|---|
| 5,559,030 A | 9/1996 | Matsuyama et al. |
| 5,605,793 A | 2/1997 | Stemmer |
| 5,700,670 A | 12/1997 | Yamagishi et al. |
| 5,763,236 A | 9/1998 | Kojima et al. |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,891,685 A | 4/1999 | Yamagishi et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,265,201 B1 | 7/2001 | Wackett et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,337,186 B1 | 1/2002 | Krebber |
| 6,344,356 B1 | 2/2002 | Stemmer |

(Continued)

FOREIGN PATENT DOCUMENTS

| | | |
|---|---|---|
| CN | 105420306 A | 3/2016 |
| JP | 07-231785 A | 9/1995 |

(Continued)

OTHER PUBLICATIONS

UniProtKT/TREMBL Accession No. H8WVM2_CAN09 dated May 16, 2012.
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).

(Continued)

*Primary Examiner* — Ganapathirama Raghu
(74) *Attorney, Agent, or Firm* — Codexis, Inc.

(57) ABSTRACT

The present invention provides engineered ketoreductase and phosphite dehydrogenase enzymes having improved properties as compared to a naturally occurring wild-type ketoreductase and phosphite dehydrogenase enzymes, as well as polynucleotides encoding the engineered ketoreductase and phosphite dehydrogenase enzymes, host cells capable of expressing the engineered ketoreductase and phosphite dehydrogenase enzymes, and methods of using the engineered ketoreductase and phosphite dehydrogenase enzymes to synthesize a chiral catalyst used in the synthesis of antiviral compounds, such as nucleoside inhibitors. The present invention further provides methods of using the engineered enzymes to deracemize a chiral alcohol in a one-pot, multi-enzyme system.

6 Claims, 6 Drawing Sheets

Specification includes a Sequence Listing.

(56) References Cited

U.S. PATENT DOCUMENTS

| | | |
|---|---|---|
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,399,339 B1 | 6/2002 | Wolberg et al. |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,483,011 B1 | 11/2002 | Stemmer et al. |
| 6,484,105 B2 | 11/2002 | Zhang |
| 6,489,146 B2 | 12/2002 | Stemmer et al. |
| 6,500,617 B1 | 12/2002 | Stemmer et al. |
| 6,500,639 B2 | 12/2002 | Subramanian |
| 6,506,602 B1 | 1/2003 | Stemmer |
| 6,506,603 B1 | 1/2003 | Stemmer |
| 6,518,065 B1 | 2/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,605,430 B1 | 7/2003 | Affholter et al. |
| 6,602,986 B1 | 8/2003 | Stemmer et al. |
| 6,613,514 B2 | 9/2003 | Patten et al. |
| 6,645,746 B1 | 11/2003 | Kizaki et al. |
| 6,653,072 B1 | 11/2003 | Patten et al. |
| 6,686,515 B1 | 2/2004 | Lassner et al. |
| 6,703,240 B1 | 3/2004 | Stemmer et al. |
| 6,716,631 B1 | 4/2004 | delCardayre et al. |
| 6,800,477 B2 | 10/2004 | Patel et al. |
| 6,818,752 B2 | 11/2004 | Rozzell, Jr. et al. |
| 6,825,001 B2 | 11/2004 | Wackett et al. |
| 6,902,922 B2 | 6/2005 | Ness et al. |
| 6,917,882 B2 | 7/2005 | Selfinov et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,220,566 B2 | 5/2007 | Ness et al. |
| 7,288,375 B2 | 10/2007 | Stemmer et al. |
| 7,384,387 B1 | 6/2008 | Raillard et al. |
| 7,421,347 B2 | 9/2008 | Selfinov et al. |
| 7,430,477 B2 | 9/2008 | Selfinov et al. |
| 7,462,469 B2 | 12/2008 | Bass et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,477 B1 | 1/2011 | Gustafsson et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 7,981,614 B2 | 7/2011 | Stemmer et al. |
| 8,014,961 B2 | 9/2011 | Bass et al. |
| 8,029,988 B2 | 10/2011 | Crameri et al. |
| 8,048,674 B2 | 11/2011 | Minshull et al. |
| 8,058,001 B2 | 11/2011 | Crameri et al. |
| 8,076,138 B2 | 12/2011 | delCardayre et al. |
| 8,108,150 B2 | 1/2012 | Mundorff et al. |
| 8,170,806 B2 | 5/2012 | Selfinov et al. |
| 8,224,580 B2 | 7/2012 | Mundorff et al. |
| 8,273,547 B2 | 9/2012 | Giver et al. |
| 8,343,764 B2 | 1/2013 | Abad et al. |
| 8,377,681 B2 | 2/2013 | delCardayre et al. |
| 8,383,346 B2 | 2/2013 | Colbeck et al. |
| 8,457,903 B1 | 6/2013 | Emig et al. |
| 8,504,498 B2 | 8/2013 | Fox |
| 8,589,085 B2 | 11/2013 | Selfinov et al. |
| 8,748,143 B2 | 6/2014 | Liang et al. |
| 8,762,066 B2 | 6/2014 | Fox |
| 8,768,871 B2 | 7/2014 | Fox |
| 9,593,326 B2 | 3/2017 | Clark et al. |
| 2004/0101937 A1 | 5/2004 | Moore et al. |
| 2006/0195947 A1 | 8/2006 | Davis et al. |
| 2006/0286646 A1 | 12/2006 | Patel et al. |
| 2008/0038803 A1 | 2/2008 | Iwasaki et al. |
| 2008/0220990 A1 | 9/2008 | Fox |
| 2009/0312196 A1 | 12/2009 | Colbeck et al. |
| 2010/0151529 A1 | 6/2010 | Zhao et al. |
| 2011/0070630 A1 | 3/2011 | Gruber et al. |
| 2011/0105483 A1 | 5/2011 | Chimmanamada et al. |
| 2015/0239852 A1 | 8/2015 | Van Summeren et al. |
| 2016/0053289 A1 | 2/2016 | Ertl |

FOREIGN PATENT DOCUMENTS

| | | |
|---|---|---|
| JP | 2010-539952 A | 12/2010 |
| JP | 2011-516053 A | 5/2011 |
| JP | 2016-521121 A | 7/2016 |
| JP | 2016-537700 A | 12/2016 |
| WO | 95/22625 A1 | 8/1995 |
| WO | 95/33836 A1 | 12/1995 |
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 00/42651 A1 | 7/2000 |
| WO | 01/40450 A1 | 6/2001 |
| WO | 01/55342 A2 | 8/2001 |
| WO | 01/75767 A2 | 10/2001 |
| WO | 2004/108912 A2 | 12/2004 |
| WO | 2005/054491 A1 | 6/2005 |
| WO | 2006/074194 A2 | 7/2006 |
| WO | 2006/090814 A1 | 8/2006 |
| WO | 2008/042876 A2 | 4/2008 |
| WO | 2009/036404 A2 | 3/2009 |
| WO | 2009/152336 A1 | 12/2009 |
| WO | 2011/071058 A1 | 6/2011 |
| WO | 2015/048572 A1 | 4/2015 |

OTHER PUBLICATIONS

Beaucage, S.L., et al., "Deoxynucleoside phosphoamidites—A new class of key intermediates for deoxypolynucleotide synthesis," Tetrahedron Letters, 22(20):1859-62 (1981).

Botstein, D., et al., "Strategies and applications of in vitro mutagenesis," Science, 229(4719):1193-1201 [1985].

(56) References Cited

OTHER PUBLICATIONS

Broussy, R.W., et al., "Enantioselective, Ketoreductase-Based Entry into Pharmaceutical Building Blocks: Ethanol as Tunable Nicotinamide Reductant," Org. Lett., 11(2):305-308 [2009].
Carter, P., "Site-directed mutagenesis," Biochem. J., 237:1-7 (1986).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15 (5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Ehrlich, S.D.,"DNA cloning in Bacillus subtilis," Proc. Natl. Acad. Sci. USA, 75(3):1433-1436 [1978].
Guo, Z., et al., "3'-End-Forming Signals of Yeast mRNA," Mol. Cell. Biol., 15(11):5983-5990 [1995].
Henikoff, S., et al., "Amino acid substitution matrices from protein blocks," Proc. Natl. Acad. Sci. USA, 89:10915-10919 [1992].
Hummel, W., et al., "Dehydrogenases for the synthesis of chiral compounds," Eur. J. Biochem., 184:1-13 [1989].
Kramer, B., et al., "Different base/base mismatches are corrected with different efficiencies by the methyl-directed DNA mismatch-repair system of E. coli," Cell, 38(3):879-887 [1984].
Lathe, R., et al., "Plasmid and bacteriolphage vecotrs for excision of intact inserts," Gene, 57:193-201 [1987].
Ling, M.M., et al., "Approaches to DNA Mutagenesis: An Overview," Anal. Biochem., 254(2):157-78 [1997].
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Curr. Op. Chem. Biol., 3(3):284-290 (1999).
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Romanos, M.A., et al., "Foreign gene expression in yeast: a review," Yeast 8:423-488 [1992].
Santaniello, E., et al., "Chiral synthesis of a component of Amanita muscaria,(-)-4-hydroxypyrrolidin-2-one, and Assessment of its absolute configuration," J. Chem. Res., (S)132-133 [1984].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Villa-Komaroff, L., et al., "A bacterial clone synthesizing proinsulin," Proc. Natl Acad. Sci. USA, 75:3727-3731 (1978).
Wells, J.A., et al., "Cassette mutagenesis: an efficient method for generation of multiple mutations at defined sites," Gene, 34:315-323 (1985).
Zhang, J-H., et al., "Directed evolution of a fucosidase from a galactosidase by DNA shuffling and screening," Proc. Nat. Acad. Sci., U.S.A., 94:4504-4509 (1997).
Zhou, B., et al., "Stereochemical control of yeast reductions. 1. Asymmetric synthesis of L-Carnitine," J. Am. Chem. Soc., 105:5925-5926 [1983].
Genbank Accession No. 1NXQ_A dated Sep. 24, 2008.
Genbank Accession No. AAP94029.1 dated Apr. 1, 2004.
Genbank Accession No. AF160799 dated Dec. 9, 1999.
Genbank Accession No. BAA24528.1 dated Jan. 28, 1998.
Genbank Accession No. JC7338 dated Jun. 3, 2002.
UniProtKB/Swiss-Prot No. P14941 dated May 10, 2017.
Kita, K., et al., "Cloning, Overexpression, and Mutagenesis of the*Sporobolomyces salmonicolor* AKU4429 Gene Encoding a New Aldehyde Reductase, Which Catalyzes the Stereoselective Reduction of Ethyl 4-Chloro-3-Oxobutanoate to Ethyl (S)-4-Chloro-3-Hydroxybutanoate," Applied and Environmental Microbiology, 65(12):5207-5211 [1999].
Ma, S.K., et al., "A green-by-design biocatalytic process for atorvastatin intermediate," Green Chemistry, 12(1):81-86 [2010].
Zheng, G., et al., "New opportunities for biocatalysis: driving the synthesis of chiral chemicals," Current Opinion in Biotechnology, 22(6):784-792 [2011].
Broun, P., et al., "Catalytic Plasticity of Fatty Acid Modification Enzymes Underlying Chemical Diversity of Plant Lipids," Science, 282:1315-1317 [1998].
Devos, D., et al., "Practical Limits of Function Prediction," Proteins: Structure, Function, and Genetics, 41:98-107 [2000].
Seffernick, J.L., et al., "Melamine Deaminase and Atrazine Chlorohydrolase: 98 Percent Identical but Functionally Different," J. Bacteriology, 183(8):2405-2410 [2001].
Whisstock, J.C., et al., "Prediction of protein function from protein sequence and structure," Quarterly Reviews of Biophysics, 36(3):307-340 [2003].
Witkowski, A., et al., "Conversion of a beta-Ketoacyl Synthase to a Malonyl Decarboxylase by Replacement of the Active-Site Cysteine with Glutamine," Biochemistry, 38(36):11643-11650 [1999].

SEQUENCE LISTING

```
<160> NUMBER OF SEQ ID NOS: 260

<210> SEQ ID NO 1
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 1
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aaggtgttat catgccggtt     780
ggtctgggtg ctccgaacct gtcttttaac ctgggtgacc tggctctgcg tgaaatccgt     840
atcctgggtt ctttctgggg taccaccaac gacctggacg acgttctgaa actggttttct     900 gaaggtaaag ttaaaccggt tgtacgttct gctaaactga aagaactgcc ggaatacatc     960
gaaaaactgc gtaacaacgc ttacgaaggt cgtgttgttt caacccgta a               1011

<210> SEQ ID NO 2
<211> LENGTH: 336
<212> TYPE: PRT
<213> ORGANISM: Artificial Sequence
```

```
<220> FEATURE:
<223> OTHER INFORMATION: KRED-NADH-102 variant

<400> SEQUENCE: 2

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 3
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 3
atgtctatcc cgtcttctca gtatggtttc gtatttaaca aacagtctgg tctgaaactg      60
```

```
cgcaacgatc tgccagtaca caagccgaaa gctggtcaac tgctgctgaa agtagatgca    120
gtaggtctgt gccactctga tctgcacgtt atctacgaag cctggactg cggtgacaac    180 tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtatttttct gctaaactga agaactgcc ggaatacatc    960 gaaaaactgc gtaacaacgc ttacgaaggt cgtgttgttt caacccgta a             1011
```

<210> SEQ ID NO 4
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 4

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
        130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190
```

```
Phe Gly Ala Lys Val Thr Val Leu Asp Lys Lys Glu Ala Arg Asp
            195                 200                 205
Gln Ala Lys Lys Leu Gly Ala Asp Ala Val Tyr Glu Thr Leu Pro Glu
        210                 215                 220
Ser Ile Ser Pro Gly Ser Phe Ser Ala Cys Phe Asp Phe Val Ser Val
225                 230                 235                 240
Gln Ala Thr Phe Asp Val Cys Gln Lys Tyr Val Glu Pro Lys Gly Val
                245                 250                 255
Ile Met Pro Val Gly Leu Gly Ala Pro Asn Leu Ser Phe Asn Leu Gly
                260                 265                 270
Asp Leu Ala Leu Arg Glu Ile Arg Ile Leu Gly Ser Phe Trp Gly Thr
            275                 280                 285
Thr Asn Asp Leu Asp Asp Val Leu Lys Leu Val Ser Glu Gly Lys Val
        290                 295                 300
Lys Pro Val Val Phe Ser Ala Lys Leu Lys Glu Leu Pro Glu Tyr Ile
305                 310                 315                 320
Glu Lys Leu Arg Asn Asn Ala Tyr Glu Gly Arg Val Val Phe Asn Pro
                325                 330                 335
```

<210> SEQ ID NO 5
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 5

```
atgtctatcc cgtcttctca gtatggtttc gtatttaaca acagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactt gggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa acgctttcg gtgactggtt cggtctgggt     360
tatgatggtg gctatcaaca atacctgctg gtaactcgcc gcgtaacct gtctcgtatc      420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaactgg gtgctgacgc tgtttacgaa      660
accctgccgg aatctatctc tccgggttct ttctctgctt gcttcgactt cgtttctgtt     720
caggctacct cgacgtttg ccagaaatac gttgaaccga aggtgttat catgccggtt       780
ggtctgggtg ctccgaacct gtcttttaac ctgggtgacc tggctctgcg tgaaatccgt     840
atcctgggt ctttctgggg taccaccaac gacctggacg acgttctgaa actggtttct      900
gaaggtaaag ttaaaccggt tgtacgttct gctaaactga agaactgcc ggaatacatc      960
gaaaaactgc gtaacaacgc ttacgaaggt cgtgttgttt tcaacccgta a            1011
```

<210> SEQ ID NO 6
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 6

```
Met Ser Ile Pro Ser Ser Gln Tyr Gly Phe Val Phe Asn Lys Gln Ser
1               5                   10                  15
Gly Leu Lys Leu Arg Asn Asp Leu Pro Val His Lys Pro Lys Ala Gly
            20                  25                  30
Gln Leu Leu Lys Val Asp Ala Val Gly Leu Cys His Ser Asp Leu
        35                  40                  45
His Val Ile Tyr Glu Gly Leu Asp Leu Gly Asp Asn Tyr Val Met Gly
    50                  55                  60
His Glu Ile Ala Gly Thr Val Ala Val Gly Asp Asp Val Ile Asn
65                  70                  75                  80
Tyr Lys Val Gly Asp Arg Val Ala Cys Val Gly Pro Asn Gly Cys Gly
                85                  90                  95
Gly Cys Lys Tyr Cys Arg Gly Ala Ile Asp Asn Val Cys Lys Asn Ala
            100                 105                 110
Phe Gly Asp Trp Phe Gly Leu Gly Tyr Asp Gly Tyr Gln Gln Tyr
        115                 120                 125
Leu Leu Val Thr Arg Pro Arg Asn Leu Ser Arg Ile Pro Asp Asn Val
    130                 135                 140
Ser Ala Asp Val Ala Ala Ala Ser Thr Asp Ala Val Leu Thr Pro Tyr
145                 150                 155                 160
His Ala Ile Lys Met Ala Gln Val Ser Pro Thr Ser Asn Ile Leu Leu
                165                 170                 175
Ile Gly Ala Gly Gly Leu Gly Gly Asn Ala Ile Gln Val Ala Lys Ala
            180                 185                 190
Phe Gly Ala Lys Val Thr Val Leu Asp Lys Lys Glu Ala Arg Asp
        195                 200                 205
Gln Ala Lys Lys Leu Gly Ala Asp Ala Val Tyr Glu Thr Leu Pro Glu
    210                 215                 220
Ser Ile Ser Pro Gly Ser Phe Ser Ala Cys Phe Asp Phe Val Ser Val
225                 230                 235                 240
Gln Ala Thr Phe Asp Val Cys Gln Lys Tyr Val Glu Pro Lys Gly Val
                245                 250                 255
Ile Met Pro Val Gly Leu Gly Ala Pro Asn Leu Ser Phe Asn Leu Gly
            260                 265                 270
Asp Leu Ala Leu Arg Glu Ile Arg Ile Leu Gly Ser Phe Trp Gly Thr
        275                 280                 285
Thr Asn Asp Leu Asp Asp Val Leu Lys Leu Val Ser Glu Gly Lys Val
    290                 295                 300
Lys Pro Val Val Arg Ser Ala Lys Leu Lys Glu Leu Pro Glu Tyr Ile
305                 310                 315                 320
Glu Lys Leu Arg Asn Asn Ala Tyr Glu Gly Arg Val Val Phe Asn Pro
                325                 330                 335
```

<210> SEQ ID NO 7
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 7

```
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
```

```
gtaggtctgt gccactctga tctgcacgtt atctacgaag gcctggactg cggtgacaac      180
tacgttatgg gtcacgaaat cgctggtacc gttgctgctg ttggtgatga cgttatcaac      240
tacaaagtag gtgaccgtgt agcttgtgtt ggtccgaacg gttgcggtgg ttgcaaatac      300
tgccgtggtg ctatcgacaa cgtttgcaaa aacgctttca agactggttt cggtctgggt      360
tatgatggtg gctatcaaca atacctgctg gtaactcgcc cgcgtaacct gtctcgtatc      420
ccggataacg tatctgctga tgttgctgct gcttctaccg acgctgttct gactccgtac      480
cacgctatca aaatggctca ggtttctccg acctctaaca tcctgctgat cggtgctggt      540
ggtctgggtg gtaacgctat ccaggttgct aaagcattcg gtgctaaagt taccgttctg      600
gacaaaaaaa aagaagctcg tgaccaggct aaaaaactgg gtgctgacgc tgtttacgaa      660
accctgccgg aatctatctc tccgggttct ttctctgctt gcttcgactt cgtttctgtt      720
caggctacct tcgacgtttg ccagaaatac gttgaaccga aaggtgttat catgccggtt      780
ggtctgggtg ctccgaacct gtcttttaac ctgggtgacc tggctctgcg tgaaatccgt      840
atcctgggtt ctttctgggg taccaccaac gacctggaca cgttctgaa actgtttct       900 gaaggtaaag ttaaaccggt tgtacgttct gctaaactga agaactgcc ggaatacatc      960 gaaaaactgc gtaacaacgc ttacgaaggt cgtgttgttt tcaacccgta a             1011
```

<210> SEQ ID NO 8
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 8

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Lys Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205
```

```
                Gln Ala Lys Lys Leu Gly Ala Asp Ala Val Tyr Glu Thr Leu Pro Glu
                    210                 215                 220

Ser Ile Ser Pro Gly Ser Phe Ser Ala Cys Phe Asp Phe Val Ser Val
                225                 230                 235                 240

Gln Ala Thr Phe Asp Val Cys Gln Lys Tyr Val Glu Pro Lys Gly Val
                                245                 250                 255

Ile Met Pro Val Gly Leu Gly Ala Pro Asn Leu Ser Phe Asn Leu Gly
                            260                 265                 270

Asp Leu Ala Leu Arg Glu Ile Arg Ile Leu Gly Ser Phe Trp Gly Thr
                        275                 280                 285

Thr Asn Asp Leu Asp Asp Val Leu Lys Leu Val Ser Glu Gly Lys Val
                    290                 295                 300

Lys Pro Val Val Arg Ser Ala Lys Leu Lys Glu Leu Pro Glu Tyr Ile
                305                 310                 315                 320

Glu Lys Leu Arg Asn Asn Ala Tyr Glu Gly Arg Val Val Phe Asn Pro
                                325                 330                 335

<210> SEQ ID NO 9
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 9
atgtctatcc cgtcttctca gtatggtttc gtatttaaca acagtctggt tctgaaactg        60
cgcaacgatc tgccagtaca caagccgaaa gctggtcaac tgctgctgaa agtagatgca       120
gtaggtctgt gccactctga tctgcacgtt atctacgaag gcctggactg cggtgacaac       180
tacgttatgg gtcacgaaat cgctggtacc gttgctgctg ttggtgatga cgttatcaac       240
tacaaagtag gtgaccgtgt agcttgtgtt ggtccgaacg gttgcggtgg ttgcaaatac       300
tgccgtggtc tatcgacaa cgtttgcaaa aacgctttcg gtgactggtt cggtctgggt       360
tatgatggtg gctatcaaca atacctgctg gtaactcgcc cgcgtaacct gtctcgtatc       420
ccggataacg tatctgctga tgttgctgct gcttctaccg acgctgttct gactccgtac       480
cacgctatca aaatggctca ggtttctccg acctctaaca tcctgctgat cggtgctggt       540
ggtctgggtg gtaacgctat ccaggttgct aaagcattcg gtgctaaagt taccgttctg       600
gacaaaaaaa agaagctcg tgaccaggct aaaaaactgg gtgctgacgc tgtttacgaa       660
accctgccgg aatctatctc tccgggttct ttctctgctt gcttcgactt cgtttctgtt       720
caggctacct tcgacgtttg ccagaaatac gttgaaccga aggtgttat catgccggtt       780 ggtctgggtg ctccgaacct gtcttttaac ctggttgacc tggctctgcg tgaaatccgt       840
atcctgggtt ctttctgggg taccaccaac gacctggacg acgttctgaa actggtttct       900
gaaggtaaag ttaaaccggt tgtacgttct gctaaactga agaactgcc ggaatacatc       960 gaaaaactgc gtaacaacgc ttacgaaggt cgtgttgttt tcaacccgta a              1011

<210> SEQ ID NO 10
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 10

Met Ser Ile Pro Ser Ser Gln Tyr Gly Phe Val Phe Asn Lys Gln Ser
```

```
              1               5              10              15
            Gly Leu Lys Leu Arg Asn Asp Leu Pro Val His Lys Pro Lys Ala Gly
                           20                  25                  30

Gln Leu Leu Lys Val Asp Ala Val Gly Leu Cys His Ser Asp Leu
                           35                  40                  45

His Val Ile Tyr Glu Gly Leu Asp Cys Gly Asp Asn Tyr Val Met Gly
                50                  55                  60

His Glu Ile Ala Gly Thr Val Ala Ala Val Gly Asp Asp Val Ile Asn
             65                  70                  75                  80

Tyr Lys Val Gly Asp Arg Val Ala Cys Val Gly Pro Asn Gly Cys Gly
                               85                  90                  95

Gly Cys Lys Tyr Cys Arg Gly Ala Ile Asp Asn Val Cys Lys Asn Ala
                          100                 105                 110

Phe Gly Asp Trp Phe Gly Leu Gly Tyr Asp Gly Gly Tyr Gln Gln Tyr
                          115                 120                 125

Leu Leu Val Thr Arg Pro Arg Asn Leu Ser Arg Ile Pro Asp Asn Val
                          130                 135                 140

Ser Ala Asp Val Ala Ala Ala Ser Thr Asp Ala Val Leu Thr Pro Tyr
             145                 150                 155                 160

His Ala Ile Lys Met Ala Gln Val Ser Pro Thr Ser Asn Ile Leu Leu
                               165                 170                 175

Ile Gly Ala Gly Gly Leu Gly Gly Asn Ala Ile Gln Val Ala Lys Ala
                          180                 185                 190

Phe Gly Ala Lys Val Thr Val Leu Asp Lys Lys Glu Ala Arg Asp
                          195                 200                 205

Gln Ala Lys Lys Leu Gly Ala Asp Ala Val Tyr Glu Thr Leu Pro Glu
                          210                 215                 220

Ser Ile Ser Pro Gly Ser Phe Ser Ala Cys Phe Asp Phe Val Ser Val
             225                 230                 235                 240

Gln Ala Thr Phe Asp Val Cys Gln Lys Tyr Val Glu Pro Lys Gly Val
                               245                 250                 255

Ile Met Pro Val Gly Leu Gly Ala Pro Asn Leu Ser Phe Asn Leu Val
                          260                 265                 270

Asp Leu Ala Leu Arg Glu Ile Arg Ile Leu Gly Ser Phe Trp Gly Thr
                          275                 280                 285

Thr Asn Asp Leu Asp Asp Val Leu Lys Leu Val Ser Glu Gly Lys Val
                          290                 295                 300

Lys Pro Val Val Arg Ser Ala Lys Leu Lys Glu Leu Pro Glu Tyr Ile
             305                 310                 315                 320

Glu Lys Leu Arg Asn Asn Ala Tyr Glu Gly Arg Val Val Phe Asn Pro
                               325                 330                 335
```

<210> SEQ ID NO 11
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 11

```
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag cctggactg cggtgacaac    180 tacgttatgg gtcacgaaat cgctggtacc gttgctgctg ttggtgatga cgttatcaac   240
```

```
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccgctg gtaactcgcc cgcgtaacct gtctcgtatc     420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa agaagctcg tgaccaggct aaaaaactgg gtgctgacgc tgtttacgaa     660
accctgccgg aatctatctc tccgggttct ttctctgctt gcttcgactt cgtttctgtt    720
caggctacct tcgacgtttg ccagaaatac gttgaaccga aggtgttat catgccggtt     780 ggtctgtatg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt caacccgta a             1011

<210> SEQ ID NO 12
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 12

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220
```

```
Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Tyr Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 13
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 13

```
atgtctatcc cgtcttctca gtatggtttc gtatttaaca acagtctgg  tctgaaactg      60
cgcaacgatc tgccagtaca caagccgaaa gctggtcaac tgctgctgaa agtagatgca    120
gtaggtctgt gccactctga tctgcacgtt atctacgaag cctggactg  cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg ctatcaacaa tacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat  catgccggtt    780
ggtctgggtg ctccgaacct gtcttttaac ctgggtgacc tggcttttcg tgaaatccgt    840
atcctgggtt ctttctgggg taccaccaac gacctggacg acgttctgaa actggtttct    900
gaaggtaaag ttaaaccggt tgtacgttct gctaaactga agaactgcc  ggaatacatc    960
gaaaaactgc gtaacaacgc ttacgaaggt cgtgttgttt tcaacccgta a          1011
```

<210> SEQ ID NO 14
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 14

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
```

```
                     20                  25                  30
Gln Leu Leu Leu Lys Val Asp Ala Val Gly Leu Cys His Ser Asp Leu
             35                  40                  45

His Val Ile Tyr Glu Gly Leu Asp Cys Gly Asp Asn Tyr Val Met Gly
     50                  55                  60

His Glu Ile Ala Gly Thr Val Ala Ala Val Gly Asp Asp Val Ile Asn
 65                  70                  75                  80

Tyr Lys Val Gly Asp Arg Val Ala Cys Val Gly Pro Asn Gly Cys Gly
                 85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Phe Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 15
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 15

```
atgtctatcc cgtcttctca gtatggtttc gtatttaaca aacagtctgg tctgaaactg        60
cgcaacgatc tgccagtaca caagccgaaa gctggtcaac tgctgctgaa agtagatgca       120
gtaggtctgt gccactctga tctgcacgtt atctacgaag gcctggacat tggtgacaac       180
tacgttatgg gtcacgaaat cgctggtacc gttgctgctg ttggtgatga cgttatcaac       240
tacaaagtag gtgaccgtgt agcttgtgtt ggtccgaacg gttgcggtgg ttgcaaatac       300
```

-continued

```
tgccgtggtg ctatcgacaa cgtttgcaaa aacgctttcg gtgactggtt cggtctgggt      360
tatgatggtg ctatcaaca ataccctgctg gtaactcgcc cgcgtaacct gtctcgtatc      420
ccggataacg tatctgctga tgttgctgct gcttctaccg acgctgttct gactccgtac      480
cacgctatca aaatggctca ggtttctccg acctctaaca tcctgctgat cggtgctggt      540
ggtctgggtg gtaacgctat ccaggttgct aaagcattcg gtgctaaagt taccgttctg      600
gacaaaaaaa aagaagctcg tgaccaggct aaaaaactgg gtgctgacgc tgtttacgaa      660
accctgccgg aatctatctc tccgggttct ttctctgctt gcttcgactt cgtttctgtt      720
caggctacct tcgacgtttg ccagaaatac gttgaaccga aggtgttat catgccggtt       780
ggtctgggtg ctccgaacct gtcttttaac ctgggtgacc tggctctgcg tgaaatccgt      840
atcctgggtt ctttctgggg taccaccaac gacctggacg acgttctgaa actggtttct      900
gaaggtaaag ttaaaccggt tgtacgttct gctaaactga agaactgcc ggaatacatc       960
gaaaaactgc gtaacaacgc ttacgaaggt cgtgttgttt tcaacccgta a              1011
```

<210> SEQ ID NO 16
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 16

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Ile Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240
```

-continued

```
Gln Ala Thr Phe Asp Val Cys Gln Lys Tyr Val Glu Pro Lys Gly Val
            245                 250                 255

Ile Met Pro Val Gly Leu Gly Ala Pro Asn Leu Ser Phe Asn Leu Gly
        260                 265                 270

Asp Leu Ala Leu Arg Glu Ile Arg Ile Leu Gly Ser Phe Trp Gly Thr
    275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 17
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 17

```
atgtctatcc cgtcttctca gtatggtttc gtatttaaca acagtctggg tctgaaactg      60
cgcaacgatc tgccagtaca caagccgaaa gctggtcaac tgctgctgaa agtagatgca    120
gtaggtctgt gccactctga tctgcacgtt atctacgaag cctggactg cggtgacaac     180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga agggtgttat catgccggtt    780
ggtctgggtg ctccgaacct gtcttttaac ctgccagacc tggctctgcg tgaaatccgt    840
atcctgggtt cttctggggg taccaccaac gacctggacg acgttctgaa actggtttct    900
gaaggtaaag ttaaaccggt tgtacgttct gctaaactga agaactgcc ggaatacatc     960
gaaaaactgc gtaacaacgc ttacgaaggt cgtgttgttt tcaacccgta a             1011
```

<210> SEQ ID NO 18
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 18

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
```

```
                35                  40                  45
His Val Ile Tyr Glu Gly Leu Asp Cys Gly Asp Asn Tyr Val Met Gly
 50                  55                  60

His Glu Ile Ala Gly Thr Val Ala Ala Val Gly Asp Val Ile Asn
 65                  70                  75                  80

Tyr Lys Val Gly Asp Arg Val Ala Cys Val Gly Pro Asn Gly Cys Gly
                 85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Pro
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 19
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 19
atgtctatcc cgtcttctca gtatggtttc gtatttaaca acagtctgg tctgaaactg      60 cgcaacgatc tgccagtaca aagccgaaa gctggtcaac tgctgctgaa agtagatgca     120
gtaggtctgt gccactctga tctgcacgtt atctacgaag gctggactg cggtgacaac    180 tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtc tatcgacaa cgtttgcaaa aacgctttcg gtgactggtt cggtctgggt    360
tatgatggtg gctatcaaca atacctgctg gtaactcgcc cgcgtaacct gtctcgtatc    420
```

```
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgttggacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a            1011
```

<210> SEQ ID NO 20
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 20

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255
```

```
Ile Met Pro Val Gly Leu Gly Ala Pro Asn Leu Ser Phe Asn Leu Leu
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 21
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 21
atgtctatcc cgtcttctca gtatggtttc gtatttaaca aacagtctgg tctgaaactg        60
cgcaacgatc tgccagtaca caagccgaaa gctggtcaac tgctgctgaa agtagatgca       120
gtaggtctgt gccactctga tctgcacgtt atctacgaag gcctggactg cggtgacaac       180
tacgttatgg gtcacgaaat cgctggtacc gttgctgctg ttggtgatga cgttatcaac       240
tacaaagtag gtgaccgtgt agcttgtgtt ggtccgaacg gttgcggtgg ttgcaaatac       300
tgccgtggtg ctatcgacaa cgtttgcaaa aacgctttca tggactggtt cggtctgggt       360
tatgatggtg gctatcaaca atacctgctg gtaactcgcc cgcgtaacct gtctcgtatc       420
ccggataacg tatctgctga tgttgctgct gcttctaccg acgctgttct gactccgtac       480
cacgctatca aaatggctca ggtttctccg acctctaaca tcctgctgat cggtgctggt       540
ggtctgggtg gtaacgctat ccaggttgct aaagcattcg gtgctaaagt taccgttctg       600
gacaaaaaaa agaagctcg tgaccaggct aaaaaactgg gtgctgacgc tgtttacgaa       660
accctgccgg aatctatctc tccgggttct ttctctgctt gcttcgactt cgttctgttt       720
caggctacct tcgacgtttg ccagaaatac gttgaaccga aaggtgttat catgccggtt       780
ggtctgggtg ctccgaacct gtcttttaac ctgggtgacc tggctctgcg tgaaatccgt       840
atcctgggtt ctttctgggg taccaccaac gacctggacg acgttctgaa actggtttct       900
gaaggtaaag ttaaaccggt tgtacgttct gctaaactga agaactgcc ggaatacatc       960 gaaaaactgc gtaacaacgc ttacgaaggt cgtgttgttt tcaacccgta a              1011

<210> SEQ ID NO 22
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 22

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
```

```
            50                  55                  60
His Glu Ile Ala Gly Thr Val Ala Ala Val Gly Asp Val Ile Asn
 65                  70                  75                  80

Tyr Lys Val Gly Asp Arg Val Ala Cys Val Gly Pro Asn Gly Cys Gly
                 85                  90                  95

Gly Cys Lys Tyr Cys Arg Gly Ala Ile Asp Asn Val Cys Lys Asn Ala
                100                 105                 110

Phe Met Asp Trp Phe Gly Leu Gly Tyr Asp Gly Gly Tyr Gln Gln Tyr
                115                 120                 125

Leu Leu Val Thr Arg Pro Arg Asn Leu Ser Arg Ile Pro Asp Asn Val
                130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
                180                 185                 190

Phe Gly Ala Lys Val Thr Val Leu Asp Lys Lys Glu Ala Arg Asp
                195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
                260                 265                 270

Asp Leu Ala Leu Arg Glu Ile Arg Ile Leu Gly Ser Phe Trp Gly Thr
                275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 23
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 23
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg tgactggtt cggtctgggt    360 tatgatggtg gctatcaaca ataccctgctg gtaactcgcc cgcgtaacct gtctcgtatc    420
ccggataacg tatctgctga tgttgctgct gcttctaccg acgctgttct gactccgtac    480
```

```
cacgctatca aaatggctca ggtttctccg acctctaaca tcctgctgat cggtgctggt      540
ggtctgggtg gtaacgctat ccaggttgct aaagcattcg gtgctaaagt taccgttctg      600
gacaaaaaaa aagaagctcg tgaccaggct aaaaaactgg gtgctgacgc tgtttacgaa      660
accctgccgg aatctatctc tccgggttct ttctctgctt gcttcgactt cgtttctgtt      720
caggctacct tcgacgtttg ccagaaatac gttgaaccga aaggtgttat catgccggtt      780
ggtctgggtg ctccgaacct gtcttttaac ctgagtgacc tggctctgcg tgaaatccgt      840
atcctgggtt ctttctgggg taccaccaac gacctggacg acgttctgaa actggtttct      900
gaaggtaaag ttaaaccggt tgtacgttct gctaaactga agaactgcc ggaatacatc       960 gaaaaactgc gtaacaacgc ttacgaaggt cgtgttgttt tcaacccgta a              1011
```

<210> SEQ ID NO 24
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 24

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Ser
            260                 265                 270
```

```
Asp Leu Ala Leu Arg Glu Ile Arg Ile Leu Gly Ser Phe Trp Gly Thr
                275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 25
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 25
atgtctatcc cgtcttctca gtatggtttc gtatttaaca acagtctgg tctgaaactg      60 cgcaacgatc tgccagtaca aagccgaaa gctggtcaac tgctgctgaa agtagatgca     120
gtaggtctgt gccactctga tctgcacgtt atctacgaag cctggactg cggtgacaac     180 tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccgtctg gtaactcgcc gcgtaacct gtctcgtatc     420 ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg taacgctat ccaggttgct aaagcattcg gtgctaaagt taccgttctg     600
gacaaaaaaa agaagctcg tgaccaggct aaaaaactgg gtgctgacgc tgtttacgaa     660
accctgccgg aatctatctc tccgggttct ttctctgctt gcttcgactt cgtttctgtt     720 caggctaccct tcgacgtttg ccagaaatac gttgaaccga aaggtgttat catgccggtt     780
ggtctgggtg ctccgaacct gtctttaac ctgcaagacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc     960 gaaaaactgc gtaacaacgc ttacgaaggt cgtgttgttt tcaacccgta a            1011

<210> SEQ ID NO 26
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 26

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Ala Val Gly Asp Asp Val Ile Asn
```

```
              65                  70                  75                  80
        Tyr Lys Val Gly Asp Arg Val Ala Cys Val Gly Pro Asn Gly Cys Gly
                        85                  90                  95
        Gly Cys Lys Tyr Cys Arg Gly Ala Ile Asp Asn Val Cys Lys Asn Ala
                       100                 105                 110
        Phe Gly Asp Trp Phe Gly Leu Gly Tyr Asp Gly Gly Tyr Gln Gln Tyr
                       115                 120                 125
        Leu Leu Val Thr Arg Pro Arg Asn Leu Ser Arg Ile Pro Asp Asn Val
                130                 135                 140
        Ser Ala Asp Val Ala Ala Ala Ser Thr Asp Ala Val Leu Thr Pro Tyr
        145                 150                 155                 160
        His Ala Ile Lys Met Ala Gln Val Ser Pro Thr Ser Asn Ile Leu Leu
                        165                 170                 175
        Ile Gly Ala Gly Gly Leu Gly Gly Asn Ala Ile Gln Val Ala Lys Ala
                       180                 185                 190
        Phe Gly Ala Lys Val Thr Val Leu Asp Lys Lys Glu Ala Arg Asp
                       195                 200                 205
        Gln Ala Lys Lys Leu Gly Ala Asp Ala Val Tyr Glu Thr Leu Pro Glu
                210                 215                 220
        Ser Ile Ser Pro Gly Ser Phe Ser Ala Cys Phe Asp Phe Val Ser Val
        225                 230                 235                 240
        Gln Ala Thr Phe Asp Val Cys Gln Lys Tyr Val Glu Pro Lys Gly Val
                        245                 250                 255
        Ile Met Pro Val Gly Leu Gly Ala Pro Asn Leu Ser Phe Asn Leu Gln
                       260                 265                 270
        Asp Leu Ala Leu Arg Glu Ile Arg Ile Leu Gly Ser Phe Trp Gly Thr
                       275                 280                 285
        Thr Asn Asp Leu Asp Asp Val Leu Lys Leu Val Ser Glu Gly Lys Val
                290                 295                 300
        Lys Pro Val Val Arg Ser Ala Lys Leu Lys Glu Leu Pro Glu Tyr Ile
        305                 310                 315                 320
        Glu Lys Leu Arg Asn Asn Ala Tyr Glu Gly Arg Val Val Phe Asn Pro
                        325                 330                 335

<210> SEQ ID NO 27
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 27
atgtctatcc cgtcttctca gtatggtttc gtatttaaca acagtctgg  tctgaaactg      60 cgcaacgatc tgccagtaca aagccgaaa gctggtcaac tgctgctgaa agtagatgca     120
gtaggtctgt gccactctga tctgcacgtt atctacgaag cctggactg cggtgacaac     180 tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
```

```
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt     780 ggtctgggtg ctccgaacct gtcttttaac ctgcatgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a             1011
```

<210> SEQ ID NO 28
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 28

```
Met Ser Ile Pro Ser Ser Gln Tyr Gly Phe Val Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu His
            260                 265                 270

Asp Leu Ala Leu Arg Glu Ile Arg Ile Leu Gly Ser Phe Trp Gly Thr
        275                 280                 285
```

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 29
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 29
atgtctatcc cgtcttctca gtatggtttc gtatttaaca acagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt     780
ggtctgggtg ctccgaacct gtcttttaac ctgacagacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc     960
gaaaaactgc gtaacaacgc ttacgaaggt cgtgttgttt tcaacccgta a              1011

<210> SEQ ID NO 30
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 30

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly

```
                    85              90              95
Gly Cys Lys Tyr Cys Arg Gly Ala Ile Asp Asn Val Cys Lys Asn Ala
                100             105             110

Phe Gly Asp Trp Phe Gly Leu Gly Tyr Asp Gly Gly Tyr Gln Gln Tyr
            115             120             125

Leu Leu Val Thr Arg Pro Arg Asn Leu Ser Arg Ile Pro Asp Asn Val
        130             135             140

Ser Ala Asp Val Ala Ala Ala Ser Thr Asp Ala Val Leu Thr Pro Tyr
145             150             155             160

His Ala Ile Lys Met Ala Gln Val Ser Pro Thr Ser Asn Ile Leu Leu
                165             170             175

Ile Gly Ala Gly Gly Leu Gly Gly Asn Ala Ile Gln Val Ala Lys Ala
                180             185             190

Phe Gly Ala Lys Val Thr Val Leu Asp Lys Lys Glu Ala Arg Asp
            195             200             205

Gln Ala Lys Lys Leu Gly Ala Asp Ala Val Tyr Glu Thr Leu Pro Glu
        210             215             220

Ser Ile Ser Pro Gly Ser Phe Ser Ala Cys Phe Asp Phe Val Ser Val
225             230             235             240

Gln Ala Thr Phe Asp Val Cys Gln Lys Tyr Val Glu Pro Lys Gly Val
                245             250             255

Ile Met Pro Val Gly Leu Gly Ala Pro Asn Leu Ser Phe Asn Leu Thr
                260             265             270

Asp Leu Ala Leu Arg Glu Ile Arg Ile Leu Gly Ser Phe Trp Gly Thr
        275             280             285

Thr Asn Asp Leu Asp Asp Val Leu Lys Leu Val Ser Glu Gly Lys Val
        290             295             300

Lys Pro Val Val Arg Ser Ala Lys Leu Lys Glu Leu Pro Glu Tyr Ile
305             310             315             320

Glu Lys Leu Arg Asn Asn Ala Tyr Glu Gly Arg Val Val Phe Asn Pro
                325             330             335
```

<210> SEQ ID NO 31
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 31

```
atgtctatcc cgtcttctca gtatggtttc gtatttaaca acagtctggt ctgaaactg     60 cgcaacgatc tgccagtaca aagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcc atgactggtt cggtctgggt    360
tatgatggtg gctatcaaca atacctgctg gtaactcgcc gcgtaacct gtctcgtatc    420 ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
```

```
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960 gaaaaactgc gtaacaacgc ttacgaaggt cgtgttgttt tcaacccgta a           1011
```

<210> SEQ ID NO 32
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 32

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe His Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
290                 295                 300
```

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
            325                 330                 335

<210> SEQ ID NO 33
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 33

```
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccgtgct gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga agggtgttat catgccggtt     780
ggtctgggtg ctccgaacct gtcttttaac ctgattgacc tggctctgcg tgaaatccgt     840
atcctgggtt ctttctgggg taccaccaac gacctggacg acgttctgaa actggttctt     900
gaaggtaaag ttaaaccggt tgtacgttct gctaaactga agaactgcc ggaatacatc     960
gaaaaactgc gtaacaacgc ttacgaaggt cgtgttgttt tcaacccgta a            1011
```

<210> SEQ ID NO 34
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 34

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala

|  | 100 | 105 | 110 |
|---|---|---|---|

Phe Gly Asp Trp Phe Gly Leu Gly Tyr Asp Gly Gly Tyr Gln Gln Tyr
    115        120        125

Leu Leu Val Thr Arg Pro Arg Asn Leu Ser Arg Ile Pro Asp Asn Val
130        135        140

Ser Ala Asp Val Ala Ala Ser Thr Asp Ala Val Leu Thr Pro Tyr
145      150       155       160

His Ala Ile Lys Met Ala Gln Val Ser Pro Thr Ser Asn Ile Leu Leu
    165        170        175

Ile Gly Ala Gly Gly Leu Gly Gly Asn Ala Ile Gln Val Ala Lys Ala
    180        185        190

Phe Gly Ala Lys Val Thr Val Leu Asp Lys Lys Glu Ala Arg Asp
   195       200        205

Gln Ala Lys Lys Leu Gly Ala Asp Ala Val Tyr Glu Thr Leu Pro Glu
210       215        220

Ser Ile Ser Pro Gly Ser Phe Ser Ala Cys Phe Asp Phe Val Ser Val
225      230       235       240

Gln Ala Thr Phe Asp Val Cys Gln Lys Tyr Val Glu Pro Lys Gly Val
    245        250        255

Ile Met Pro Val Gly Leu Gly Ala Pro Asn Leu Ser Phe Asn Leu Ile
    260        265        270

Asp Leu Ala Leu Arg Glu Ile Arg Ile Leu Gly Ser Phe Trp Gly Thr
   275       280        285

Thr Asn Asp Leu Asp Asp Val Leu Lys Leu Val Ser Glu Gly Lys Val
290       295        300

Lys Pro Val Val Arg Ser Ala Lys Leu Lys Glu Leu Pro Glu Tyr Ile
305      310       315       320

Glu Lys Leu Arg Asn Asn Ala Tyr Glu Gly Arg Val Val Phe Asn Pro
    325        330        335

<210> SEQ ID NO 35
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 35

```
atgtctatcc cgtcttctca gtatggtttc gtatttaaca acagtctggt ctgaaactg      60 cgcaacgatc tgccagtaca caagccgaaa gctggtcaac tgctgctgaa agtagatgca     120
gtaggtctgt gccactctga tctgcacgtt atctacgaag gcctggackk yggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa acgctttcg gtgactggtt cggtctgggt     360
tatgatggtg gctatcaaca ataccctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgttctgtt      720 caggctacct tcgacgtttg ccagaaatac gttgaaccga aggtgttat catgccggtt      780
```

```
ggtctgggtg ctccgaacct gtcttttaac ctgggtgacc tggctctgcg tgaaatccgt    840
atcctgggtt ctttcyrrgg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a             1011
```

<210> SEQ ID NO 36
<211> LENGTH: 336
<212> TYPE: PRT
<213> ORGANISM: Artificial Sequence
<220> FEATURE:
<223> OTHER INFORMATION: KRED-NADH-102 variant
<221> NAME/KEY: unsure
<222> LOCATION: 57
<223> OTHER INFORMATION: Xaa = Phe, Cys, Gly, Val
<221> NAME/KEY: unsure
<222> LOCATION: 286
<223> OTHER INFORMATION: Xaa = Gln, Ter, Trp, Arg

<400> SEQUENCE: 36

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Xaa Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Xaa Gly Thr
        275                 280                 285
```

```
Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 37
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 37
atgtctatcc cgtcttctca gtatggtttc gtatttaaca acagtctggg tctgaaactg      60
cgcaacgatc tgccagtaca aagccgaaaa gctggtcaac tgctgctgaa agtagatgca     120
gtaggtctgt gccactctga tctgcacgtt atctacgaag cctggactg cggtgacaac      180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccctgctg gtaactcgcc cgcgtaacct gtctcgtatc    420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt      780
ggtctgggtg ctccgaacct gtcttttaac ctgtgggacc tggctctgcg tgaaatccgt     840
atcctgggtt ctttctgggg taccaccaac gacctggacg acgttctgaa actggttct     900
gaaggtaaag ttaaaccggt tgtacgttct gctaaactga agaactgcc ggaatacatc     960
gaaaaactgc gtaacaacgc ttacgaaggt cgtgttgttt tcaacccgta a             1011

<210> SEQ ID NO 38
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 38

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
```

85                  90                  95
Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
        130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Trp
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 39
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 39
atgtctatcc cgtcttctca gtatggtttc gtatttaaca acagtctggt ctgaaactg      60 cgcaacgatc tgccagtaca aagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccctgct gtaactcgcc gcgtaacct gtctcgtatc     420 ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660

```
accctgccgg aatctatctc tccgggttct ttctctgctt gcttcgactt cgtttctgtt    720
caggctacct tcgacgtttg ccagaaatac gttgaaccga aaggtgttat catgccggtt    780
ggtctgggtg ctccgaacct gtcttttaac ctgggtgacc tggctctgcg tgaacatcgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a            1011
```

<210> SEQ ID NO 40
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 40

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu His Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300
```

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 41
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 41

| | | | | | |
|---|---|---|---|---|---|
| atgtctatcc | cgtcttctca | gtatggtttc | gtatttaaca | aacagtctgg | tctgaaactg | 60 |
| cgcaacgatc | tgccagtaca | caagccgaaa | gctggtcaac | tgctgctgaa | agtagatgca | 120 |
| gtaggtctgt | gccactctga | tctgcacgtt | atctacgaag | gcctggactg | cggtgacaac | 180 |
| tacgttatgg | gtcacgaaat | cgctggtacc | gttgctgctg | ttggtgatga | cgttatcaac | 240 |
| tacaaagtag | gtgaccgtgt | agcttgtgtt | ggtccgaacg | gttgcggtgg | ttgcaaatac | 300 |
| tgccgtggtg | ctatcgacaa | cgtttgcaaa | aacgctttcg | gtgactggtt | cggtctgggt | 360 |
| tatgatggtg | gctatcaaca | atacctgctg | gtaactcgcc | cgcgtaacct | gtctcgtatc | 420 |
| ccggataacg | tatctgctga | tgttgctgct | gcttctaccg | acgctgttct | gactccgtac | 480 |
| cacgctatca | aaatggctca | ggtttctccg | acctctaaca | tcctgctgat | cggtgctggt | 540 |
| ggtctgggtg | gtaacgctat | ccaggttgct | aaagcattcg | gtgctaaagt | taccgttctg | 600 |
| gacaaaaaaa | aagaagctcg | tgaccaggct | aaaaaactgg | gtgctgacgc | tgtttacgaa | 660 |
| accctgccgg | aatctatctc | tccgggttct | ttctctgctt | gcttcgactt | cgtttctgtt | 720 |
| caggctacct | tcgacgtttg | ccagaaatac | gttgaaccga | aggtgttat | catgccggtt | 780 |
| ggtctgcatg | ctccgaacct | gtcttttaac | ctgggtgacc | tggctctgcg | tgaaatccgt | 840 |
| atcctgggtt | ctttctgggg | taccaccaac | gacctggacg | acgttctgaa | actggtttct | 900 |
| gaaggtaaag | ttaaaccggt | tgtacgttct | gctaaactga | agaactgcc | ggaatacatc | 960 |
| gaaaaactgc | gtaacaacgc | ttacgaaggt | cgtgttgttt | tcaacccgta | a | 1011 |

<210> SEQ ID NO 42
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 42

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala

```
            100                 105                 110
Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu His Ala Pro Asn Leu Ser Phe Asn Leu Gly
                260                 265                 270

Asp Leu Ala Leu Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
        290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 43
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 43

```
atgtctatcc cgtcttctca gtatggtttc gtatttaaca acagtctggg tctgaaactg    60
cgcaacgatc tgccagtaca caagccgaaa gctggtcaac tgctgctgaa agtagatgca   120
gtaggtctgt gccgttctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa acgctttcg gtgactggtt cggtctgggt   360
tatgatggtg gctatcaaca atacctgctg gtaactcgcc gcgtaacctg tctcgtatc    420
ccggataacg tatctgctga tgttgctgct gcttctaccg acgctgttct gactccgtac   480
cacgctatca aatggctca ggtttctccg acctctaaca tcctgctgat cggtgctggt    540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt   720
caggctacct tcgacgtttg ccagaaatac gttgaaccga aaggtgttat catgccggtt   780
```

```
ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a            1011
```

<210> SEQ ID NO 44
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 44

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys Arg Ser Asp Leu
        35                  40                  45

His Val Ile Tyr Glu Gly Leu Asp Cys Gly Asp Asn Tyr Val Met Gly
 50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320
```

Glu Lys Leu Arg Asn Asn Ala Tyr Glu Gly Arg Val Val Phe Asn Pro
             325                 330                 335

<210> SEQ ID NO 45
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 45

```
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt     780
ggtctgggtg ctccgaacct gatgtttaac ctgggtgacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc     960
gaaaaactgc gtaacaacgc ttacgaaggt cgtgttgttt tcaacccgta a              1011
```

<210> SEQ ID NO 46
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 46

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr

```
                115                 120                 125
Leu Leu Val Thr Arg Pro Arg Asn Leu Ser Arg Ile Pro Asp Asn Val
        130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Met Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 47
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 47
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtc ctatcgacaa cgtttgcaaa aacgctttcg gtgactggtt cggtctgggt     360
tatgatggtg gctatcaaca ataccttgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct cgacgtttg ccagaaatac gttgaaccga aggtgttat catgccggtt     780 ggtctgggtg ctccgaacct gtggtttaac ctgggtgacc tggctctgcg tgaaatccgt     840
```

```
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt caacccgta a              1011
```

<210> SEQ ID NO 48
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 48

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Trp Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 49
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 49

| | | |
|---|---|---|
| atgtctatcc cgtcttctca gtatggtttc gtatttaaca aacagtctgg tctgaaactg | 60 |
| cgcaacgatc tgccagtaca aagccgaaa gctggtcaac tgctgctgaa agtagatgca | 120 |
| gtaggtctgt gccactctga tctgcacgtt atctacgaag cctggactg cggtgacaac | 180 |
| tacgttatgg gtcacgaaat cgctggtacc gttgctgctg ttggtgatga cgttatcaac | 240 |
| tacaaagtag gtgaccgtgt agcttgtgtt ggtccgaacg gttgcggtgg ttgcaaatac | 300 |
| tgccgtggtg ctatcgacaa cgtttgcaaa aacgctttcg gtgactggtt cggtctgggt | 360 |
| tatgatggtg gctatcaaca ataccgtctg gtaactcgcc cgcgtaacct gtctcgtatc | 420 |
| ccggataacg tatctgctga tgttgctgct gcttctaccg acgctgttct gactccgtac | 480 |
| cacgctatca aaatggctca ggtttctccg acctctaaca tcctgctgat cggtgctggt | 540 |
| ggtctgggtg taacgctat ccaggttgct aaagcattcg gtgctaaagt taccgttctg | 600 |
| gacaaaaaaa aagaagctcg tgaccaggct aaaaaactgg gtgctgacgc tgtttacgaa | 660 |
| accctgccgg aatctatctc tccgggttct ttctctgctt gcttcgactt cgtttctgtt | 720 |
| caggctacct tcgacgtttg ccagaaatac gttgaaccga aggtgttat catgccggtt | 780 |
| ggtctgggtg ctccgaacct gtcttttaac ctgggtgacg ttgctctgcg tgaaatccgt | 840 |
| atcctgggtt ctttctgggg taccaccaac gacctggacg acgttctgaa actggtttct | 900 |
| gaaggtaaag ttaaaccggt tgtacgttct gctaaactga agaactgcc ggaatacatc | 960 |
| gaaaaactgc gtaacaacgc ttacgaaggt cgtgttgttt caacccgta a | 1011 |

<210> SEQ ID NO 50
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 50

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val

```
                130                 135                 140
Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
                180                 185                 190

Phe Gly Ala Lys Val Thr Val Leu Asp Lys Lys Glu Ala Arg Asp
                195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
                260                 265                 270

Asp Val Ala Leu Arg Glu Ile Arg Ile Leu Gly Ser Phe Trp Gly Thr
                275                 280                 285

Thr Asn Asp Leu Asp Asp Val Leu Lys Leu Val Ser Glu Gly Lys Val
                290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 51
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 51
atgtctatcc cgtcttctca gtatggtttc gtatttaaca acagtctgg tctgaaactg      60 cgcaacgatc tgccagtaca aagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaaattg gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg ctatcaaca ataccctgctg gtaactcgcc cgcgtaacct gtctcgtatc     420
ccggataacg tatctgctga tgttgctgct gcttctaccg acgctgttct gactccgtac     480
cacgctatca aatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaaactgg gtgctgacgc tgtttacgaa     660
accctgccgg aatctatctc tccgggttct ttctctgctt gcttcgactt cgtttctgtt     720 caggctaccct tcgacgtttg ccagaaatac gttgaaccga aggtgttat catgccggtt     780 ggtctgggtg ctccgaacct gtcttttaac ctgggtgacc tggctctgcg tgaaatccgt     840 atcctggtt ctttctgggg taccaccaac gacctggacg acgttctgaa actggtttct     900
gaaggtaaag ttaaaccggt tgtacgttct gctaaactga agaactgcc ggaatacatc     960
```
gaaaaactgc gtaacaacgc ttacgaaggt cgtgttgttt tcaacccgta a        1011

<210> SEQ ID NO 52
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 52

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Val Ile Asn
65                  70                  75                  80

Tyr Lys Ile Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 53
<211> LENGTH: 1011

<212> TYPE: DNA
<213> ORGANISM: Artificial Sequence
<220> FEATURE:
<223> OTHER INFORMATION: KRED-NADH-102 variant

<400> SEQUENCE: 53

```
atgtctatcc cgtcttctca gtatggtttc gtatttaaca acagtctgg tctgaaactg      60
cgcaacgatc tgccagtaca caagccgaaa gctggtcaac tgctgctgaa agtagatgca    120
gtaggtctgt gccactctga tctgcacgtt atcgatgaag cctggactg cggtgacaac     180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccctgctg gtaactcgcc cgcgtaacct gtctcgtatc   420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt accgttctg    600
gacaaaaaaa agaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt     780
ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960
gaaaaactgc gtaacaacgc ttacgaaggt cgtgttgttt tcaacccgta a            1011
```

<210> SEQ ID NO 54
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 54

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Asp Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
```

```
                145                 150                 155                 160
His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
                260                 265                 270

Asp Leu Ala Leu Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
        290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 55
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 55
atgtctatcc cgtcttctca gtatggtttc gtatttaaca acagtctgg tctgaaactg      60 cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt accgttctg    600 gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggctctgcg tgaaggcgt    840 atcctgggtt ctttctgggg taccaccaac gacctggacg acgttctgaa actggtttct    900
gaaggtaaag ttaaaccggt tgtacgttct gctaaactga agaactgcc ggaatacatc    960 gaaaaactgc gtaacaacgc ttacgaaggt cgtgttgttt tcaacccgta a           1011
```

<210> SEQ ID NO 56
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 56

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 57
<211> LENGTH: 1011
<212> TYPE: DNA
<213> ORGANISM: Artificial Sequence
<220> FEATURE:

<223> OTHER INFORMATION: KRED-NADH-102 variant

<400> SEQUENCE: 57

```
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atcagtgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt      780
ggtctgggtg ctccgaacct gtcttttaac ctgggtgacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc      960
gaaaaactgc gtaacaacgc ttacgaaggt cgtgttgttt caacccgta a              1011
```

<210> SEQ ID NO 58
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 58

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Ser Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
```

```
              165                 170                 175
Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 59
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 59
atgtctatcc cgtcttctca gtatggtttc gtatttaaca acagtctggg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccgtctg gtaactcgcc cgcgtaacct gtctcgtatc   420
ccggataacg tatctgctga tgttgctgct gcttctaccg cgctgttct gactccgtac    480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa agaagctcg tgaccaggct aaaaaactgg gtgctgacgc tgtttacgaa    660
accctgccgg aatctatctc tccgggttct ttctctgctt gcttcgactt cgtttctgtt   720
caggctacct cgacgtttg ccagaaatac gttgaaccga aggtgttat catgccggtt     780
ggtctgggtg ctccgaacct gtcttttaac ctgggtgacc tggctctgcg tgaacaacgt   840
atcctggggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

<210> SEQ ID NO 60
<211> LENGTH: 336
```

<212> TYPE: PRT
<213> ORGANISM: Artificial Sequence
<220> FEATURE:
<223> OTHER INFORMATION: KRED-NADH-102 variant

<400> SEQUENCE: 60

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Gln Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 61
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 61

```
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc gcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa agaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgaca ttgctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt caacccgta a           1011
```

<210> SEQ ID NO 62
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 62

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
```

```
                180             185             190
Phe Gly Ala Lys Val Thr Val Leu Asp Lys Lys Glu Ala Arg Asp
            195                 200                 205
Gln Ala Lys Lys Leu Gly Ala Asp Ala Val Tyr Glu Thr Leu Pro Glu
        210                 215                 220
Ser Ile Ser Pro Gly Ser Phe Ser Ala Cys Phe Asp Phe Val Ser Val
225                 230                 235                 240
Gln Ala Thr Phe Asp Val Cys Gln Lys Tyr Val Glu Pro Lys Gly Val
                245                 250                 255
Ile Met Pro Val Gly Leu Gly Ala Pro Asn Leu Ser Phe Asn Leu Gly
                260                 265                 270
Asp Ile Ala Leu Arg Glu Ile Arg Ile Leu Gly Ser Phe Trp Gly Thr
            275                 280                 285
Thr Asn Asp Leu Asp Asp Val Leu Lys Leu Val Ser Glu Gly Lys Val
        290                 295                 300
Lys Pro Val Val Arg Ser Ala Lys Leu Lys Glu Leu Pro Glu Tyr Ile
305                 310                 315                 320
Glu Lys Leu Arg Asn Asn Ala Tyr Glu Gly Arg Val Val Phe Asn Pro
                325                 330                 335
```

<210> SEQ ID NO 63
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 63

```
atgtctatcc cgtcttctca gtatggtttc gtatttaaca acagtctgg  tctgaaactg    60
cgcaacgatc tgccagtaca caagccgaaa gctggtcaac tgctgctgaa agtagatgca   120
gtaggtctgt gccactctga tctgcacgtt atctacgaag cctgctttg  cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg ctatcaaca  ataccgtgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa agaagctcg  tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aggtgttat  catgccggtt   780
ggtctgggtg ctccgaacct gtctttaac  ctgggtgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc  ggaatacatc   960
gaaaaactgc gtaacaacgc ttacgaaggt cgtgttgttt tcaacccgta  a           1011
```

<210> SEQ ID NO 64
<211> LENGTH: 336
<212> TYPE: PRT
<213> ORGANISM: Artificial Sequence
<220> FEATURE:

<223> OTHER INFORMATION: KRED-NADH-102 variant

<400> SEQUENCE: 64

| Met | Ser | Ile | Pro | Ser | Ser | Gln | Tyr | Gly | Phe | Val | Phe | Asn | Lys | Gln | Ser |
|---|---|---|---|---|---|---|---|---|---|---|---|---|---|---|---|
| 1 | | | | 5 | | | | | 10 | | | | | 15 | |

Gly Leu Lys Leu Arg Asn Asp Leu Pro Val His Lys Pro Lys Ala Gly
                20                  25                  30

Gln Leu Leu Lys Val Asp Ala Val Gly Leu Cys His Ser Asp Leu
        35                  40                  45

His Val Ile Tyr Glu Gly Leu Leu Cys Gly Asp Asn Tyr Val Met Gly
 50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 65
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 65
atgtctatcc cgtcttctca gtatggtttc gtatttaaca aacagtctgg tctgaaactg        60

```
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaca aacgctttcg gtgactggtt cggtctgggt    360
tatgatggtg gctatcaaca ataccgctgg taactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggctctgcg tgaaatccgt    840
atcctgggtt ctttctgggg taccaccaac gacctggacg acgttctgaa actggttttct    900 gaaggtaaag ttaaaccggt tgtacgttct gctaaactga agaactgcc ggaatacatc    960 gaaaaactgc gtaacaacgc ttacgaaggt cgtgttgttt caacccgta a             1011
```

<210> SEQ ID NO 66
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 66

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Thr Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Lys Glu Ala Arg Asp
```

|     |     |     |     | 195 |     |     |     | 200 |     |     |     | 205 |     |     |
| --- | --- | --- | --- | --- | --- | --- | --- | --- | --- | --- | --- | --- | --- | --- |

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 67
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 67

```
atgtctatcc cgtcttctca gtatggtttc gtatttaaca acagtctgg tctgaaactg      60
cgcaacgatc tgccagtaca caagccgaaa gctggtcaac tgctgctgaa agtagatgca     120
gtaggtctgt gccactctga tctgcacgtt atctacgaag cctggactg cggtgacaac      180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca ataccctgctg gtaactcgcc gcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tagtggttct ttctctgctt gcttcgactt cgtttctgtt     720
caggctacct tcgacgtttg ccagaaatac gttgaaccga agtgtattat catgccggtt     780
ggtctgggtg ctccgaacct gtcttttaac ctgggtgacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc      960
gaaaaactgc gtaacaacgc ttacgaaggt cgtgttgttt tcaacccgta a             1011
```

<210> SEQ ID NO 68
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 68

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
50                  55                  60

His Glu Ile Ala Gly Thr Val Ala Ala Val Gly Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
            195                 200                 205

Gln Ala Lys Lys Leu Gly Ala Asp Ala Val Tyr Glu Thr Leu Pro Glu
210                 215                 220

Ser Ile Ser Ser Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
275                 280                 285

Thr Asn Asp Leu Asp Asp Val Leu Lys Leu Val Ser Glu Gly Lys Val
            290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 69
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 69
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180

```
tacgttatgg gtcacgaaat cgctggtacc gttgctgctg ttggtgatga cgttatcaac      240
tacaaagtag gtgaccgtgt agcttgtgtt ggtccgaacg gttgcggtgg ttgcaaatac      300
tgccgtggtg ccatcgacaa cgtttgcaaa aacgctttcg gtgactggtt cggtctgggt      360
tatgatggtg gctatcaaca atacctgctg gtaactcgcc cgcgtaacct ggtccgtatc      420
ccggataacg tatcttcgga tgttgctgct gcttctaccg acgctgttct gactccgtac      480
cacgctatca aaatggctca ggtttctccg acctctaaca tcctgctgat cggtgctggt      540
ggtctgggtg gtaacgctat ccaggttgct aaagcattcg gtgctaaagt taccgttctg      600
gacaaaaaaa aagaagctcg tgaccaggct aaaaaactgg gtgctgacgc tgtttacgaa      660
accctgccgg aatctatctc tccgggttct ttctctgctt gcttcgactt cgtttctgtt      720
caggctacct tcgacgtttg ccagaaatac gttgaaccga aggtgttat cgtgccggtt      780 ggtctgggtg ctccgaacct gtcttttaac ctgggtgacc tggctctgcg tgaaatccgt      840
atcctgggtt ctttctgggg taccagcaac gacctggacg acgttctgaa actggtttct      900
gaaggtaaag ttaaaccggt tgtacgttct gctaaactga agaactgcc ggaatacatc      960 gaaaaactgc gtaacaacgc ttacgaaggt cgtgttgttt tcaacccgta a             1011
```

<210> SEQ ID NO 70
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 70

```
Met Ser Ile Pro Ser Ser Gln Tyr Gly Phe Val Phe Asn Lys Gln Ser
1               5                  10                 15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Tyr Glu Gly Leu Asp Cys Gly Asp Asn Tyr Val Met Gly
        50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                    85                  90                  95

Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Val Arg Ile Pro Asp Asn Val
        130                 135                 140

Ser Ser Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
```

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
            245                 250                 255

Ile Val Pro Val Gly Leu Gly Ala Pro Asn Leu Ser Phe Asn Leu Gly
        260                 265                 270

Asp Leu Ala Leu Arg Glu Ile Arg Ile Leu Gly Ser Phe Trp Gly Thr
    275                 280                 285

Ser Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 71
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 71

```
atgtcgatcc cgtcttctca gtatggtttc gtatttaaca acagtctgg tctgaaactg      60
cgcaacgatc tgccagtaca caagccgaaa gctggtcaac tgctgctgaa agtagatgca     120
gtaggtctgt gccactctga tctgcacgtt atctacgaag cctggactg cggtgacaac      180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct agaaaactgg gtgctgacgc tgtttacgaa      660
accctgccgg aatctatctc tccgggttct ttctctgctt gcttcgactt cgtttctgtt     720
caggctacct tcgacgtttg ccagaaatac gttgaaccga aaggtgttat catgccggtt     780
ggtctgggtg ctccgaacct gtcttttaac ctgggtgacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc      960
gaaaaactgc gtaacaacgc ttacgaaggt cgtgttgttt tcaacccgta a             1011
```

<210> SEQ ID NO 72
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 72

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
 50                  55                  60

His Glu Ile Ala Gly Thr Val Ala Ala Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Arg Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 73
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 73
atgtcgatcc cgtcttctca gtatggtttc gtatttaaca aacagtctgg tctgaaactg      60
cgcaacgatc tgccagtaca caagccgaaa gctggtcaac tgctgctgag agtagatgca     120
gtaggtctgt gccactctga tctgcacgtt atctacgaag gcctggactg cggtgacaac     180
tacgttatgg gtcacgaaat cgctggtacc gttgctgctg gtgatga cgttatcaac     240

```
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa agaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960 gaaaaactgc gtaacaacgc ttacgaaggt cgtgttgttt tcaacccgta a           1011
```

<210> SEQ ID NO 74
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 74

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Arg Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
```

-continued

```
                225                 230                 235                 240
        Gln Ala Thr Phe Asp Val Cys Gln Lys Tyr Val Glu Pro Lys Gly Val
                        245                 250                 255

Ile Met Pro Val Gly Leu Gly Ala Pro Asn Leu Ser Phe Asn Leu Gly
                        260                 265                 270

Asp Leu Ala Leu Arg Glu Ile Arg Ile Leu Gly Ser Phe Trp Gly Thr
                        275                 280                 285

Thr Asn Asp Leu Asp Asp Val Leu Lys Leu Val Ser Glu Gly Lys Val
                        290                 295                 300

Lys Pro Val Val Arg Ser Ala Lys Leu Lys Glu Leu Pro Glu Tyr Ile
        305                 310                 315                 320

Glu Lys Leu Arg Asn Asn Ala Tyr Glu Gly Arg Val Val Phe Asn Pro
                        325                 330                 335
```

<210> SEQ ID NO 75
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 75

```
atgtctatcc cgtcttctca gtatggtttc gtatttaaca aacagtctgg tctgaaactg      60
cgcaacgatc tgccagtaca aagccgaaa gctggtcaac tgctgctgag agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgacggtg ctatcaaca ataccctgctg gtaactcgcc gcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg taacgctat ccaggttgct aaagcattcg gtgctaaagt taccgttctg     600
gacaaaaaaa agaagctcg tgaccaggct agaaaactgg gtgctgacgc tgtttacgaa     660
accctgccgg aatctatctc tccgcgttct ttctctgctt gcttcgactt cgtttctgtt     720
caggctacct cgacgtttg ccagaaatac gttgaaccga aaggtgttat catgccggtt     780
ggtctgggtg ctccgaacct gtcttttaac ctgggtgacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc     960
gaaaaactgc gtaacaacgc ttacgaaggt cgtgttgttt tcaacccgta a            1011
```

<210> SEQ ID NO 76
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 76

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30
```

Gln Leu Leu Leu Arg Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
        130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
            195                 200                 205

Gln Ala Arg Lys Leu Gly Ala Asp Ala Val Tyr Glu Thr Leu Pro Glu
        210                 215                 220

Ser Ile Ser Pro Arg Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
        290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 77
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 77
atgtcgatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg cggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360

```
tatgacggtg gctatcaaca atacctgctg gtaactcgcc cgcgtaacct gtctcgtatc      420
ccggataacg tatctgctga tgttgctgct gcttctaccg acgctgttct gactccgtac      480
cacgctatca aaatggctca ggtttctccg acctctaaca tcctgctgat cggtgctggt      540
ggtctgggtg gtaacgctat ccaggttgct aaagcattcg gtgctaaagt taccgttctg      600
gacaaaaaaa agaagctcg tgaccaggct agaaaactgg gtgctgacgc tgtttacgaa      660
accctgccgg aatctatctc tccgcgttct ttctctgctt gcttcgactt cgtttctgtt      720
caggctacct tcgacgtttg ccagaaatac gttgaaccga aggtgttat catgccggtt      780 ggtctgggtg ctccgaacct gtcttttaac ctgggtgacc tggctctgcg tgaaatccgt      840
atcctgggtt ctttctgggg taccaccaac gacctggacg acgttctgaa actggtttct      900
gaaggtaaag ttaaaccggt tgtacgttct gctaaactga agaactgcc ggaatacatc      960 gaaaaactgc gtaacaacgc ttacgaaggt cgtgttgttt tcaacccgta a             1011
```

<210> SEQ ID NO 78  
<211> LENGTH: 336  
<212> TYPE: PRT  
<213> ORGANISM: Artificial Sequence  
<220> FEATURE:  
<223> OTHER INFORMATION: KRED-NADH-102 variant

<400> SEQUENCE: 78

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Arg Lys Leu Gly Ala Asp Ala Val Tyr Glu Thr Leu Pro Glu
    210                 215                 220

Ser Ile Ser Pro Arg Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
```

```
            245                 250                 255
Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
            290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```

<210> SEQ ID NO 79
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 79

```
atgtcgatcc cgtcttctca gtatggtttc gtatttaaca acagtctgg tctgaaactg     60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg ctatcaaca ataccctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgcgttct ttctctgctt gcttcgactt cgtttctgtt   720
caggctacct tcgacgtttg ccagaaatac gttgaaccga aggtgttat catgccggtt   780
ggtctgggtg ctccgaacct gtcttttaac ctgggtgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a          1011
```

<210> SEQ ID NO 80
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 80

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45
```

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
 65                  70                  75                  80

Tyr Lys Val Gly Asp Arg Val Ala Cys Val Gly Pro Asn Gly Cys Gly
                 85                  90                  95

Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
            195                 200                 205

Gln Ala Lys Lys Leu Gly Ala Asp Ala Val Tyr Glu Thr Leu Pro Glu
210                 215                 220

Ser Ile Ser Pro Arg Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 81
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 81
atgtctatcc gtcttctca gtatggtttc gtatttaaca aacagtctgg tctgaaactg      60
cgcaacgatc tgccagtaca caagccgaaa gctggtcaac tgctgctgag agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgacggtg gctatcaaca atacctgctg gtaactcgcc cgcgtaacct gtctcgtatc    420

```
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgcgttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a            1011
```

<210> SEQ ID NO 82
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 82

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Arg Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Arg Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
```

```
                260             265             270
Asp Leu Ala Leu Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
        290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 83
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 83
atgtcgatcc cgtcttctca gtatggtttc gtatttaaca aacagtctgg tctgaaactg      60
cgcaacgatc tgccagtaca caagccgaaa gctggtcaac tgctgctgag agtagatgca     120
gtaggtctgt gccactctga tctgcacgtt atctacgaag cctggactg cggtgacaac      180 tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa aagaagctcg tgaccaggct agaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt      780 ggtctgggtg ctccgaacct gtcttttaac ctgggtgacc tggctctgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc      960 gaaaaactgc gtaacaacgc ttacgaaggt cgtgttgttt tcaacccgta a             1011

<210> SEQ ID NO 84
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 84

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Arg Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60
```

His Glu Ile Ala Gly Thr Val Ala Ala Val Gly Asp Val Ile Asn
65                  70                  75                  80

Tyr Lys Val Gly Asp Arg Val Ala Cys Val Gly Pro Asn Gly Cys Gly
            85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
            195                 200                 205

Gln Ala Arg Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
            245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 85
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 85
atgtctatcc cgtcttctca gtatggtttc gtatttaaca acagtctggt ctgaaactg      60 cgcaacgatc tgccagtaca caagccgaaa gctggtcaac tgctgctgaa agtagatgca    120
gtaggtctgt gccactctga tctgcacgtt atctacgaag cctggactg cggtgacaac     180 tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540

```
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780 ggtctgggtg ctccgaacct gtcttttaac ctgggtgacc tggcgatgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960 gaaaaactgc gtaacaacgc ttacgaaggt cgtgttgttt tcaacccgta a            1011
```

<210> SEQ ID NO 86
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 86

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Met Arg Glu Ile Arg Ile Leu Gly Ser Phe Trp Gly Thr
```

```
              275                 280                 285
Thr Asn Asp Leu Asp Asp Val Leu Lys Leu Val Ser Glu Gly Lys Val
        290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 87
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 87
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctacgaag gcctggactg tggtgacaac     180
tacgttatgg gtcacgaaat cgctggtacc gttgctgctg ttggtgatga cgttaccaac     240
tacaaatccg gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg cgctgttct gactccgtac      480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaaactgg gtgctgacgc tgtttacgaa      660
accctgccgg aatctatctc tccgggttct ttctctgctt gcttcgactt cgtttctgtt     720
caggctacct tcgacgtttg ccagaaatac gttgaaccga aggtgttat catgccggtt      780
ggtctgggtg ctccgaacct gtctttaac ctgggtgacc tgaacatgcg tgaaatccgt      840
atcctgggtt ctttctgggg taccaccaac gacctggacg acgttctgaa actggttttct    900
gaaggtaaag ttaaaccggt tgtacgttct gctaaactga agaactgcc ggaatacatc      960
gaaaaactgc gtaacaacgc ttacgaaggt cgtgttgttt tcaacccgta a            1011

<210> SEQ ID NO 88
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 88

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Thr Asn
65                  70                  75                  80
```

Tyr Lys Ser Gly Asp Arg Val Ala Cys Val Gly Pro Asn Cys Gly
            85                  90                  95

Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Tyr Gln Gln Tyr
            115                 120                 125

Leu Leu Val Thr Arg Pro Arg Asn Leu Ser Arg Ile Pro Asp Asn Val
    130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
            165                 170                 175

Ile Gly Ala Gly Gly Leu Gly Gly Asn Ala Ile Gln Val Ala Lys Ala
                180                 185                 190

Phe Gly Ala Lys Val Thr Val Leu Asp Lys Lys Glu Ala Arg Asp
            195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
            245                 250                 255

Ile Met Pro Val Gly Leu Gly Ala Pro Asn Leu Ser Phe Asn Leu Gly
                260                 265                 270

Asp Leu Asn Met Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
            325                 330                 335

<210> SEQ ID NO 89
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 89
atgtctatcc cgtcttctca gtatggtttc gtatttaaca acagtctgg tctgaaactg    60 cgcaacgatc tgccagtaca caagccgaaa gctggtcaac tgctgctgaa agtagatgca   120
gtaggtctgt gccactctga tctgcacgtt atctacgaag gccttgactg tggtgacaac   180
tacgttatgg gtcacgaaat cgctggtacc gttgctgctg ttggtgatga cgttatcaac   240
tacaaatccg gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccttgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600

```
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt     780 ggtctgggtg ctccgaacct gtcttttaac ctgggtgacc tgaacatgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt caacccgta a              1011
```

<210> SEQ ID NO 90
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 90

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Ser Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Asn Met Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
```

```
            290               295               300
Lys Pro Val Val Arg Ser Ala Lys Leu Lys Glu Leu Pro Glu Tyr Ile
305                 310               315                 320

Glu Lys Leu Arg Asn Asn Ala Tyr Glu Gly Arg Val Val Phe Asn Pro
              325               330               335
```

<210> SEQ ID NO 91
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 91

```
atgtctatcc cgtcttctca gtatggtttc gtatttaaca acagtctgg tctgaaactg      60
cgcaacgatc tgccagtaca aagccgaaa gctggtcaac tgctgctgaa agtagatgca     120
gtaggtctgt gccactctga tctgcacgtt atctacgaag cctggactg cggtgacaac     180
tacgttatgg gtcacgaaat cgctggtacc gttgctgctg ttggtgatga cgttatcaac     240
tacaaatccg gtgaccgtgt agcttgtgtt ggtccgaacg ttgcggtgg ttgcaaatac     300
tgccgtggtg ctatcgacaa cgtttgcaaa acgctttcg gtgactggtt cggtctgggt     360
tatgatggtg gctatcaaca ataccctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaaactgg gtgctgacgc tgtttacgaa     660
acctgccgg aatctatctc tccgggttct ttctctgctt gcttcgactt cgtttctgtt     720
caggctacct cgacgtttg ccagaaatac gttgaaccga aggtgttat catgccggtt     780
ggtctgggtg ctccgaacct gtcttttaac ctgggtgacc tggcgatgcg tgaaatccgt     840
atcctgggtt ctttctgggg taccaccaac gacctggacg acgttctgaa actggtttct     900
gaaggtaaag ttaaaccggt tgtacgttct gctaaactga agaactgcc ggaatacatc     960
gaaaaactgc gtaacaacgc ttacgaaggt cgtgttgttt tcaacccgta a             1011
```

<210> SEQ ID NO 92
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 92

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
              20                  25                  30

Gln Leu Leu Leu Lys Val Asp Ala Val Gly Leu Cys His Ser Asp Leu
          35                  40                  45

His Val Ile Tyr Glu Gly Leu Asp Cys Gly Asp Asn Tyr Val Met Gly
      50                  55                  60

His Glu Ile Ala Gly Thr Val Ala Ala Val Gly Asp Asp Val Ile Asn
65                  70                  75                  80

Tyr Lys Ser Gly Asp Arg Val Ala Cys Val Gly Pro Asn Gly Cys Gly
              85                  90                  95
```

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
            165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
            195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
            245                 250                 255

Ile Met Pro Val Gly Leu Gly Ala Pro Asn Leu Ser Phe Asn Leu Gly
            260                 265                 270

Asp Leu Ala Met Arg Glu Ile Arg Ile Leu Gly Ser Phe Trp Gly Thr
            275                 280                 285

Thr Asn Asp Leu Asp Asp Val Leu Lys Leu Val Ser Glu Gly Lys Val
            290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
            325                 330                 335

<210> SEQ ID NO 93
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 93

```
atgtctatcc cgtcttctca gtatggtttc gtatttaaca acagtctgg  tctgaaactg      60 cgcaacgatc tgccagtaca aagccgaaa  gctggtcaac tgctgctgaa agtagatgca     120
gtaggtctgt gccattctga tctgcacgtt atctacgaag gcctggactg tggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa acgctttcg  gtgactggtt cggtctgggt     360
tatgatggtg gctatcaaca ataccttgctg gtaactcgcc cgcgtaacct gtctcgtatc    420
ccggataacg tatctgctga tgttgctgct gcttctaccg acgctgttct gactccgtac     480
cacgctatca aatggctca  ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg  tgaccaggct aaaaaactgg gtgctgacgc tgtttacgaa     660
accctgccgg aatctatctc tccgggttct ttctctgctt gcttcgactt cgtttctgtt     720
```

```
caggctacct tcgacgtttg ccagaaatac gttgaaccga aaggtgttat catgccggtt    780
ggtctgggtg ctccgaacct gtcttttaac ctgggtgacc tgaatatgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a            1011
```

<210> SEQ ID NO 94
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 94

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Asn Met Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
```

```
                305                 310                 315                 320
Glu Lys Leu Arg Asn Asn Ala Tyr Glu Gly Arg Val Val Phe Asn Pro
                    325                 330                 335
```

<210> SEQ ID NO 95
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 95

```
atgtctatcc cgtcttctca gtatggtttc gtatttaaca acagtctgg tctgaaactg      60
cgcaacgatc tgccagtaca caagccgaaa gctggtcaac tgctgctgaa agtagatgca    120
gtaggtctgt gccactctga tctgcacgtt atctacgaag ctttgacgc gggtgacaac    180
tacgttatgg gtcacgaaat cgctggtacc gttgctgctg ttggtgatga cgttatcaac   240
tacaaagttg gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccgtgctg gtaactcgcc cgcgtaacct gtctcgtatc    420
ccggataacg tatctgctga tgttgctgct gcttctaccg acgctgttct gactccgtac    480
cacgctatca aatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt   720
caggctacct tcgacgtttg ccagaaatac gttgaaccga aggtgtttat catgccggtt   780
ggtctgggtg ctccgaacct gtcttttaac ctgggtgacc tggcgatgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011
```

<210> SEQ ID NO 96
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 96

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Phe Asp Ala Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110
```

```
Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
        260                 265                 270

Asp Leu Ala Met Arg Glu Ile Arg Ile Leu Gly Ser Phe Trp Gly Thr
    275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 97
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 97
atgtctatcc cgtcttctca gtatggtttc gtatttaaca acagtctgg tctgaaactg     60 cgcaacgatc tgccagtaca caagccgaaa gctggtcaac tgctgctgaa agtagatgca    120
gtaggtctgt gccactctga tctgcacgtt atctacgaag cctggactg cggtgacaac    180 tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg gcatcgacaa cgtttgcaaa aacgctttcg gtgactggtt cggtctgggt    360
tatgatggtg gctatcaaca ataccctgctg gtaactcgcc cgcgtaaacct gtctcgtatc    420 ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa agaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780
```

-continued

```
ggtctgggtg ctccgaacct gtcttttaac ctgggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960 gaaaaactgc gtaacaacgc ttacgaaggt cgtgttgttt tcaacccgta a             1011
```

<210> SEQ ID NO 98
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 98

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Gly Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
```

<210> SEQ ID NO 99
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 99

```
atgtctatcc cgtcttctca gtatggtttc gtatttaaca acagtctggt ctgaaactg      60
cgcaacgatc tgccagtaca caagccgaaa gctggtcaac tgctgctgaa agtagatgca     120
gtaggtctgt gccattctga tctgcacgtt atctacgaag gcctggacat aggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg gcatcgacaa cgtttgcaaa aacgctttcc atgactggtt cggtctgggt     360
tatgatggtg gctatcaaca atacctgctg gtaactcgcc gcgtaacct gtctcgtatc      420
ccggataacg tatctgctga tgttgctgct gcttctaccg acgctgttct gactccgtac     480
cacgctatca aatggctca ggtttctccg acctctaaca tcctgctgat cggtgctggt      540
ggtctgggtg gtaacgctat ccaggttgct aaagcattcg gtgctaaagt taccgttctg     600
gacaaaaaaa aagaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt      780
ggtctgggcg ctccgaacct gtcttttaac ctgggtgacc tggctctgcg tgaaatccgt     840
atcctgggtt ctttctgggg taccaccaac gacctggacg acgttctgaa actggtttct     900
gaaggtaaag ttaaaccggt gtacgttct gctaaactga agaactgcc ggaatacatc       960
gaaaaactgc gtaacaacgc ttacgaaggt cgtgttgttt caacccgta a              1011
```

<210> SEQ ID NO 100
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 100

```
Met Ser Ile Pro Ser Ser Gln Tyr Gly Phe Val Phe Asn Lys Gln Ser
1               5                   10                  15
Gly Leu Lys Leu Arg Asn Asp Leu Pro Val His Lys Pro Lys Ala Gly
            20                  25                  30
Gln Leu Leu Leu Lys Val Asp Ala Val Gly Leu Cys His Ser Asp Leu
        35                  40                  45
His Val Ile Tyr Glu Gly Leu Asp Ile Gly Asp Asn Tyr Val Met Gly
    50                  55                  60
His Glu Ile Ala Gly Thr Val Ala Ala Val Gly Asp Asp Val Ile Asn
65                  70                  75                  80
Tyr Lys Val Gly Asp Arg Val Ala Cys Val Gly Pro Asn Gly Cys Gly
                85                  90                  95
Gly Cys Lys Tyr Cys Arg Gly Gly Ile Asp Asn Val Cys Lys Asn Ala
            100                 105                 110
Phe His Asp Trp Phe Gly Leu Gly Tyr Asp Gly Gly Tyr Gln Gln Tyr
        115                 120                 125
```

Leu Leu Val Thr Arg Pro Arg Asn Leu Ser Arg Ile Pro Asp Asn Val
            130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
            195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 101
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 101
atgtctatcc cgtcttctca gtatggtttc gtatttaaca acagtctggt ctgaaactg      60 cgcaacgatc tgccagtaca caagccgaaa gctggtcaac tgctgctgaa agtagatgca   120
gtaggtctgt gccattctga tctgcacgtt atctacgaag gcctggactt aggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg gcatcgacaa cgtttgcaaa aacgctttcc atgactggtt cggtctgggt   360
tatgatggtg gctatcaaca atacctgctg gtaactcgcc gcgtaaccct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt accgttctg    600 gacaaaaaaa aagaagctcg tgaccaggct aaaaaactgg gtgctgacgc tgtttacgaa   660
accctgccgg aatctatctc tccgcgttct ttctctgctt gcttcgactt cgtttctgtt   720
caggctacct cgacgtttg ccagaaatac gttgaaccga aggtgttat catgccggtt     780 ggtctgggcg ctccgaacct gtcttttaac ctgggtgacc tggcgttgcg tgaaatccgt   840
atcctgggtt ctttctgggg taccaccaac gacctggacg acgttctgaa actggtttct   900
gaaggtaaag ttaaaccggt tgtacgttct gctaaactga agaaactgcc ggaatacatc    960
gaaaaactgc gtaacaacgc ttacgaaggt cgtgttgttt tcaacccgta a             1011

<210> SEQ ID NO 102
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 102

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Tyr Glu Gly Leu Asp Leu Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Gly Ile Asp Asn Val Cys Lys Asn Ala
            100                 105                 110

Phe His Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Arg Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 103
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 103

```
atgtctatcc cgtcttctca gtatggtttc gtatttaaca aacagtctgg tctgaaactg      60
cgcaacgatc tgccagtaca caagccgaaa gctggtcaac tgctgctgaa agtagatgca     120
gtaggtctgt gccactctga tctgcacgtt atctcagaag gcctggattt gggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa aacgctttcg gtgactggtt cggtctgggt     360
tatgatggtg gctatcaaca atacctgctg gtaactcgcc cgcgtaacct gtctcgtatc     420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaaactgg gtgctgacgc tgtttacgaa     660
accctgccgg aatctatctc tccgggttct ttctctgctt gcttcgactt cgtttctgtt     720
caggctacct tcgacgtttg ccagaaatac gttgaaccga aggtgttat catgccggtt     780
ggtctgggtg ctccgaacct gtcttttaac ctgcatgacc ttgctctgcg tgaacaccgt     840
atcctgggtt ctttctgggg taccaccaac gacctggacg acgtttttaa actggtttct     900
gaaggtaaag ttaaaccggt tgtacgatct gctaaactga agaactgcc ggaatacatc     960
gaaaaactgc gtaacaacgc ttacgaaggt cgtgttgttt caacccgta a              1011
```

<210> SEQ ID NO 104
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 104

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Ser Glu Gly Leu Asp Leu Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140
```

```
Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
            165                 170                 175

Ile Gly Ala Gly Gly Leu Gly Gly Asn Ala Ile Gln Val Ala Lys Ala
        180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu His
            260                 265                 270

Asp Leu Ala Leu Arg Glu His Arg Ile Leu Gly Ser Phe Trp Gly Thr
        275                 280                 285

Thr Asn Asp Leu Asp Asp Val Phe Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 105
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 105
atgtctatcc cgtcttctca gtatggtttc gtatttaaca acagtctgg tctgaaactg      60 cgcaacgatc tgccagtaca caagccgaaa gctggtcaac tgctgctgaa agtagatgca     120
gtaggtctgt gccactctga tctgcacgtt atcgatgaag cctggatttt gggtgacaac     180
tacgttatgg gtcacgaaat cgctggtacc gttgctgctg ttggtgatga cgttatcaac     240
tacaaagtag gtgaccgtgt agcttgtgtt ggtccgaacg gttgcggtgg ttgcaaatac     300
tgccgtggtg ctatcgacaa cgtttgcaaa acgctttcg gtgactggtt cggtctgggt     360
tatgatggtg gctatcaaca ataccctgctg gtaactcgcc cgcgtaacct gtctcgtatc    420
ccggataacg tatctgctga tgttgctgct gcttctaccg acgctgttct gactccgtac     480
cacgctatca aaatggctca ggtttctccg acctctaaca tcctgctgat cggtgctggt     540
ggtctgggtg gtaacgctat ccaggttgct aaagcattcg gtgctaaagt taccgttctg     600
gacaaaaaaa agaagctcg tgaccaggct aaaaaactgg gtgctgacgc tgtttacgaa      660
accctgccgg aatctatctc tccgggttct ttctctgctt gcttcgactt cgtttctgtt     720
caggctacct tcgacgtttg ccagaaatac gttgaaccga agggtgttat catgccggtt     780
ggtctgggtg ctccgaacct gtcttttaac ctgcatgacc ttgctctgcg tgaaatacgt     840
atcctgggtt ctttctgggg taccaccaac gacctggacg acgttttgaa actggtttct     900
gaaggtaaag ttaaaccggt tgtacgttct gctaaactga aagaactgcc ggaatacatc     960
```
gaaaaactgc gtaacaacgc ttacgaaggt cgtgttgttt tcaacccgta a       1011

<210> SEQ ID NO 106
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 106

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Asp Glu Gly Leu Asp Leu Gly Asp Asn Tyr Val Met Gly
    50                  55                  60

His Glu Ile Ala Gly Thr Val Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Lys Glu Ala Arg Asp
        195                 200                 205

Gln Ala Lys Lys Leu Gly Ala Asp Ala Val Tyr Glu Thr Leu Pro Glu
210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu His
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 107
<211> LENGTH: 1011
<212> TYPE: DNA

<213> ORGANISM: Artificial Sequence
<220> FEATURE:
<223> OTHER INFORMATION: KRED-NADH-102 variant

<400> SEQUENCE: 107

```
atgtctatcc cgtcttctca gtatggtttc gtatttaaca acagtctgg tctgaaactg      60
cgcaacgatc tgccagtaca aagccgaaa gctggtcaac tgctgctgaa agtagatgca    120
gtaggtctgt gccactctga tctgcacgtt atctcagaag cctggatttt gggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780
ggtctgggtg ctccgaacct gtcttttaac ctgcatgacg ttgctctgcg tgaacaccgt    840
atcctgggtt ctttctgggg taccaccaac gacctggacg acgttttcaa actggtttct    900
gaaggtaaag ttaaaccggt tgtacgatct gctaaactga agaactgcc ggaatacatc    960
gaaaaactgc gtaacaacgc ttacgaaggt cgtgttgttt caacccgta a             1011
```

<210> SEQ ID NO 108
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 108

```
Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
                20                  25                  30

Gln Leu Leu Leu Lys Val Asp Ala Val Gly Leu Cys His Ser Asp Leu
            35                  40                  45

His Val Ile Ser Glu Gly Leu Asp Leu Gly Asp Asn Tyr Val Met Gly
        50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                    85                  90                  95

Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
        130                 135                 140

Ser Ala Asp Val Ala Ala Ala Ser Thr Asp Ala Val Leu Thr Pro Tyr
145                 150                 155                 160
```

His Ala Ile Lys Met Ala Gln Val Ser Pro Thr Ser Asn Ile Leu Leu
            165                 170                 175

Ile Gly Ala Gly Gly Leu Gly Gly Asn Ala Ile Gln Val Ala Lys Ala
        180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
            245                 250                 255

Ile Met Pro Val Gly Leu Gly Ala Pro Asn Leu Ser Phe Asn Leu His
            260                 265                 270

Asp Val Ala Leu Arg Glu His Arg Ile Leu Gly Ser Phe Trp Gly Thr
            275                 280                 285

Thr Asn Asp Leu Asp Asp Val Phe Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 109
<211> LENGTH: 1011
<212> TYPE: DNA
<213> ORGANISM: Artificial Sequence
<220> FEATURE:
<223> OTHER INFORMATION: KRED-NADH-102 variant

<400> SEQUENCE: 109
atgtctatcc cgtcttctca gtatggtttc gtatttaaca acagtctgg tctgaaactg        60 cgcaacgatc tgccagtaca caagccgaaa gctggtcaac tgctgctgaa agtagatgca       120
gtaggtctgt gccactctga tctgcacgtt atctcagaag cctggatt gggtgacaac         180 tacgttatgg gtcacgaaat cgctggtacc gttgctgctg ttggtgatga cgttatcaac       240
tacaaagtag gtgaccgtgt agcttgtgtt ggtccgaacg gttgcggtgg ttgcaaatac       300
tgccgtggtg ctatcgacaa cgtttgcaca aacgctttcg gtgactggtt cggtctgggt       360
tatgatggtg gctatcaaca ataccctgctg gtaactcgcc cgcgtaacct gtctcgtatc      420
ccggataacg tatctgctga tgttgctgct gcttctaccg acgctgttct gactccgtac       480
cacgctatca aaatggctca ggtttctccg acctctaaca tcctgctgat cggtgctggt       540
ggtctgggtg gtaacgctat ccaggttgct aaagcattcg gtgctaaagt taccgttctg       600
gacaaaaaaa aagaagctcg tgaccaggct aaaaaactgg gtgctgacgc tgtttacgaa       660
accctgccgg aatctatctc tccgggttct ttctctgctt gcttcgactt cgtttctgtt       720
caggctacct cgacgtttg ccagaaatac gttgaaccga aggtgttat catgccggtt         780 ggtctgggtg ctccgaacct gtcttttaac ctgcatgacc ttgctctgcg tgaaatccgt       840
atcctgggtt ctttctgggg taccaccaac gacctggacg acgttttcaa actggtttct      900
gaaggtaaag ttaaaccggt tgtacgttct gctaaactga agaactgcc ggaatacatc       960 gaaaaactgc gtaacaacgc ttacgaaggt cgtgttgttt tcaacccgta a              1011

```
<210> SEQ ID NO 110
<211> LENGTH: 336
<212> TYPE: PRT
<213> ORGANISM: Artificial Sequence
<220> FEATURE:
<223> OTHER INFORMATION: KRED-NADH-102 variant

<400> SEQUENCE: 110

Met Ser Ile Pro Ser Ser Gln Tyr Gly Phe Val Phe Asn Lys Gln Ser
1               5                   10                  15

Gly Leu Lys Leu Arg Asn Asp Leu Pro Val His Lys Pro Lys Ala Gly
            20                  25                  30

Gln Leu Leu Lys Val Asp Ala Val Gly Leu Cys His Ser Asp Leu
        35                  40                  45

His Val Ile Ser Glu Gly Leu Asp Leu Gly Asp Asn Tyr Val Met Gly
50                  55                  60

His Glu Ile Ala Gly Thr Val Ala Val Gly Asp Val Ile Asn
65                  70                  75                  80

Tyr Lys Val Gly Asp Arg Val Ala Cys Val Pro Asn Gly Cys Gly
                85                  90                  95

Gly Cys Lys Tyr Cys Arg Gly Ala Ile Asp Asn Val Cys Thr Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu His
            260                 265                 270

Asp Leu Ala Leu Arg Glu Ile Arg Ile Leu Gly Ser Phe Trp Gly Thr
        275                 280                 285

Thr Asn Asp Leu Asp Asp Val Phe Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 111
<211> LENGTH: 1032
<212> TYPE: DNA
<213> ORGANISM: Artificial Sequence
<220> FEATURE:
<223> OTHER INFORMATION: KRED-101 variant
```

<400> SEQUENCE: 111

```
atggctaaaa tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc aaaactggct aacctgcaga acgttggga cgctaaatac   180
ccgggtcgtt tcgaaaccgc tgttgttgaa gacatgctga acagggtgc ttacgacgaa   240
gttatcaaag gtgctgctgg tgttgctcac atcgcttccg ttgtttcctt ctccaacaaa   300
tacgacgaag ttgttacccc ggctatcggt ggtaccttga acgctctgcg tgctgctgct   360
gctaccccgt ccgttaaacg tttcgttctg acctcctcca ccgtttccgc tctgattccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccaaa ctacactatt ggcactattt tcgatccgga aactcagtcc   660
ggttccacct ccggttggat gatgtccctg tttaacggcg aggtttcccc ggctctggct   720
ctgatgccac cgcagtacta cgtttccgct gttgatattg cctgctgca cctgggttgc   780
ctggttctgc cacaaatcga acgtcgtcgt gtttacggta cggctggtac tttcgattgg   840
aacaccgttc tggctacctt ccgtaaactg taccgtcca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgctt aa                                                      1032
```

<210> SEQ ID NO 112
<211> LENGTH: 343
<212> TYPE: PRT
<213> ORGANISM: Artificial Sequence
<220> FEATURE:
<223> OTHER INFORMATION: KRED-101 variant

<400> SEQUENCE: 112

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160
```

```
Lys Ala Lys Thr Leu Pro Glu Ser Asp Pro Gln Lys Ser Leu Trp Val
                165                 170                 175
Tyr Ala Ala Ser Lys Thr Glu Ala Glu Leu Ala Ala Trp Lys Phe Met
            180                 185                 190
Asp Glu Asn Lys Pro His Phe Thr Leu Asn Ala Val Leu Pro Asn Tyr
        195                 200                 205
Thr Ile Gly Thr Ile Phe Asp Pro Glu Thr Gln Ser Gly Ser Thr Ser
    210                 215                 220
Gly Trp Met Met Ser Leu Phe Asn Gly Glu Val Ser Pro Ala Leu Ala
225                 230                 235                 240
Leu Met Pro Pro Gln Tyr Tyr Val Ser Ala Val Asp Ile Gly Leu Leu
                245                 250                 255
His Leu Gly Cys Leu Val Leu Pro Gln Ile Glu Arg Arg Val Tyr
            260                 265                 270
Gly Thr Ala Gly Thr Phe Asp Trp Asn Thr Val Leu Ala Thr Phe Arg
        275                 280                 285
Lys Leu Tyr Pro Ser Lys Thr Phe Pro Ala Asp Phe Pro Asp Gln Gly
    290                 295                 300
Gln Asp Leu Ser Lys Phe Asp Thr Ala Pro Ser Leu Glu Ile Leu Lys
305                 310                 315                 320
Ser Leu Gly Arg Pro Gly Trp Arg Ser Ile Glu Glu Ser Ile Lys Asp
                325                 330                 335
Leu Val Gly Ser Glu Thr Ala
            340

<210> SEQ ID NO 113
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 113
atggctaaaa tcgataacgc agttctgccg gaaggttccc tggttctggt taccggtgct      60
aacggtttca ttggttccca cgttgttgaa cagctgctgg aacacggtta caaagttcgt    120
ggtaccgctc gttccgcttc aaactggct  aacctgcaga acgttggga cgctaaatac    180
ccgggtcgtt tcgaaaccgc tgttgttgaa gacatgctga acagggtgc  ttacgacgaa    240
gttatcaaag gtgctgctgg tgttgctcac atcgcttccg ttgtttcctt ctccaacaaa    300
tacgacgaag ttgttacccc ggctatcggt ggtaccttga cgctctgcg  tgctgctgct    360
gctacccgt  ccgttaaacg tttcgttctg acctcctcca ccgtttcggc tctgattccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccaaa ctacactatt ggcactattt tcgatccgga aactcagggc    660
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctacctt ccgtaaactg tacccgtcca aaaccttccc ggctgacttc    900
ccagatcaag gtcaggacct gtctaaattc gacaccgctc cgtcgctgga aattctgaaa    960
tctctgggtc gcccaggttg gcgttccatc gaagaatcca tcaaagacct ggttggttcc   1020
```
gaaaccgctt aa                                                                              1032

<210> SEQ ID NO 114
<211> LENGTH: 343
<212> TYPE: PRT
<213> ORGANISM: Artificial Sequence
<220> FEATURE:
<223> OTHER INFORMATION: KRED-101 variant

<400> SEQUENCE: 114

Met Ala Lys Ile Asp Asn Ala Val Leu Pro Glu Gly Ser Leu Val Leu
1               5                   10                  15

Val Thr Gly Ala Asn Gly Phe Ile Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Gly Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Arg Ala Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 115
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 115

```
atggctaaaa tcgataacgc agttctgccg gaaggttccc tggttctggt taccggtgct      60
aacggtttca ttggttccca cgttgttgaa cagctgctgg aacacggtta caaagttcgt     120
ggtaccgctc gttccgcttc aaactggct aacctgcaga acgttggga cgctaaatac       180
ccgggtcgtt tcgaaaccgc tgttgttgaa gacatgctga acagggtgc ttatgacgaa      240
gttatcaaag gtgctgctgg tgttgctcac atcgcttccg ttgtttcctt ctccaacaaa     300
tacgacgaag ttgttccgcc ggctatcggt ggtaccttga cgctctgcg tgctgctgct     360
gctaccccgt ccgttaaacg tttcgttctg acctcctcca ccgttgcggc tctgattccg     420
aaaccgaacg ttgaaggtat ctacctggac gaaaaatcct ggaacctgga atccatcgac     480
aaagctaaaa ccctgccgga atccgacccg cagaaatccc tgtgggtata cgctgcatcc    540
aagaccgaag ctgaactggc tgcatggaaa tttatggatg agaacaagcc acacttcact     600
ctgaacgctg tactgccaaa ctacactatt ggcactattt tcgatccgga aactcagggc    660
ggttccacct ccggttggat gatgtccctg tttaacggcg aggtttcccc ggctctggct    720
ctgatgccac cgcagtacta cgtttccgct gttgatattg cctgctgca cgtgggtgca    780
ctggttctgc cacaaatcga acgtcgtcgt gtttacggta cggctggtac tttcgattgg    840
aacaccgttc tggctacctt ccgtaaactg tacccgtcca aaaccttccc ggctgacttc    900
ccagatcaag gtcaggacct gtctaaattc gacaccgctc gggcgctgga aattctgaaa   960
tctctgggtc gcccaggttg cgttccatc gaagaatcca tcaaagacct ggttggttcc   1020
gaaaccgctt aa                                                        1032
```

<210> SEQ ID NO 116
<211> LENGTH: 343
<212> TYPE: PRT
<213> ORGANISM: Artificial Sequence
<220> FEATURE:
<223> OTHER INFORMATION: KRED-101 variant

<400> SEQUENCE: 116

```
Met Ala Lys Ile Asp Asn Ala Val Leu Pro Glu Gly Ser Leu Val Leu
1               5                   10                  15

Val Thr Gly Ala Asn Gly Phe Ile Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Pro Pro Ala Ile Gly Gly Thr
            100                 105                 110

Leu Asn Ala Leu Arg Ala Ala Ala Thr Pro Ser Val Lys Arg Phe
        115                 120                 125
```

```
Val Leu Thr Ser Ser Thr Val Ala Ala Leu Ile Pro Lys Pro Asn Val
    130                 135                 140
Glu Gly Ile Tyr Leu Asp Glu Lys Ser Trp Asn Leu Glu Ser Ile Asp
145                 150                 155                 160
Lys Ala Lys Thr Leu Pro Glu Ser Asp Pro Gln Lys Ser Leu Trp Val
                165                 170                 175
Tyr Ala Ala Ser Lys Thr Glu Ala Glu Leu Ala Ala Trp Lys Phe Met
                180                 185                 190
Asp Glu Asn Lys Pro His Phe Thr Leu Asn Ala Val Leu Pro Asn Tyr
            195                 200                 205
Thr Ile Gly Thr Ile Phe Asp Pro Glu Thr Gln Gly Gly Ser Thr Ser
210                 215                 220
Gly Trp Met Met Ser Leu Phe Asn Gly Glu Val Ser Pro Ala Leu Ala
225                 230                 235                 240
Leu Met Pro Pro Gln Tyr Tyr Val Ser Ala Val Asp Ile Gly Leu Leu
                245                 250                 255
His Val Gly Ala Leu Val Leu Pro Gln Ile Glu Arg Arg Val Tyr
            260                 265                 270
Gly Thr Ala Gly Thr Phe Asp Trp Asn Thr Val Leu Ala Thr Phe Arg
            275                 280                 285
Lys Leu Tyr Pro Ser Lys Thr Phe Pro Ala Asp Phe Pro Asp Gln Gly
290                 295                 300
Gln Asp Leu Ser Lys Phe Asp Thr Ala Arg Ala Leu Glu Ile Leu Lys
305                 310                 315                 320
Ser Leu Gly Arg Pro Gly Trp Arg Ser Ile Glu Glu Ser Ile Lys Asp
                325                 330                 335
Leu Val Gly Ser Glu Thr Ala
            340

<210> SEQ ID NO 117
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 117
atggctaaaa tcgataacgc agttctgccg gaaggttccc tggttctggt taccggtgct    60
aacggtttca ttggttccca cgttgttgaa cagctgctgg aacacggtta caaagttcgt   120
ggtaccgctc gttccgcttc caaactggct aacctgcaga acgttgggga cgctaaatac   180
ccgggtcgtt tcgaaaccgc tgttgttgaa gacatgctga acagggtgc ttatgacgaa    240 gttatcaaag tgctgctggt gttgctcac atcgcttccg ttgtttcctt ctccaacaaa    300
tacgacgaag ttgttccgcc ggctatcggt ggtaccttga cgctctgcg tgctgctgct    360 gctaccccgt ccgttaaacg tttcgttctg acctcctcca ccgtttccgc tctgattccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccaaa ctacactatt ggcactattt tagatccgga aactcagtcc    660
ggttccacct ccggttggat gatgtccctg tttaacggcg aggtttcccc ggctctggct    720
ctgatgccac cgcagtacta cgtttccgtg gttgatattg gcctgctgca cgtgggtgca    780
```

```
ctggttctgc cacaaatcga acgtcgtcgt gtttacggta cggctggtac tttcgattgg      840
aacaccgttc tggctacctt ccgtaaactg tacccgtcca aaaccttccc ggctgacttc      900
ccagatcaag gtcaggacct gtctaaattc gacaccgctc gggcgctgga aattctgaaa      960
tctctgggtc gcccaggttg gcgttccatc gaagaatcca tcaaagacct ggttggttcc     1020
gaaaccgctt aa                                                          1032
```

<210> SEQ ID NO 118
<211> LENGTH: 343
<212> TYPE: PRT
<213> ORGANISM: Artificial Sequence
<220> FEATURE:
<223> OTHER INFORMATION: KRED-101 variant

<400> SEQUENCE: 118

```
Met Ala Lys Ile Asp Asn Ala Val Leu Pro Glu Gly Ser Leu Val Leu
1               5                   10                  15

Val Thr Gly Ala Asn Gly Phe Ile Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Leu Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Val Asp Ile Gly Leu Leu
                245                 250                 255

His Val Gly Ala Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Arg Ala Leu Glu Ile Leu Lys
305                 310                 315                 320
```

Ser Leu Gly Arg Pro Gly Trp Arg Ser Ile Glu Glu Ser Ile Lys Asp
            325                 330                 335

Leu Val Gly Ser Glu Thr Ala
            340

<210> SEQ ID NO 119
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 119

```
atggctaaaa tcgataacgc agttcttccg gaaggttccc tggttctggt taccggtgct      60
aacggtttcg ttggttccca cgttgttgaa cagctgctgg aacacggtta caaagttcgt     120
ggtaccgctc gttccgcttc aaactggct aatctgcaga acgttggga cgctaaatac       180
ccgggtcgtt tcgaaaccgc tgttgttgaa gacatgctga acagggtgc ttacgacgaa      240
gttatcaaag gtgctgctgg tgttgctcac atcgcttccg ttgtttcctt ctccaacaaa     300
tacgacgaag ttgttacccc ggctatcggt ggtaccttga cgctctgcg tgctgctgct     360
gctgagccgt ccgttaaacg tttcgttctg acctcctcca ccgtttccgc tctgattccg     420
aaaccgaacg ttgaaggtat ctacctggac gaaaaatcct ggaacctgga tccgttgac    480
aaagctaaaa ccctgccgga atccgacccg cagaaatccc tgtgggtata cgctgcatcc     540
aagaccgaag ctgaactggc tgcatggaaa tttatggatg agaacaagcc acacttcact     600
ctgaacgctg tactgccaaa ctacactatt ggcactattt tcgatccgga aactcagtcc     660
ggttccacct ccgggttggat gatgtccctg tttaacggcg aggtttcccc ggctctggct    720
ctgatgccac cgcagtacta cgtttccgct gtagatattg gcctgctgca cctgggttgc    780
ctggttctgc cacaaatcga acgtcgtcgt gtttacggta cggctggtac tttcgattgg    840
aacaccgttc tggctaccctt ccgtaaactg tacccgtcca aaaccttccc ggctgacttc   900
ccagatcaag gtcaggacct gtctaaattc gacaccgctc cgtccgaaga acttctgaaa    960
tctctgggtc gcccaggttg gcgttccatc gaagaatcca tcaaagacct ggttggttcc   1020
gaaaccgctt aa                                                       1032
```

<210> SEQ ID NO 120
<211> LENGTH: 343
<212> TYPE: PRT
<213> ORGANISM: Artificial Sequence
<220> FEATURE:
<223> OTHER INFORMATION: KRED-101 variant

<400> SEQUENCE: 120

Met Ala Lys Ile Asp Asn Ala Val Leu Pro Glu Gly Ser Leu Val Leu
1               5                  10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser

```
                    85                  90                  95
Phe Ser Asn Lys Tyr Asp Glu Val Val Thr Pro Ala Ile Gly Gly Thr
            100                 105                 110

Leu Asn Ala Leu Arg Ala Ala Ala Glu Pro Ser Val Lys Arg Phe
        115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Val Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Asn Tyr
            195                 200                 205

Thr Ile Gly Thr Ile Phe Asp Pro Glu Thr Gln Ser Gly Ser Thr Ser
        210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Glu Glu Leu Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 121
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 121
atggctaaaa tcgataacgc agttcttccg gaaggttccc tggttctggt taccggtgct      60
aacggtttcg ttggttccca cgttgttgaa cagctgctgg aacacggtta caaagttcgt     120
ggtaccgctc gttccgcttc caaactggct aacctgcaga acgttggga cgctaaatac      180 ccgggtcgtt tcgaaaccgc tgttgttgaa gacatgctga acagggtgc ttacgacgaa      240 gttatcaaag gtgctgctgg tgttgctcac atcgcttccg ttgtttcctt ctccaacaaa     300
tacgacgaag ttgttacccc ggctatcggt ggtaccttga cgctctgcg tgctgctgct     360 gctaccccgt ccgttaaacg tttcgttctg acctcctcca ccgtttccgc tctgattccg     420
aaaccgaacg ttgaaggtat ctacctggac gaaaaatcct ggaacctgga atccgttgac     480
aaagctaaaa ccctgccgga atccgacccg cagaaatccc tgtgggtata cgctgcatcc     540
aagaccgaag ctgaactggc tgcatggaaa tttatggatg agaacaagcc acacttcact     600
```

```
ctgaacgctg tactgccaaa ctacaccatt ggcactattt tcgatccgga aactcagtcc      660
ggttccacct ccggttggat gatgtccctg tttaacggcg aggtttcccc ggctctggct      720
ctgatgccac cgcagtacta cgtttccgct caggatattg gcctgctgca cctgggttgc      780
ctggttctgc cacaaatcga acgtcgtcgt gttttggta cggctggtcc gttcgattgg       840
aacaccgttc tggctacctt ccgtaaactg tacccgtcca aaaccttccc ggctgacttc      900
ccagatcaag gtcaggacct gtctaaattc gacaccgctc gtccgaaga acttctgaaa       960 tctctgggtc gcccaggttg gcgttccctt gaagaatcca tcaaagacct ggttggttcc      1020
gaaaccgctt aa                                                          1032
```

<210> SEQ ID NO 122
<211> LENGTH: 343
<212> TYPE: PRT
<213> ORGANISM: Artificial Sequence
<220> FEATURE:
<223> OTHER INFORMATION: KRED-101 variant

<400> SEQUENCE: 122

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Thr Pro Ala Ile Gly Gly Thr
            100                 105                 110

Leu Asn Ala Leu Arg Ala Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Val Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Gln Asp Ile Gly Leu Leu
                245                 250                 255

His Leu Gly Cys Leu Val Leu Pro Gln Ile Glu Arg Arg Val Phe
            260                 265                 270

Gly Thr Ala Gly Pro Phe Asp Trp Asn Thr Val Leu Ala Thr Phe Arg
```

```
            275                 280                 285
Lys Leu Tyr Pro Ser Lys Thr Phe Pro Ala Asp Phe Pro Asp Gln Gly
        290                 295                 300

Gln Asp Leu Ser Lys Phe Asp Thr Ala Pro Ser Glu Glu Leu Leu Lys
305                 310                 315                 320

Ser Leu Gly Arg Pro Gly Trp Arg Ser Leu Glu Glu Ser Ile Lys Asp
                325                 330                 335

Leu Val Gly Ser Glu Thr Ala
            340

<210> SEQ ID NO 123
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 123
atggctaaaa tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc aaactggct aacctgcaga acgttggga cgctaaatac       180 ccgggtcgtt tcgaaaccgc tgttgttgaa gacatgctga acagggtgc ttacgacgaa      240 gttatcaaag gtgctgctgg tgttgctcac atcgcttccg ttgtttcctt ctccaacaaa     300
tacgacgaag ttgttacccc ggctatcggt ggtaccttga acgctctgcg tgctgctgct     360
gctaccccgt ccgttaaacg tttcgttctg acctcctcca ccgtttccgc tctgattccg     420
aaaccgaacg ttgaaggtat ctacctggac gaaaaatcct ggaacctgga tccatcgac      480 aaagctaaaa ccctgccgga atccgacccg cagaaatccc tgtgggtata cgctgcatcc     540
aagaccgaag ctgaactggc tgcatggaaa tttatggatg agaacaagcc acacttcact     600
ctgaacgctg tactgccagg gtacactatt ggcactattt tcgatccgga aactcagtcc     660
ggttccacct ccggttggat gatgtccctg tttaacggcg aggtttcccc ggctctggct     720
ctgatgccac gcagtacta cgtttccgct gttgatattg gcctgctgca cctgggttgc      780
ctggttctgc cacaaatcga acgtcgtcgt gtttacggta cggctggtac tttcgattgg     840
aacaccgttc tggctacctt ccgtaaactg taccgtcca aaaccttccc ggctgacttc      900
ccagatcaag gtcaggacct gtctaaattc gacaccgctc cgtccctgga aattctgaaa     960
tctctgggtc gcccaggttg gcgttccatc gaagaatcca tcaaagacct ggttggttcc    1020
gaaaccgctt aa                                                        1032

<210> SEQ ID NO 124
<211> LENGTH: 343
<212> TYPE: PRT
<213> ORGANISM: Artificial Sequence
<220> FEATURE:
<223> OTHER INFORMATION: KRED-101 variant

<400> SEQUENCE: 124

Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45
```

Leu Ala Asn Leu Gln Lys Arg Trp Asp Ala Lys Tyr Pro Gly Arg Phe
 50                  55                  60

Glu Thr Ala Val Val Glu Asp Met Leu Lys Gln Gly Ala Tyr Asp Glu
 65                  70                  75                  80

Val Ile Lys Gly Ala Ala Gly Val Ala His Ile Ala Ser Val Val Ser
                 85                  90                  95

Phe Ser Asn Lys Tyr Asp Glu Val Val Thr Pro Ala Ile Gly Gly Thr
                100                 105                 110

Leu Asn Ala Leu Arg Ala Ala Ala Thr Pro Ser Val Lys Arg Phe
            115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Gly Tyr
            195                 200                 205

Thr Ile Gly Thr Ile Phe Asp Pro Glu Thr Gln Ser Gly Ser Thr Ser
210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
                290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 125
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 125
atggctaaaa tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac   180 ccgggtcgtt tcgaaaccgc tgttgttgaa gacatgctga acagggtgc ttacgacgaa   240 gttatcaaag gtgctgctgg tgttgctcac atcgcttccg ttgtttcctt ctccaacaaa   300
tacgacgaag ttgttacccc ggctatcggt ggtaccttga cgctctgcg tgctgctgct   360

```
gctacccegt ccgttaaacg tttcgttctg acctcctcca ccgtttccgc tctgattccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccagg gtacactatt ggcactattt tcgatccgga aactcagtcc    660
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctaccct tccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc    1020
gaaaccgctt aa                                                        1032
```

<210> SEQ ID NO 126  
<211> LENGTH: 343  
<212> TYPE: PRT  
<213> ORGANISM: Artificial Sequence  
<220> FEATURE:  
<223> OTHER INFORMATION: KRED-101 variant

<400> SEQUENCE: 126

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
                20                  25                  30

Leu Glu His Gly Tyr Lys Val Arg Gly Thr Ala Arg Ser Ala Ser Lys
            35                  40                  45

Leu Ala Asn Leu Gln Lys Arg Trp Asp Ala Lys Tyr Pro Gly Arg Phe
        50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
                100                 105                 110

Leu Asn Ala Leu Arg Ala Ala Ala Thr Pro Ser Val Lys Arg Phe
            115                 120                 125

Val Leu Thr Ser Ser Thr Val Ser Ala Leu Ile Pro Lys Pro Asn Val
        130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Gly Tyr
            195                 200                 205

Thr Ile Gly Thr Ile Phe Asp Pro Glu Thr Gln Ser Gly Ser Thr Ser
        210                 215                 220

Gly Trp Met Met Ser Leu Phe Asn Gly Glu Val Ser Pro Ala Leu Ala
225                 230                 235                 240
```

```
Leu Met Pro Pro Gln Tyr Tyr Val Ser Ala Val Asp Ile Gly Leu Leu
            245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
            290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340
```

<210> SEQ ID NO 127
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 127

```
atggctaaaa tcgataacgc agttctgccg gaaggttccc tggttctggt taccggtgct      60
aacggtttcg ttggttccca cgttgttgaa cagctgctgg aacacggtta caaagttcgt    120
ggtaccgctc gttccgcttc caaactggct aacctgcaga acgttggga cgctaaatac     180
ccgggtcgtt tcgaaaccgc tgttgttgaa gacatgctga acagggtgc ttacgacgaa     240
gttatcaaag gtgctgctgg tgttgctcac atcgcttccg ttgtttcctt ctccaacaaa    300
tacgacgaag ttgttacccc ggctatcggt ggtaccttga acgctctgcg tgctgctgct    360
gctaccccgt ccgttaaacg tttcgttctg acctcctcca ccttttccgc tctgattccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccaaa ctacactatt ggcactattt tcgatccgga aactcagtcc    660
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctacctt ccgtaaactg tacccgtcca aaaccttccc ggctgacttc    900
ccagatcaag tcaggacct gtctaaattc gacaccgctc cgtccctgga aattttgaaa    960
tctctgggtc gcccaggttg gcgttccatc gaagaatcca tcaaagacct ggttggttcc   1020
gaaaccgctt aa                                                      1032
```

<210> SEQ ID NO 128
<211> LENGTH: 343
<212> TYPE: PRT
<213> ORGANISM: Artificial Sequence
<220> FEATURE:
<223> OTHER INFORMATION: KRED-101 variant

<400> SEQUENCE: 128

```
Met Ala Lys Ile Asp Asn Ala Val Leu Pro Glu Gly Ser Leu Val Leu
1               5                   10                  15
```

Val Thr Gly Ala Asn Gly Phe Gly Ser His Val Glu Gln Leu
            20                  25                  30

Leu Glu His Gly Tyr Lys Val Arg Gly Thr Ala Arg Ser Ala Ser Lys
 35                  40                  45

Leu Ala Asn Leu Gln Lys Arg Trp Asp Ala Lys Tyr Pro Gly Arg Phe
 50                  55                  60

Glu Thr Ala Val Val Glu Asp Met Leu Lys Gln Gly Ala Tyr Asp Glu
 65                  70                  75                  80

Val Ile Lys Gly Ala Ala Gly Val Ala His Ile Ala Ser Val Ser
                 85                  90                  95

Phe Ser Asn Lys Tyr Asp Glu Val Thr Pro Ala Ile Gly Gly Thr
                100                 105                 110

Leu Asn Ala Leu Arg Ala Ala Ala Thr Pro Ser Val Lys Arg Phe
                115                 120                 125

Val Leu Thr Ser Ser Thr Phe Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Asn Tyr
                195                 200                 205

Thr Ile Gly Thr Ile Phe Asp Pro Glu Thr Gln Ser Gly Ser Thr Ser
210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
                260                 265                 270

Gly Thr Ala Gly Thr Phe Asp Trp Asn Thr Val Leu Ala Thr Phe Arg
                275                 280                 285

Lys Leu Tyr Pro Ser Lys Thr Phe Pro Ala Asp Phe Pro Asp Gln Gly
290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
                340

<210> SEQ ID NO 129
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 129
atggctaaaa tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc caaactggct aacctgcaga acgttggga cgctaaatac     180

-continued

```
ccgggtcgtt tcgaaaccgc tgttgttgaa gacatgctga aacagggtgc ttacgacgaa    240
gttatcaaag gtgctgctgg tgttgctcac atcgcttccg ttgtttcctt ctccaacaaa    300
tacgacgaag ttgttacccc ggctatcggt ggtaccttga acgctctgcg tgctgctgct    360
gctaccccgt ccgttaaacg tttcgttctg acctcctcca ccttttccgc tctgattccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccaaa ctacactatt ggcactattt tcgatccgga aactcagtcc    660
ggttccacct ccggttggat gatgtccctg tttaacggcg aggtttcccc ggctctggct    720
ctgatgccac cgcagtacta cgtttccgct gttgatattg gctgctgca cctgggttgc    780 ctggttctgc cacaaatcga acgtcgtcgt gtttacggta cggctggtac tttcgattgg    840
aacaccgttc tggctacctt ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc    1020
gaaaccgctt aa    1032
```

<210> SEQ ID NO 130
<211> LENGTH: 343
<212> TYPE: PRT
<213> ORGANISM: Artificial Sequence
<220> FEATURE:
<223> OTHER INFORMATION: KRED-101 variant

<400> SEQUENCE: 130

```
Met Ala Lys Ile Asp Asn Ala Val Leu Pro Glu Gly Ser Leu Val Leu
  1               5                  10                  15

Val Thr Gly Ala Asn Gly Phe Val Gly Ser His Val Val Glu Gln Leu
             20                  25                  30

Leu Glu His Gly Tyr Lys Val Arg Gly Thr Ala Arg Ser Ala Ser Lys
         35                  40                  45

Leu Ala Asn Leu Gln Lys Arg Trp Asp Ala Lys Tyr Pro Gly Arg Phe
     50                  55                  60

Glu Thr Ala Val Val Glu Asp Met Leu Lys Gln Gly Ala Tyr Asp Glu
 65                  70                  75                  80

Val Ile Lys Gly Ala Ala Gly Val Ala His Ile Ala Ser Val Val Ser
                 85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205
```

```
Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
            290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 131
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 131
atggctaaaa tcgataacgc agttctgccg gaaggttccc tggttctggt taccggtgct     60
aacggtttcg ttggttccca cgttgttgaa cagctgctgg aacacggtta caaagttcgt    120
ggtaccgctc gttccgcttc aaactggct aacctgcaga acgttggga cgctaaatac      180 ccgggtcgtt tcgaaaccgc tgttgttgaa gacatgctga acagggtgc ttacgacgaa     240 gttatcaaag gtgctgctgg tgttgctcac atcgcttccg ttgtttcctt ctccaacaaa    300
tacgacgaag ttgttacccc ggctatcggt ggtaccttga cgctctgcg tgctgctgct    360 gctacccgt ccgttaaacg tttcgttctg acctcctcca ccgtttccgc tctggttccg    420
aaaccgaacg ttgaaggtat ctacctggac gaaaaatcct ggaacctgga atccatcgac    480
aaagctaaaa ccctgccgga atccgaccccg cagaaatccc tgtgggtata cgctgcatcc    540
aagaccgaag ctgaactggc tgcatggaaa tttatggatg agaacaagcc acacttcact    600
ctgaacgctg tactgccatc gtacactatt ggcactattt tcgatccgga aactcagtcc    660
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctacctt ccgtaaactg tacccgtcca aaaccttccc ggctgacttc    900
ccagatcaag gtcaggacct gtctaaattc gacaccgctc cgtccctgga aattttgaaa    960
tctttgggtc gcccaggttg gcgttccatc gaagaatcca tcaaagacct ggttggttcc   1020
gaaaccgctt aa                                                        1032

<210> SEQ ID NO 132
<211> LENGTH: 343
<212> TYPE: PRT
<213> ORGANISM: Artificial Sequence
```

<220> FEATURE:
<223> OTHER INFORMATION: KRED-101 variant

<400> SEQUENCE: 132

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Ser Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340
```

<210> SEQ ID NO 133
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 133

```
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac   180
ccgggtcgtt tcgaaaccgc tgttgttgaa gacatgctga acagggtgc ttacgacgaa   240
gttatcaaag gtgctgctgg tgttgctcac atcgcttccg ttacatcctt ctccaacaaa   300
tacgacgaag ttgttacccc ggctatcggt ggtaccttga cgctctgcg tgctgctgct   360
gctaccccgt ccgttaaacg tttcgttctg acctcctcca ccgtttccgc tctgattccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccagg gtacactatt ggcactattt tcgatccgga aactcagtcc   660
ggttccacct ccggttggat gatgtccctg tttaacggcg aggtttcccc ggccctggct   720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctaccct tccgtaaactg tacccgtcca aaaccttccc ggctgacttc   900
ccagatcaag gtcaggacct gtctaaattc gacaccgctc gtccctgga aattctgaaa   960
tctctgggtc gcccaggttg gcgttccatc gaagaatcca tcaaagacct ggttggttcc  1020
gaaaccgctt aa                                                      1032
```

<210> SEQ ID NO 134
<211> LENGTH: 343
<212> TYPE: PRT
<213> ORGANISM: Artificial Sequence
<220> FEATURE:
<223> OTHER INFORMATION: KRED-101 variant

<400> SEQUENCE: 134

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
```

```
                    165                 170                 175
Tyr Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Gly Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
            245                 250                 255

His Leu Gly Cys Leu Val Leu Pro Gln Ile Glu Arg Arg Val Tyr
        260                 265                 270

Gly Thr Ala Gly Thr Phe Asp Trp Asn Thr Val Leu Ala Thr Phe Arg
    275                 280                 285

Lys Leu Tyr Pro Ser Lys Thr Phe Pro Ala Asp Phe Pro Asp Gln Gly
        290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Ser Ile Lys Asp
            325                 330                 335

Leu Val Gly Ser Glu Thr Ala
            340

<210> SEQ ID NO 135
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 135
atggcaaaga tcgataacgc agttctgccg gaaggttccc tggttctggt taccggtgct      60
aacggtttca ttggttccca cgttgttgaa cagctgctgg aacacggtta caaagttcgt     120
ggtaccgctc gttccgcttc caaactggct aacctgcaga acgttgggac gctaaatac      180
ccgggtcgtt tcgaaaccgc tgttgttgaa gacatgctga acagggtgc ttacgacgaa      240
gttatcaaag gtgctgctgg tgttgctcac atcgcttccg ttacatcctt ctccaacaaa     300
tacgacgaag ttgttacccc ggctatcggt ggtaccttga cgctctgcg tgctgctgct     360
gctaccccgt ccgttaaacg tttcgttctg acctcctcca ccgtttccgc tctgattccg     420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccagg atacactatt ggcactattt tcgatccgga aactcagtcc    660
ggttccacct ccggttggat gacgtccctg tttaacggcg aggtttcccc ggccctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctaccct ccgtaaactg tacccgtcca aaaccttccc ggctgacttc    900
ccagatcaag tcaggacct gtctaaattc gacaccgctc cgtccctgga aattctgaaa    960
tctctgggtc gcccaggttg gcgttccatc gaagaatcca tcaaagacct ggttggttcc  1020
```
gaaaccgctt aa                                                          1032

<210> SEQ ID NO 136
<211> LENGTH: 343
<212> TYPE: PRT
<213> ORGANISM: Artificial Sequence
<220> FEATURE:
<223> OTHER INFORMATION: KRED-101 variant

<400> SEQUENCE: 136

```
Met Ala Lys Ile Asp Asn Ala Val Leu Pro Glu Gly Ser Leu Val Leu
1               5                   10                  15

Val Thr Gly Ala Asn Gly Phe Ile Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Gly Tyr
        195                 200                 205

Thr Ile Gly Thr Ile Phe Asp Pro Glu Thr Gln Ser Gly Ser Thr Ser
    210                 215                 220

Gly Trp Met Thr Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Ser Ile Lys Asp
                325                 330                 335

Leu Val Gly Ser Glu Thr Ala
            340
```

<210> SEQ ID NO 137
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 137

```
atggcaaaga tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc aaactggct aacctgcaga acgttggga cgctaaatac       180
ccgggtcgtt tcgaaaccgc tgttgttgaa gacatgctga acagggtgc ttacgacgaa      240
gttatcaaag gtgctgctgg tgttgctcac atcgcttccg ttacatcctt ctccaacaaa    300
tacgacgaag ttgttacccc ggctatcggt ggtaccttga cgctctgcg tgctgctgct     360
gctaccccgt ccgttaaacg tttcgttctg acctcctcca cctttccgc tctggttccg     420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc    540
aagaccgaag ctgaactggc tgcatggaaa tttatggatg agaacaagcc acacttcact    600
ctgaacgctg tactgccaaa ctacactatt ggcactattt tcgatccgga aactcagtcc   660
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg   840
aacaccgttc tggctaccct ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgctt aa                                                         1032
```

<210> SEQ ID NO 138
<211> LENGTH: 343
<212> TYPE: PRT
<213> ORGANISM: Artificial Sequence
<220> FEATURE:
<223> OTHER INFORMATION: KRED-101 variant

<400> SEQUENCE: 138

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125
```

| Val | Leu | Thr | Ser | Ser | Thr | Phe | Ser | Ala | Leu | Val | Pro | Lys | Pro | Asn | Val |
| 130 | | | | | 135 | | | | | 140 | | | | | |

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Asn Tyr
                195                 200                 205

Thr Ile Gly Thr Ile Phe Asp Pro Glu Thr Gln Ser Gly Ser Thr Ser
210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
                260                 265                 270

Gly Thr Ala Gly Thr Phe Asp Trp Asn Thr Val Leu Ala Thr Phe Arg
                275                 280                 285

Lys Leu Tyr Pro Ser Lys Thr Phe Pro Ala Asp Phe Pro Asp Gln Gly
290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
                340

<210> SEQ ID NO 139
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 139
atggcataca tcgataacgc agttctgccg gaaggttccc tggttctggt taccggtgct      60
aacggtttcg ttggttccca cgttgttgaa cagctgctgg aacacggtta caaagttcgt    120
ggtaccgctc gttccgcttc caaactggct aacctgcaga acgttggga cgctaaatac     180 ccgggtcgtt tcgaaaccgc tgttgttgaa gacatgctga acagggtgc ttacgacgaa     240 gttatcaaag gtgctgctgg tgttgctcac atcgcttccg ttacatcctt ctccaacaaa    300
tacgacgaag ttgttacccc ggctatcggt ggtaccttga cgctctgcg tgctgctgct     360 gctaccccgt ccgttaaacg tttcgttctg acctcctcca ccgtttccgc tctgattccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccagg gtacactatt ggcactattt tcgatccgga aactcagtcc    660
ggttccacct ccggttggat gatgtccctg tttaacggcg aggtttcccc ggccctggct    720
ctgatgccac cgcagtacta cgtttccgct gttgatattg gctgctgca cctgggttgc    780 ctggttctgc cacaaatcga acgtcgtcgt gtttacggta cggctggtac tttcgattgg    840

```
aacaccgttc tggctacctt ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgctt aa                                                       1032
```

<210> SEQ ID NO 140
<211> LENGTH: 343
<212> TYPE: PRT
<213> ORGANISM: Artificial Sequence
<220> FEATURE:
<223> OTHER INFORMATION: KRED-101 variant

<400> SEQUENCE: 140

```
Met Ala Tyr Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Gly Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320
```

Ser Leu Gly Arg Pro Gly Trp Arg Ser Ile Glu Glu Ser Ile Lys Asp
            325                 330                 335

Leu Val Gly Ser Glu Thr Ala
            340

<210> SEQ ID NO 141
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 141

| | | | | | | |
|---|---|---|---|---|---|---|
| atggcataca | tcgataacgc | agttctgccg | gaaggttccc | tggttctggt | taccggtgct | 60 |
| aacggtttcg | ttggttccca | cgttgttgaa | cagctgctgg | aacacggtta | caaagttcgt | 120 |
| ggtaccgctc | gttccgcttc | caaactggct | aacctgcaga | aacgttggga | cgctaaatac | 180 |
| ccgggtcgtt | tcgaaaccgc | tgttgttgaa | gacatgctga | aacagggtgc | ttacgacgaa | 240 |
| gttatcaaag | gtgctgctgg | tgttgctcac | atcgcttccg | ttacatcctt | ctccaacaaa | 300 |
| tacgacgaag | ttgttacccc | ggctatcggt | ggtaccttga | cgctctgcg | tgctgctgct | 360 |
| gctaccccgt | ccgttaaacg | tttcgttctg | acctcctcca | ccgtttccgc | tctgattccg | 420 |
| aaaccgaacg | ttgaaggtat | ctacctggac | gaaaaatcct | ggaacctgga | atccatcgac | 480 |
| aaagctaaaa | ccctgccgga | atccgacccg | cagaaatccc | tgtgggtata | cgctgcatcc | 540 |
| aagaccgaag | ctgaactggc | tgcatggaaa | tttatggatg | agaacaagcc | acacttcact | 600 |
| ctgaacgctg | tactgccagg | atacactatt | ggcactattt | tcgatccgga | aactcagtcc | 660 |
| ggttccacct | ccggttggat | gacgtccctg | tttaacggcg | aggtttcccc | ggccctggct | 720 |
| ctgatgccac | cgcagtacta | cgtttccgct | gttgatattg | cctgctgca | cctgggttgc | 780 |
| ctggttctgc | cacaaatcga | acgtcgtcgt | gtttacggta | cggctggtac | tttcgattgg | 840 |
| aacaccgttc | tggctacctt | ccgtaaactg | taccgtccca | aaaccttccc | ggctgacttc | 900 |
| ccagatcaag | gtcaggacct | gtctaaattc | gacaccgctc | ggtccctgga | aattctgaaa | 960 |
| tctctgggtc | gcccaggttg | gcgttccatc | gaagaatcca | tcaaagacct | ggttggttcc | 1020 |
| gaaaccgctt | aa | | | | | 1032 |

<210> SEQ ID NO 142
<211> LENGTH: 343
<212> TYPE: PRT
<213> ORGANISM: Artificial Sequence
<220> FEATURE:
<223> OTHER INFORMATION: KRED-101 variant

<400> SEQUENCE: 142

Met Ala Tyr Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
            85                  90                  95

```
Phe Ser Asn Lys Tyr Asp Glu Val Val Thr Pro Ala Ile Gly Gly Thr
                100                 105                 110

Leu Asn Ala Leu Arg Ala Ala Ala Thr Pro Ser Val Lys Arg Phe
            115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Gly Tyr
                195                 200                 205

Thr Ile Gly Thr Ile Phe Asp Pro Glu Thr Gln Ser Gly Ser Thr Ser
        210                 215                 220

Gly Trp Met Thr Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
                260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
                290                 295                 300

Gln Asp Leu Ser Lys Phe Asp Thr Ala Arg Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 143
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 143
atgactaaga tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc aaactggct aacctgcaga acgttggga cgctaaatac       180
ccgggtcgtt cgaaaccgc tgttgttgaa gacatgctga acagggtgc ttacgacgaa       240
gttatcaaag gtgctgctgg tgttgctcac atcgcttccg ttgtttcctt ctccaacaaa    300
cctgacgaag ttgttacccc ggctatcggt ggtaccttga cgctctgcg tgctgctgct     360
gctaccccgt ccgttaaacg tttcgttctg acctcctcca ccgttccgc tctgattccg      420
aaaccgaacg ttgaaggtat ctacctggac gaaaaatcct ggaacctgga atccatcgac    480
aaagctaaaa ccctgccgga atccgacccg cagaaatccc tgtgggtata cgctctgtcc   540
aagatggaag ctgaactggc tgcatggaaa tttatggatg agaacaagcc acacttcact    600
```

-continued

```
ctgaacgctg tactgccagg gtacactatt ggcactattt tcgatccgga aactcagtcc    660
ggttccacct ccggttggat gaggtccctg tttaacggcg aggtttcccc gttgctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacgaagttc tggctacctt ccgtaaactg tacccgtcca aaaccttccc ggctgacttc    900
ccagatcaag gtcaggacct gtctaaattc gacaccgctc gtccctgga aattctgaaa    960 tctctgggtc gcccaggttg gcgttccatc gaagaatcca tcaaagacct ggttggttcc   1020
gaaaccgctt aa                                                      1032
```

<210> SEQ ID NO 144
<211> LENGTH: 343
<212> TYPE: PRT
<213> ORGANISM: Artificial Sequence
<220> FEATURE:
<223> OTHER INFORMATION: KRED-101 variant

<400> SEQUENCE: 144

```
Met Thr Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Pro Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Leu Ser Lys Met Glu Ala Glu Leu Ala Ala Trp Lys Phe Met
            180                 185                 190

Asp Glu Asn Lys Pro His Phe Thr Leu Asn Ala Val Leu Pro Gly Tyr
        195                 200                 205

Thr Ile Gly Thr Ile Phe Asp Pro Glu Thr Gln Ser Gly Ser Thr Ser
    210                 215                 220

Gly Trp Met Arg Ser Leu Phe Asn Gly Glu Val Ser Pro Leu Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Glu Val Leu Ala Thr Phe Arg
        275                 280                 285
```

```
Lys Leu Tyr Pro Ser Lys Thr Phe Pro Ala Asp Phe Pro Asp Gln Gly
        290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 145
<211> LENGTH: 1032
<212> TYPE: DNA
<213> ORGANISM: Artificial Sequence
<220> FEATURE:
<223> OTHER INFORMATION: KRED-101 variant

<400> SEQUENCE: 145
atggctaaaa tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc caaactggct aacctgcaga acgttggga cgctaaatac      180 ccgggtcgtt tcgaaaccgc tgttgttgaa gacatgctga acagggtgc ttacgacgaa      240 gttatcaaag gtgctgctgg tgttgctcac atcgcttccg ttgtttcctt ctccaacaaa     300
tacgacgaag ttgttacccc ggctatcggt ggtaccttga acgctctgcg tgctgctgct     360
gctaccccgt ccgttaaacg tttcgttctg acctcctcca ccgtttccgc tctgattccg     420
aagccgaacg ttgaaggtat ctacctggac gaaaagtcct ggaacctgga atccgttgac     480
aaagctaaaa ccctgccgga atccgacccg cagaaatccc tgtgggtata cgctgcatcc     540
aagaccgaag ctgaactggc tgcatggaaa tttatggatg agaacaagcc acacttcact     600
ctgaacgctg tactgccagg gtacactatt ggcactattt tcgatccgga aactcagtcc     660
ggttccacct ccggttggat gctgtccctg tttaacggcg aggtttcgcc ggctctggct     720
ctgatgccac gcagtacta cgtttccgct gttgatattg ccctgctgca cctgggttgc     780
ctggttctgc cacaaatcga acgtcgtcgt gtttacggta cggctggtac tttcgattgg     840
aacaccgttc tggctacctt ccgtaaactg tacccgtcca aaaccttccc ggctgacttc     900
ccagatcaag gtcaggacct gtctcaattc gacaccgctc cgtccctgga aattctgaaa     960
tctctgggtc gcccaggttg gcgttccctt gaagaatcca tcaaagacct ggttggttcc    1020
gaaaccgctt aa                                                        1032

<210> SEQ ID NO 146
<211> LENGTH: 343
<212> TYPE: PRT
<213> ORGANISM: Artificial Sequence
<220> FEATURE:
<223> OTHER INFORMATION: KRED-101 variant

<400> SEQUENCE: 146

Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
```

```
                50             55              60
Glu Thr Ala Val Val Glu Asp Met Leu Lys Gln Gly Ala Tyr Asp Glu
 65                  70                  75                  80

Val Ile Lys Gly Ala Ala Gly Val Ala His Ile Ala Ser Val Val Ser
                 85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Ala Thr Pro Ser Val Lys Arg Phe
            115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Val Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Gly Tyr
            195                 200                 205

Thr Ile Gly Thr Ile Phe Asp Pro Glu Thr Gln Ser Gly Ser Thr Ser
210                 215                 220

Gly Trp Met Leu Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
290                 295                 300

Gln Asp Leu Ser Gln Phe Asp Thr Ala Pro Ser Leu Glu Ile Leu Lys
305                 310                 315                 320

Ser Leu Gly Arg Pro Gly Trp Arg Ser Leu Glu Ser Ile Lys Asp
                325                 330                 335

Leu Val Gly Ser Glu Thr Ala
            340
```

<210> SEQ ID NO 147
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 147

| | | |
|---|---|---|
| atggcaaaga tcgataacgc agttctgccg gaaggttccc tggttctggt taccggtgct | 60 |
| aacggtttca ttggttccca cgttgttgaa cagctgctgg aacacggtta caagttcgt | 120 |
| ggtaccgtgc gttccgctga aaaaaatgct aacctgcaga acgttggga cgctaaatac | 180 |
| ccgggtcgtt tcgaaaccgt ggaagttcca gacatgctga acagggtgc ttacgacgaa | 240 |
| gttatcaaag gtgctgctgg tgttgctcac gttgcttccg taacatcctt ctccaacaaa | 300 |
| tacgacgaag ttgttacccc ggctatcggt ggtaccttga acgctctgcg tgctgctgct | 360 |
| gctaccccgt ccgttaaacg tttcgttctg acctcctcca cctttccgc tctggttccg | 420 |

```
aaaccgaacg ttgaaggtat ctacctggac gaaaaatcct ggaacctgga atccatcgac    480
aaagctaaaa ccctgccgga atccgacccg cagaaatccc tgtgggtata cgctgcgtcc    540
aagaccgaag ctgaactggc tgcatggaaa tttatggatg agaacaagcc acacttcact    600
ctgaacgctg tactgccaaa ctacactatt ggcactattt tcgatccgga aacccagggc    660
gggtccacct ccggttggat gatgtccctg tttaacggcg aggtttcccc ggctctggct    720
ctgatgccac cgcagtacta cgtttccgct gttgatattg gctgctgca cctgggttgc    780 ctggttctgc cacaaatcga acgtcgtcgt gtttacggta cggctggtac tttcgattgg    840
aacaccgttc tggctaccct ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                            1029
```

<210> SEQ ID NO 148
<211> LENGTH: 343
<212> TYPE: PRT
<213> ORGANISM: Artificial Sequence
<220> FEATURE:
<223> OTHER INFORMATION: KRED-101 variant

<400> SEQUENCE: 148

```
Met Ala Lys Ile Asp Asn Ala Val Leu Pro Glu Gly Ser Leu Val Leu
1               5                   10                  15

Val Thr Gly Ala Asn Gly Phe Ile Gly Ser His Val Val Glu Gln Leu
            20                  25                  30

Leu Glu His Gly Tyr Lys Val Arg Gly Thr Val Arg Ser Ala Glu Lys
        35                  40                  45

Asn Ala Asn Leu Gln Lys Arg Trp Asp Ala Lys Tyr Pro Gly Arg Phe
    50                  55                  60

Glu Thr Val Glu Val Pro Asp Met Leu Lys Gln Gly Ala Tyr Asp Glu
65                  70                  75                  80

Val Ile Lys Gly Ala Ala Gly Val Ala His Val Ala Ser Val Thr Ser
            85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
            165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Gly Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
```

```
                     245                 250                 255
His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
        290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 149
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 149
atggcaaaga tcgataacgc agttctgccg gaaggttccc tggttctggt taccggtgct      60
aacggtttca ttggttccca cgttgttgaa cagctgctgg aacacggtta caaagttcgt     120
ggtaccgcgc gttccgcttc aaaacttgct aacctgcaga acgttggga cgctaaatac      180
ccgggtcgtt tcgaaccgc ggaagttgag acatgctga acagggtgc ttacgacgaa        240
gttatcaaag gtgctgctgg tgttgctcac gttgcttccg taacatcctt ctccaacaaa     300
tacgacgaag ttgttacccc ggctatcggt ggtaccttga cgctctgcg tgctgctgct     360
gctaccccgt ccgttaaacg tttcgttctg acctcctcca ccttttccgc tctggttccg     420
aaaccgaacg ttgaaggtat ctacctggac gaaaaatcct ggaacctgga atccatcgac     480
aaagctaaaa ccctgccgga atccgacccg cagaaatccc tgtgggtata cgctgcgtcc     540
aagaccgaag ctgaactggc tgcatggaaa tttatggatg agaacaagcc acacttcact     600
ctgaacgctg tactgccaaa ctacactatt ggcactattt tcgatccgga aaaccagggc     660
gggtccacct ccggttggat gatgtccctg tttaacggcg aggtttcccc ggctctggct     720
ctgatgccac cgcagtacta cgtttccgct gttgatattg gcctgctgca cctgggttgc     780
ctggttctgc cacaaatcga acgtcgtcgt gtttacggta cggctggtac tttcgattgg     840
aacaccgttc tggctaccct ccgtaaactg tacccgtcca aaccttccc ggctgacttc      900
ccagatcaag tcaggacct gtctaaattc gacaccgctc cgtccctgga aattctgaaa     960
tctctgggtc gcccaggttg gcgttccatc gaagaatcca tcaaagacct ggttggttcc    1020
gaaaccgct                                                            1029

<210> SEQ ID NO 150
<211> LENGTH: 343
<212> TYPE: PRT
<213> ORGANISM: Artificial Sequence
<220> FEATURE:
<223> OTHER INFORMATION: KRED-101 variant

<400> SEQUENCE: 150

Met Ala Lys Ile Asp Asn Ala Val Leu Pro Glu Gly Ser Leu Val Leu
1               5                   10                  15
```

Val Thr Gly Ala Asn Gly Phe Ile Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Glu Val Glu Asp Met Leu Lys Gln Gly Ala Tyr Asp Glu
65                  70                  75                  80

Val Ile Lys Gly Ala Ala Gly Val Ala His Val Ala Ser Val Thr Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Asn Gln Gly Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 151
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 151
atggcaaaga tcgataacgc agttctgccg gaaggttccc tggttctggt taccggtgct      60
aacggtttcg ttggttccca cgttgttgaa cagctgctgg aacacggtta caaagttcgt    120
ggtaccgctc gttccgcttc caaactggct aacctgcaga acgttgggga cgctaaatac    180

-continued

```
ccgggtcgtt tcgaaaccgc tgttgttgaa gacatgctta agcaaggtgc tttttgacgaa      240 gttatcaaag gtgctgctgg tgttgctcac atcgcttccg ttacatcctt ttccaacaaa      300
tacgacgagg ttgttaccgg tgcgatcggt ggtaccttga acgctctgcg tgctgctgct      360
gctaccccgt ccgttaaacg tttcgttctg acctcctcca ccttttccgc tctggttccg      420
aaaccgaacg ttgaaggtat ctacctggac gaaaaatcct ggaacctgga atccatcgac      480
aaagctaaaa ccctgccgga atccgacccg cagaaatccc tgtgggtata cgctgcgtcc      540
aagaccgaag ctgaactggc tgcatggaaa tttatggatg agaacaagcc acacttcact      600
ctgaacgctg tactgccaaa ctacactatt ggcactatct ttgatccgga aactcagtcc      660
ggttccacct ccggttggat gatgtccctg tttaacggcg aggtttcccc ggctctggct      720
ctgatgccac cgcagtacta cgtttccgct gttgatattg gcctgctgca cctgggttgc      780
ctggttctgc cacaaatcga acgtcgtcgt gtttacggta cggctggtac tttcgattgg      840
aacaccgttc tggctacctt ccgtaaactg tacccgtcca aaaccttccc ggctgacttc      900
ccagatcaag gtcaggacct gtctaaattc gacaccgctc cgtccctgga aattctgaaa      960
tctctgggtc gcccaggttg gcgttccatc gaagaatcca tcaaagacct ggttggttcc     1020
gaaaccgct                                                              1029
```

<210> SEQ ID NO 152
<211> LENGTH: 343
<212> TYPE: PRT
<213> ORGANISM: Artificial Sequence
<220> FEATURE:
<223> OTHER INFORMATION: KRED-101 variant

<400> SEQUENCE: 152

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Phe Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Gly Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205
```

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
        290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 153
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 153

| | |
|---|---|
| atggcaaaga tcgataacgc agttctgccg aaggttccc tggttctggt taccggtgct | 60 |
| aacggtttcg ttggttccca cgttgttgaa cagctgctgg aacacggtta caaagttcgt | 120 |
| ggtaccgctc gttccgcttc caaactggct aacctgcaga acgttggga cgctaaatac | 180 |
| ccgggtcgtt tcgaaaccgc tgttgttgaa gacatgcttg cagaaggtgc ttttgacgaa | 240 |
| gttatcaaag gtgctgctgg tgttgctcac atcgcttccg ttacatcctt ctccaacaaa | 300 |
| tacgacgagg ttgttacccc cgtgatcggt ggtaccttga cgctctgcg tgctgctgct | 360 |
| gctaccccgt ccgttaaacg tttcgttctg acctcctcca cctttccgc tctggttccg | 420 |
| aaaccgaacg ttgaaggtat ctacctggac gaaaaatcct ggaacctgga atccatcgac | 480 |
| aaagctaaaa ccctgccgga atccgacccg cagaaatccc tgtgggtata cgctgcgtcc | 540 |
| aagaccgaag ctgaactggc tgcatggaaa tttatggatg agaacaagcc acacttcact | 600 |
| ctgaacgctg tactgccaaa ctacactatt ggcactattt tcgatccgga aactcagtcc | 660 |
| ggttccacct cgggttggat gatgtccctg tttaacggcg aggtttcccc ggctctggct | 720 |
| ctgatgccac cgcaatacta cgtttccgct gttgatattg gctgctgca cctgggttgc | 780 |
| ctggttctgc cacaaatcga acgtcgtcgt gtttacggta cggctggtac tttcgattgg | 840 |
| aacaccgttc tggctacctt ccgtaaactg tacccgtcca aaaccttccc ggctgacttc | 900 |
| ccagatcaag gtcaggacct gtctaaattc gacaccgctc cgtccctgga aattctgaaa | 960 |
| tctctgggtc gcccaggttg gcgttccatc gaagaatcca tcaaagacct ggttggttcc | 1020 |
| gaaaccgct | 1029 |

<210> SEQ ID NO 154
<211> LENGTH: 343
<212> TYPE: PRT
<213> ORGANISM: Artificial Sequence
<220> FEATURE:

<223> OTHER INFORMATION: KRED-101 variant

<400> SEQUENCE: 154

| | | | | | | | | | | | | | | | |
|---|---|---|---|---|---|---|---|---|---|---|---|---|---|---|---|
| Met | Ala | Lys | Ile | Asp | Asn | Ala | Val | Leu | Pro | Glu | Gly | Ser | Leu | Val | Leu |
| 1 | | | | 5 | | | | | 10 | | | | | 15 | |
| Val | Thr | Gly | Ala | Asn | Gly | Phe | Val | Gly | Ser | His | Val | Val | Glu | Gln | Leu |
| | | | 20 | | | | | 25 | | | | | 30 | | |
| Leu | Glu | His | Gly | Tyr | Lys | Val | Arg | Gly | Thr | Ala | Arg | Ser | Ala | Ser | Lys |
| | | 35 | | | | | 40 | | | | | 45 | | | |
| Leu | Ala | Asn | Leu | Gln | Lys | Arg | Trp | Asp | Ala | Lys | Tyr | Pro | Gly | Arg | Phe |
| 50 | | | | | 55 | | | | | 60 | | | | | |
| Glu | Thr | Ala | Val | Val | Glu | Asp | Met | Leu | Ala | Gly | Ala | Phe | Asp | Glu | |
| 65 | | | | | 70 | | | | 75 | | | | | 80 | |
| Val | Ile | Lys | Gly | Ala | Ala | Gly | Val | Ala | His | Ile | Ala | Ser | Val | Thr | Ser |
| | | | | 85 | | | | | 90 | | | | | 95 | |
| Phe | Ser | Asn | Lys | Tyr | Asp | Glu | Val | Val | Thr | Pro | Val | Ile | Gly | Gly | Thr |
| | | | 100 | | | | | 105 | | | | | 110 | | |
| Leu | Asn | Ala | Leu | Arg | Ala | Ala | Ala | Thr | Pro | Ser | Val | Lys | Arg | Phe | |
| | | 115 | | | | | 120 | | | | | 125 | | | |
| Val | Leu | Thr | Ser | Ser | Thr | Phe | Ser | Ala | Leu | Val | Pro | Lys | Pro | Asn | Val |
| | 130 | | | | | 135 | | | | | 140 | | | | |
| Glu | Gly | Ile | Tyr | Leu | Asp | Glu | Lys | Ser | Trp | Asn | Leu | Glu | Ser | Ile | Asp |
| 145 | | | | | 150 | | | | | 155 | | | | | 160 |
| Lys | Ala | Lys | Thr | Leu | Pro | Glu | Ser | Asp | Pro | Gln | Lys | Ser | Leu | Trp | Val |
| | | | | 165 | | | | | 170 | | | | | 175 | |
| Tyr | Ala | Ala | Ser | Lys | Thr | Glu | Ala | Glu | Leu | Ala | Ala | Trp | Lys | Phe | Met |
| | | | 180 | | | | | 185 | | | | | 190 | | |
| Asp | Glu | Asn | Lys | Pro | His | Phe | Thr | Leu | Asn | Ala | Val | Leu | Pro | Asn | Tyr |
| | | | 195 | | | | | 200 | | | | | 205 | | |
| Thr | Ile | Gly | Thr | Ile | Phe | Asp | Pro | Glu | Thr | Gln | Ser | Gly | Ser | Thr | Ser |
| | 210 | | | | | 215 | | | | | 220 | | | | |
| Gly | Trp | Met | Met | Ser | Leu | Phe | Asn | Gly | Glu | Val | Ser | Pro | Ala | Leu | Ala |
| 225 | | | | | 230 | | | | | 235 | | | | | 240 |
| Leu | Met | Pro | Pro | Gln | Tyr | Tyr | Val | Ser | Ala | Val | Asp | Ile | Gly | Leu | Leu |
| | | | | 245 | | | | | 250 | | | | | 255 | |
| His | Leu | Gly | Cys | Leu | Val | Leu | Pro | Gln | Ile | Glu | Arg | Arg | Val | Tyr | |
| | | | 260 | | | | | 265 | | | | | 270 | | |
| Gly | Thr | Ala | Gly | Thr | Phe | Asp | Trp | Asn | Thr | Val | Leu | Ala | Thr | Phe | Arg |
| | | | 275 | | | | | 280 | | | | | 285 | | |
| Lys | Leu | Tyr | Pro | Ser | Lys | Thr | Phe | Pro | Ala | Asp | Phe | Pro | Asp | Gln | Gly |
| | | | | 290 | | | | | 295 | | | | | 300 | |
| Gln | Asp | Leu | Ser | Lys | Phe | Asp | Thr | Ala | Pro | Ser | Leu | Glu | Ile | Leu | Lys |
| 305 | | | | | 310 | | | | | 315 | | | | | 320 |
| Ser | Leu | Gly | Arg | Pro | Gly | Trp | Arg | Ser | Ile | Glu | Glu | Ser | Ile | Lys | Asp |
| | | | | 325 | | | | | 330 | | | | | 335 | |
| Leu | Val | Gly | Ser | Glu | Thr | Ala | | | | | | | | | |
| | | | | 340 | | | | | | | | | | | |

<210> SEQ ID NO 155
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 155

```
atggcaaaga tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc aaactggct aacctgcaga acgttggga cgctaaatac       180 ccgggtcgtt tcgaaaccgc tgttgttgaa gacatgctta aggaaggtgc ttttgacgaa     240
gttatcaaag gtgctgctgg tgttgctcac atcgcttccg ttacatcctt ctcccccaaa     300
tacgacgagg ttgttacccc cgtgatcggt ggtaccttga acgctctgcg tgctgctgct     360
gctaccccgt ccgttaaacg tttcgttctg acctcctcca cctttccgc tctggttccg      420 aaaccgaacg ttgaaggtat ctacctggac gaaaaatcct ggaacctgga atccatcgac     480
aaagctaaaa ccctgccgga atccgacccg cagaaatccc tgtgggtata cgctgcgtcc     540
aagaccgaag ctgaactggc tgcatggaaa tttatggatg agaacaagcc acacttcact    600
ctgaacgctg tactgccaaa ctacactatt ggcactatct tttctccgga aactcagtcc    660
ggttccaccg cggggttggat gatgtccctg tttaacggcg aggtttcccc ggctctggct   720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctaccct ccgtaaactg tacccgtcca aaaccttccc ggctgacttc    900
ccagatcaag tcaggacct gtctaaattc gacaccgctc cgtccctgga aattctgaaa    960
tctctgggtc gcccaggttg gcgttccatc gaagaatcca tcaaagacct ggttggttcc  1020
gaaaccgct                                                           1029
```

<210> SEQ ID NO 156
<211> LENGTH: 343
<212> TYPE: PRT
<213> ORGANISM: Artificial Sequence
<220> FEATURE:
<223> OTHER INFORMATION: KRED-101 variant

<400> SEQUENCE: 156

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Glu Gly Ala Phe Asp Glu
65                  70                  75                  80

Val Ile Lys Gly Ala Ala Gly Val Ala His Ile Ala Ser Val Thr Ser
                85                  90                  95

Phe Ser Pro Lys Tyr Asp Glu Val Val Thr Pro Val Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175
```

```
Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Ser Pro Glu Thr Gln Ser Gly Ser Thr Ala
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340
```

<210> SEQ ID NO 157
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 157

```
atggcaaaga tcgataacgc agttctgccg gaaggttccc tggttctggt tacctcggct      60
aacggtttcg ttggttccca cgttgttgaa cagctgctgg aacacggtta caaagttcgt     120
ggtaccgctc gttccgcttc caaactggct aacctgcaga acgttgggga cgctaaatac     180
ccgggtcgtt cgaaaccgc tgttgttgaa gacatgctga acagggtgc ttacgacgaa      240
gttatcaaag gtgctgctgg tgttgctcac atcgcttccg ttacatcctt ctccaacaaa     300
tacgacgaag ttgttacccc ggctatcggt ggtaccttga cgctctgcg tgctgctgct     360
gctaccccgt ccgttaaacg tttcgttctg acctcctcca ccttttccgc tctggttccg     420
aaaccgaacg ttgaaggtat ctacctggac gaaaaatcct ggaacctgga atccatcgac     480
aaagctaaaa ccctgccgga atccgacccg cagaaatccc tgtgggtata cgctgcgtcc     540
aagaccgaag ctgaactggc tgcatggaaa tttatggatg agaacaagcc acacttcact     600
ctgaacgctg tactgccaaa ctacactatt ggcactattt tcgatccgga aactcagtcc     660
ggttccacct ccggttggat gatgtccctg tttaacggcg aggtttcccc ggctctggct     720
ctgatgccac cgcagtacta cgtttccgct gttgatattg gcctgctgca cctgggttgc     780
ctggttctgc cacaaatcga acgtcgtcgt gtttacggta cggctggtac tttcgattgg     840
aacaccgttc tggctaccct ccgtaaactg taccgtcca aaccttccc ggctgacttc      900
ccagatcaag gtcaggacct gtctaaattc gacaccgctc cgtccctgga aattctgaaa     960
tctctgggtc gccaggttg gcgttccatc gaagaatcca tcaaagacct ggttggttcc    1020
gaaaccgct                                                          1029
```

```
<210> SEQ ID NO 158
<211> LENGTH: 343
<212> TYPE: PRT
<213> ORGANISM: Artificial Sequence
<220> FEATURE:
<223> OTHER INFORMATION: KRED-101 variant

<400> SEQUENCE: 158

Met Ala Lys Ile Asp Asn Ala Val Leu Pro Glu Gly Ser Leu Val Leu
1               5                   10                  15

Val Thr Ser Ala Asn Gly Phe Val Gly Ser His Val Val Glu Gln Leu
                20                  25                  30

Leu Glu His Gly Tyr Lys Val Arg Gly Thr Ala Arg Ser Ala Ser Lys
            35                  40                  45

Leu Ala Asn Leu Gln Lys Arg Trp Asp Ala Lys Tyr Pro Gly Arg Phe
        50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
                100                 105                 110

Leu Asn Ala Leu Arg Ala Ala Ala Thr Pro Ser Val Lys Arg Phe
            115                 120                 125

Val Leu Thr Ser Ser Thr Phe Ser Ala Leu Val Pro Lys Pro Asn Val
        130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 159
```

<211> LENGTH: 1029
<212> TYPE: DNA
<213> ORGANISM: Artificial Sequence
<220> FEATURE:
<223> OTHER INFORMATION: KRED-101 variant

<400> SEQUENCE: 159

```
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc aaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttccg tttgttcctt ctccaacaaa   300
tacgacgaag ttgttacccc ggctatcggt ggtaccttga acgctctgcg tgctgctgct   360
gctaccccgt ccgttaaacg tttcgttctg acctcctcca ccttttccgc tctggttccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactattt tcgatccgga aactcagtcc   660
ggttccacct ccggttggat gatgtccctg tttaacggcg aggtttcccc ggctctggct   720
ctgatgccac cgcagtacta cgtttccgct gttgatattg cctgctgca cctgggttgc    780
ctggttctgc cacaaatcga acgtcgtcgt gtttacggta cggctggtac tttcgattgg   840
aacaccgttc tggctaccct ccgtaaactg tacccgtcca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgct                                                          1029
```

<210> SEQ ID NO 160
<211> LENGTH: 343
<212> TYPE: PRT
<213> ORGANISM: Artificial Sequence
<220> FEATURE:
<223> OTHER INFORMATION: KRED-101 variant

<400> SEQUENCE: 160

```
Met Ala Lys Ile Asp Asn Ala Val Leu Pro Glu Gly Ser Leu Val Leu
  1               5                  10                  15

Val Thr Gly Ala Asn Gly Phe Val Gly Ser His Val Val Glu Gln Leu
             20                  25                  30

Leu Glu His Gly Tyr Lys Val Arg Gly Thr Ala Arg Ser Ala Ser Lys
         35                  40                  45

Leu Ala Asn Leu Gln Lys Arg Trp Asp Ala Lys Tyr Pro Gly Arg Phe
     50                  55                  60

Glu Thr Ala Val Val Glu Asp Met Leu Lys Gln Gly Ala Tyr Asp Glu
 65                  70                  75                  80

Val Ile Lys Gly Ala Ala Gly Val Ala His Ile Ala Ser Val Cys Ser
                 85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
```

```
                130                 135                 140
Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Asn Tyr
                195                 200                 205

Thr Ile Gly Thr Ile Phe Asp Pro Glu Thr Gln Ser Gly Ser Thr Ser
                210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
                260                 265                 270

Gly Thr Ala Gly Thr Phe Asp Trp Asn Thr Val Leu Ala Thr Phe Arg
                275                 280                 285

Lys Leu Tyr Pro Ser Lys Thr Phe Pro Ala Asp Phe Pro Asp Gln Gly
                290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
                340

<210> SEQ ID NO 161
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 161
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc aaactggct aacctgcaga acgttggga cgctaaatac   180
ccgggtcgtt cgaaaccgc tgttgttgaa gacatgctga acagggtgc ttacgacgaa   240
gttatcaaag gtgctgctgg tgttgctcac atcgcttccg ttacagggtt ctccaacaaa   300
tacgacgaag ttgttacccc ggctatcggt ggtaccttga cgctctgcg tgctgctgct   360
gctaccccgt ccgttaaacg tttcgttctg acctcctcca ccttttccgc tctggttccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactattt tcgatccgga aactcagtcc   660
ggttccacct ccggttggat gatgtccctg tttaacggcg aggtttcccc ggctctggct   720
ctgatgccac cgcagtacta cgtttccgct gttgatattg gctgctgca cctgggttgc   780
ctggttctgc cacaaatcga acgtcgtcgt gtttacggta cggctggtac tttcgattgg   840
```

```
aacaccgttc tggctacctt ccgtaaactg tacccgtcca aaaccttccc ggctgacttc      900
ccagatcaag gtcaggacct gtctaaattc gacaccgctc cgtccctgga aattctgaaa      960
tctctgggtc gcccaggttg gcgttccatc gaagaatcca tcaaagacct ggttggttcc     1020
gaaaccgct                                                              1029
```

<210> SEQ ID NO 162
<211> LENGTH: 343
<212> TYPE: PRT
<213> ORGANISM: Artificial Sequence
<220> FEATURE:
<223> OTHER INFORMATION: KRED-101 variant

<400> SEQUENCE: 162

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Gly
                85                  90                  95

Phe Ser Asn Lys Tyr Asp Glu Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
```

325                 330                 335
Leu Val Gly Ser Glu Thr Ala
            340

<210> SEQ ID NO 163
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 163
atggcaaaga tcgataacgc agttctgccg gaaggttccc tggttctggt tacctcggct      60
aacggtttcg ttggttccca cgttgttgaa cagctgctgg aacacggtta caaagttcgt     120
ggtaccgctc gttccgcttc aaaactggct aacctgcaga acgttggga cgctaaatac      180 ccgggtcgtt tcgaaaccgc tgttgttgaa gacatgctga acagggtgc ttacgacgaa      240 gttatcaaag gtgctgctgg tgttgctcac atcgcttccg ttacatcctt ctccaacaaa     300
tacgacgaag ttgttacccc ggctatcggt ggtaccttga acgctctgcg tgctgctgct     360
gctaccccgt ccgttaaacg tttcgttctg acctcctcca ccttttccgc tctggttccg     420
aaaccgaacg ttgaaggtat ctacctggac gaaaaatcct ggaacctgga atccatcgac     480
aaagctaaaa ccctgccgga atccgacccg cagaaatccc tgtgggtata cgctgcgtcc     540
aagaccgaag ctgaactggc tgcatggaaa tttatggatg agaacaagcc acacttcact     600
ctgaacgctg tactgccaaa ctacactatt ggcactattt tcgatccgga aactcagtcc     660
ggttccacct ccggttggat gatgtccctg tttaacggcg aggtttcccc ggctctggct     720
ctgatgccac gcagtacta cgtttccgct gttgatattg gcctgctgca cctgggttgc     780
ctggttctgc cacaaatcga acgtcgtcgt gtttacggta cggctggtac tttcgattgg     840
aacaccgttc tggctacctt ccgtaaactg tacccgtcca aaccttccc ggctgacttc      900 ccagatcaag gtcaggacct gtctaaattc gacaccgctc cgtccctgga aattctgaaa     960
tctctgggtc gcccaggttg gcgttccatc gaagaatcca tcaaagacct ggttggttcc    1020
gaaaccgct                                                           1029

<210> SEQ ID NO 164
<211> LENGTH: 343
<212> TYPE: PRT
<213> ORGANISM: Artificial Sequence
<220> FEATURE:
<223> OTHER INFORMATION: KRED-101 variant

<400> SEQUENCE: 164

Met Ala Lys Ile Asp Asn Ala Val Leu Pro Glu Gly Ser Leu Val Leu
1               5                   10                  15

Val Thr Ser Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
                100                 105                 110

Leu Asn Ala Leu Arg Ala Ala Ala Thr Pro Ser Val Lys Arg Phe
            115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
                180                 185                 190

Asp Glu Asn Lys Pro His Phe Thr Leu Asn Ala Val Leu Pro Asn Tyr
                195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
                260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
            290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 165
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 165
atggcaaaga tcgataacgc agttctgccg aaggttccc tggttctggt taccggtgct     60
aacggtttcg ttggttccca cgttgttgaa cagctgctgg aacacggtta caaagttcgt    120
ggtaccgctc gttccgcttc caaactggct aacctgcaga acgttggga cgctaaatac     180 ccgggtcgtt tcgaaaccgc tgttgttgaa gaccagctga acagggtgc ttacgacgaa     240 gttatcaaag gtgctgctgg tgttgctcac atcgcttccg ttacatcctt ctccaacaaa    300
tacgacgaag ttgttacccc ggctatcggt ggtaccttga cgctctgcg tgctgctgct    360 gctaccccgt ccgttaaacg tttcgttctg acctcctcca ccttttccgc tctggttccg    420
aaaccgaacg ttgaaggtat ctacctggac gaaaaatcct ggaacctgga atccatcgac    480
aaagctaaaa ccctgccgga atccgacccg cagaaatccc tgtgggtata cgctgcgtcc    540
aagaccgaag ctgaactggc tgcatggaaa tttatggatg agaacaagcc acacttcact    600
ctgaacgctg tactgccaaa ctacactatt ggcactattt tcgatccgga aactcagtcc    660

```
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctaccct ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                            1029
```

<210> SEQ ID NO 166
<211> LENGTH: 343
<212> TYPE: PRT
<213> ORGANISM: Artificial Sequence
<220> FEATURE:
<223> OTHER INFORMATION: KRED-101 variant

<400> SEQUENCE: 166

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Gln Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285
```

```
Lys Leu Tyr Pro Ser Lys Thr Phe Pro Ala Asp Phe Pro Asp Gln Gly
    290                 295                 300
Gln Asp Leu Ser Lys Phe Asp Thr Ala Pro Ser Leu Glu Ile Leu Lys
305                 310                 315                 320
Ser Leu Gly Arg Pro Gly Trp Arg Ser Ile Glu Glu Ser Ile Lys Asp
                325                 330                 335
Leu Val Gly Ser Glu Thr Ala
            340

<210> SEQ ID NO 167
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 167
atggcaaaga tcgataacgc agttctgccg aaggttccc tggttctggt taccggtgct      60
aacggtttcg ttggttccca cgttgttgaa cagctgctgg aacacggtta caaagttcgt     120
ggtaccgctc gttccgcttc aaaactggct aacctgcaga acgttggga cgctaaatac      180
ccgggtcgtt tcgaaacctg ggttgttgaa acatgctga acagggtgc ttacgacgaa       240
gttatcaaag gtgctgctgg tgttgctcac atcgcttccg ttacatcctt ctccaacaaa     300
tacgacgaag ttgttacccc ggctatcggt ggtaccttga cgctctgcg tgctgctgct     360
gctaccccgt ccgttaaacg tttcgttctg acctcctcca ccttttccgc tctggttccg     420
aaaccgaacg ttgaaggtat ctacctggac gaaaaatcct ggaacctgga atccatcgac     480
aaagctaaaa ccctgccgga atccgacccg cagaaatccc tgtgggtata cgctgcgtcc     540
aagaccgaag ctgaactggc tgcatggaaa tttatggatg agaacaagcc acacttcact    600
ctgaacgctg tactgccaaa ctacactatt ggcactattt tcgatccgga actcagtcc     660
ggttccacct ccggttggat gatgtccctg tttaacggcg aggtttcccc ggctctggct    720
ctgatgccac cgcagtacta cgtttccgct gttgatattg gcctgctgca cctgggttgc    780
ctggttctgc acaaaatcga acgtcgtcgt gtttacggta cggctggtac tttcgattgg    840
aacaccgttc tggctaccct ccgtaaactg tacccgtcca aaaccttccc ggctgacttc    900
ccagatcaag tcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                            1029

<210> SEQ ID NO 168
<211> LENGTH: 343
<212> TYPE: PRT
<213> ORGANISM: Artificial Sequence
<220> FEATURE:
<223> OTHER INFORMATION: KRED-101 variant

<400> SEQUENCE: 168

Met Ala Lys Ile Asp Asn Ala Val Leu Pro Glu Gly Ser Leu Val Leu
1               5                   10                  15
Val Thr Gly Ala Asn Gly Phe Val Gly Ser His Val Val Glu Gln Leu
            20                  25                  30
Leu Glu His Gly Tyr Lys Val Arg Gly Thr Ala Arg Ser Ala Ser Lys
        35                  40                  45
Leu Ala Asn Leu Gln Lys Arg Trp Asp Ala Lys Tyr Pro Gly Arg Phe
    50                  55                  60
```

Glu Thr Trp Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
            85                  90                  95

Phe Ser Asn Lys Tyr Asp Glu Val Thr Pro Ala Ile Gly Gly Thr
        100                 105                 110

Leu Asn Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
            165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
        290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 169
<211> LENGTH: 1029
<212> TYPE: DNA
<213> ORGANISM: Artificial Sequence
<220> FEATURE:
<223> OTHER INFORMATION: KRED-101 variant

<400> SEQUENCE: 169
atggcaaaga tcgataacgc agttctgccg gaaggttccc tggttctggt taccggtgct      60
aacggtttcg ttggttccca cgttgttgaa cagctgctgg aacacggtta caaagttcgt    120
ggtaccgctc gttccgcttc caaactggct aacctgcaga acgttgggga cgctaaatac    180
ccgggtcgtt cgaaaccgc tgttgttgaa gacatgctga acagggtgc ttacgacgaa    240 gttatcaaag gtgctgctgg tgttgctcac atcgcttccg ttacatcctt ctccaacaaa    300
tacgacgaag ttgttacccc ggctatcggt ggtaccttgg ttgctctgcg tgctgctgct    360 gctacccgt ccgttaaacg tttcgttctg acctcctcca ccttttccgc tctggttccg    420

```
aaaccgaacg ttgaaggtat ctacctggac gaaaaatcct ggaacctgga atccatcgac     480
aaagctaaaa ccctgccgga atccgacccg cagaaatccc tgtgggtata cgctgcgtcc     540
aagaccgaag ctgaactggc tgcatggaaa tttatggatg agaacaagcc acacttcact     600
ctgaacgctg tactgccaaa ctacactatt ggcactattt tcgatccgga aactcagtcc     660
ggttccacct ccggttggat gatgtccctg tttaacggcg aggtttcccc ggctctggct     720
ctgatgccac cgcagtacta cgtttccgct gttgatattg gcctgctgca cctgggttgc     780
ctggttctgc cacaaatcga acgtcgtcgt gtttacggta cggctggtac tttcgattgg     840
aacaccgttc tggctacctt ccgtaaactg tacccgtcca aaaccttccc ggctgacttc     900
ccagatcaag gtcaggacct gtctaaattc gacaccgctc cgtccctgga aattctgaaa     960
tctctgggtc gcccaggttg gcgttccatc gaagaatcca tcaaagacct ggttggttcc    1020
gaaaccgct                                                            1029
```

<210> SEQ ID NO 170
<211> LENGTH: 343
<212> TYPE: PRT
<213> ORGANISM: Artificial Sequence
<220> FEATURE:
<223> OTHER INFORMATION: KRED-101 variant

<400> SEQUENCE: 170

```
Met Ala Lys Ile Asp Asn Ala Val Leu Pro Glu Gly Ser Leu Val Leu
1               5                   10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Thr Ser
                85                  90                  95

Phe Ser Asn Lys Tyr Asp Glu Val Val Thr Pro Ala Ile Gly Gly Thr
            100                 105                 110

Leu Val Ala Leu Arg Ala Ala Ala Thr Pro Ser Val Lys Arg Phe
        115                 120                 125

Val Leu Thr Ser Ser Thr Phe Ser Ala Leu Val Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255
```

His Leu Gly Cys Leu Val Leu Pro Gln Ile Glu Arg Arg Val Tyr
             260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Ser Ile Lys Asp
                325                 330                 335

Leu Val Gly Ser Glu Thr Ala
            340

<210> SEQ ID NO 171
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 171
atgctgccga aactcgttat aactcaccga gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggctgcg cgctcaaggg cttcgacaat     240
ttcgatgtgg acgcctgtac tgcccgcggg gtctggctga ccttcgtgcc tgatctgttg     300
acggtcccga ctgccgagct ggcgatcgga ctggcggtgg ggctggggcg catctgcgg     360 gcagcagatg cgttcgtccg ctctggcaag ttccggggct ggcaaccacg gttctacggc     420
acggggctgg ataacgctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctcggta      720 gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcacatag ggtcggcagt gcgcgcggtg     900
cgcctggaga ttgaacgttg tgcagcgcag aacatcctcc aggcattggc aggtgagcgc     960
ccaatcaacg ctgtgaaccg tctgcccaag gccgagcctg ccgcatgttg a            1011

<210> SEQ ID NO 172
<211> LENGTH: 336
<212> TYPE: PRT
<213> ORGANISM: Artificial Sequence
<220> FEATURE:
<223> OTHER INFORMATION: PDH-101 variant

<400> SEQUENCE: 172

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

```
Thr Leu Thr Arg Glu Glu Ile Leu Arg Arg Cys Arg Asp Ala Gln Ala
             35                  40                  45

Met Met Ala Phe Met Pro Asp Arg Val Asp Ala Asp Phe Leu Gln Ala
 50                  55                  60

Cys Pro Glu Leu Arg Val Ile Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
            115                 120                 125

Gly Lys Phe Arg Gly Trp Gln Pro Arg Phe Tyr Gly Thr Gly Leu Asp
        130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335

<210> SEQ ID NO 173
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 173
atgctgccga aactcgttat aactcacaaa gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggcgctg cgctcaaggg ctttgacaat     240
ttcgatgtgg acgcctgtac tgcccgcggg gtctggctga ccttcgtgcc tgatctgttg     300
acggtcccga ctgccgagct ggcgatcgga ctggcggtgg gctgggggcg gcatctgcgg     360
```

-continued

```
gcagcagatg cgttcgtccg ctctggcaag ttccggggct ggcaaccaca gttctacggc    420
acggggctgg ataacgctac ggtcggcttc cttggcatgg cgccatcgg actggccatg    480
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtta cccctgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag ggtcggcagt gcgcgcggtg    900
cgcctggaaa ttgaacgttg cgcagcgcag aacatcctcc aggcattggc aggtgagcgc    960
ccaatcaacg ctgtgaaccg tctgcccaag gccgagcctg ccgcatgttg a           1011
```

<210> SEQ ID NO 174
<211> LENGTH: 336
<212> TYPE: PRT
<213> ORGANISM: Artificial Sequence
<220> FEATURE:
<223> OTHER INFORMATION: PDH-101 variant

<400> SEQUENCE: 174

```
Met Leu Pro Lys Leu Val Ile Thr His Lys Val His Glu Glu Ile Leu
1               5                   10                  15
Gln Leu Leu Ala Pro His Cys Glu Leu Ile Thr Asn Gln Thr Asp Ser
            20                  25                  30
Thr Leu Thr Arg Glu Glu Ile Leu Arg Arg Cys Arg Asp Ala Gln Ala
        35                  40                  45
Met Met Ala Phe Met Pro Asp Arg Val Asp Ala Asp Phe Leu Gln Ala
    50                  55                  60
Cys Pro Glu Leu Arg Val Ile Gly Ala Ala Leu Lys Gly Phe Asp Asn
65                  70                  75                  80
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
            100                 105                 110
Val Gly Leu Gly Arg His Leu Arg Ala Ala Asp Ala Phe Val Arg Ser
        115                 120                 125
Gly Lys Phe Arg Gly Trp Gln Pro Gln Phe Tyr Gly Thr Gly Leu Asp
    130                 135                 140
Asn Ala Thr Val Gly Phe Leu Gly Met Gly Ala Ile Gly Leu Ala Met
145                 150                 155                 160
Ala Asp Arg Leu Gln Gly Trp Gly Ala Thr Leu Gln Tyr His Ala Arg
                165                 170                 175
Lys Ala Leu Asp Thr Gln Thr Glu Gln Arg Leu Gly Leu Arg Gln Val
            180                 185                 190
Ala Cys Ser Glu Leu Phe Ala Ser Ser Asp Phe Ile Leu Leu Ala Leu
        195                 200                 205
Pro Leu Asn Ala Asp Thr Leu His Leu Val Asn Ala Glu Leu Leu Ala
    210                 215                 220
Leu Val Arg Pro Gly Ala Leu Leu Val Asn Pro Cys Arg Gly Ser Val
225                 230                 235                 240
Val Asp Glu Ala Ala Val Leu Ala Ala Leu Glu Arg Gly Gln Leu Gly
                245                 250                 255
```

Gly Tyr Ala Ala Asp Val Phe Glu Met Glu Asp Trp Ala Arg Ala Asp
                260                 265                 270

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Glu Ile
        290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335

<210> SEQ ID NO 175
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 175
atgctgccga aactcgttat aactcacaaa gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggcgctg cgctcaaggg ctatgacaat     240
ttcgatgtgg acgcctgtac tgcccgcggg gtctggctga ccttcgtgcc tgatctgttg     300
acggtcccga ctgccgagct ggccatcgga ctggcggtgg ggctggggcg catctgcgg     360
gcagcagatg cgttcgtccg ctctggcaag ttcggggct ggcaaccacg gttctacggc     420
acggggctgg ataacgctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttatta cccctgtcg tggctcggta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcacatag gtcggcagt gcgcgcggtg     900
cgcctggaga ttgaacgttg cgcagcgcag aacatcctcc aggcattggc aggtgagcgc     960
ccaatcgacg ctgtgaaccg tctgcccaag gccgagcctg ccgcatgttg a            1011

<210> SEQ ID NO 176
<211> LENGTH: 336
<212> TYPE: PRT
<213> ORGANISM: Artificial Sequence
<220> FEATURE:
<223> OTHER INFORMATION: PDH-101 variant

<400> SEQUENCE: 176

Met Leu Pro Lys Leu Val Ile Thr His Lys Val His Glu Glu Ile Leu
1               5                   10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Arg Asp Ala Gln Ala
        35                  40                  45

```
Met Met Ala Phe Met Pro Asp Arg Val Asp Ala Asp Phe Leu Gln Ala
    50                  55                  60
Cys Pro Glu Leu Arg Val Ile Gly Ala Ala Leu Lys Gly Tyr Asp Asn
65                  70                  75                  80
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
                100                 105                 110
Val Gly Leu Gly Arg His Leu Arg Ala Ala Asp Ala Phe Val Arg Ser
            115                 120                 125
Gly Lys Phe Arg Gly Trp Gln Pro Arg Phe Tyr Gly Thr Gly Leu Asp
    130                 135                 140
Asn Ala Thr Val Gly Phe Leu Gly Met Gly Ala Ile Gly Leu Ala Met
145                 150                 155                 160
Ala Asp Arg Leu Gln Gly Trp Gly Ala Thr Leu Gln Tyr His Ala Arg
                165                 170                 175
Lys Ala Leu Asp Thr Gln Thr Glu Gln Arg Leu Gly Leu Arg Gln Val
                180                 185                 190
Ala Cys Ser Glu Leu Phe Ala Ser Ser Asp Phe Ile Leu Leu Ala Leu
            195                 200                 205
Pro Leu Asn Ala Asp Thr Leu His Leu Val Asn Ala Glu Leu Leu Ala
    210                 215                 220
Leu Val Arg Pro Gly Ala Leu Leu Ile Asn Pro Cys Arg Gly Ser Val
225                 230                 235                 240
Val Asp Glu Ala Ala Val Leu Ala Ala Leu Glu Arg Gly Gln Leu Gly
                245                 250                 255
Gly Tyr Ala Ala Asp Val Phe Glu Met Glu Asp Trp Ala Arg Ala Asp
                260                 265                 270
Arg Pro Gln Gln Ile Asp Pro Ala Leu Leu Ala His Pro Asn Thr Leu
            275                 280                 285
Phe Thr Pro His Ile Gly Ser Ala Val Arg Ala Val Arg Leu Glu Ile
    290                 295                 300
Glu Arg Cys Ala Ala Gln Asn Ile Leu Gln Ala Leu Ala Gly Glu Arg
305                 310                 315                 320
Pro Ile Asp Ala Val Asn Arg Leu Pro Lys Ala Glu Pro Ala Ala Cys
                325                 330                 335

<210> SEQ ID NO 177
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 177
atgctgccga aactcgttat aactcacaga gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggctgtg cgctcaaggg ctttgacaat     240
ttcgatgtgg acgcctgtac tgcccgcggg gtctggctga ccttcgtgcc tgatctgttg     300
acggtcccga ctgccgagct ggccatcgga ctggcggtgg gctggggcg gcatctgcgg     360 gcagcagatg cgttcgtccg ctctggcaag ttcgggggct ggcaaccaca gttctacggc     420
acggggctgg ataacgctac ggtcggcttc cttggcatgg gcgccatcgg actggccatg     480
```

```
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttatta ccccctgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag ggtcggcagt gcgcgcggtg    900
cgcctggcaa ttgaacgttg cgcagcgcag aacatcctcc aggcattggc aggtgagcgc    960
ccaatcgacg ctgtgaaccg tctgcccaag gccgagcctg ccgcatgttg a            1011
```

<210> SEQ ID NO 178
<211> LENGTH: 336
<212> TYPE: PRT
<213> ORGANISM: Artificial Sequence
<220> FEATURE:
<223> OTHER INFORMATION: PDH-101 variant

<400> SEQUENCE: 178

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Arg Gly Trp Gln Pro Gln Phe Tyr Gly Thr Gly Leu Asp
    130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Ile Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270
```

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Ala Ile
        290                 295                 300

Glu Arg Cys Ala Ala Gln Asn Ile Leu Gln Ala Leu Ala Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 179
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 179
atgctgccga aactcgttat aactcacaaa gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggcgctg cgctcaaggg ctatgacaat     240
ttcgatgtgg acgcctgtac tgcccgcggg gtctggctga ccttcgtgcc tgatctgttg     300
acggtcccga ctgccgagct ggcgatcgga ctggcggtgg gctggggcg catctgcgg      360 gcagcagatg cgttcgtccg ctctggcaag ttccggggct ggcaaccaca gttctacggc     420
acggggctgg ataacgctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctcggta     720 gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcacatag gtcggcagt gcgcgcggtg      900 cgcctggaga ttgaacgttg tgcagcgcag aacatcctcc aggcattggc aggtgagcgc     960
ccaatcgacg ctgcgaaccg tctgcccaag gccgagcctg ccgcatgttg a             1011

<210> SEQ ID NO 180
<211> LENGTH: 336
<212> TYPE: PRT
<213> ORGANISM: Artificial Sequence
<220> FEATURE:
<223> OTHER INFORMATION: PDH-101 variant

<400> SEQUENCE: 180

Met Leu Pro Lys Leu Val Ile Thr His Lys Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

```
Cys Pro Glu Leu Arg Val Ile Gly Ala Ala Leu Lys Gly Tyr Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Arg Gly Trp Gln Pro Gln Phe Tyr Gly Thr Gly Leu Asp
    130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
    275                 280                 285

Phe Thr Pro His Ile Gly Ser Ala Val Arg Ala Val Arg Leu Glu Ile
290                 295                 300

Glu Arg Cys Ala Ala Gln Asn Ile Leu Gln Ala Leu Ala Gly Glu Arg
305                 310                 315                 320

Pro Ile Asp Ala Ala Asn Arg Leu Pro Lys Ala Glu Pro Ala Ala Cys
                325                 330                 335

<210> SEQ ID NO 181
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 181
atgctgccga aactcgttat aactcaccga gtacacgaag agatcctgca actgctggcg      60
ccacattgcg agctgataac caaccagacc gacagcacgc tgacgcgcga ggaaattctg    120
cggcgctgtg cagatgctca ggcgatgatg gcgttcatgc cgatcgggt cgatgcagac     180 tttcttcaag cctgccctga ctgcgtgta atcggctgcg cgctcaaggg cttcgacaat     240
ttcgatgtgg acgcctgtac tgcacgcggg gtctggctga ccttcgtgcc tgatctgttg    300
acggtcccga ctgccgagct ggcgatcgga ctggcggtgg ggctggggcg catctgcgcg   360
gcagcagatg cgttcgtccg ctctggcaag ttccagggct ggcaaccacg gttctacggc    420
acggggctgg atgagctac ggtcggcttc cttggcatgg gcgccatcgg actggccatg      480
gctgatcgct tgcagggatg gggcgcgacc ctgcagtacc acgcgcggaa ggctctggat    540
```

```
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtaa acccctgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag ggtcggcagt gcgcgcggtg    900
cgcctggaga ttgaacgttg tgcagcgcag aacatcctcc aggcattggc aggtgagcgc    960
ccaattaacg ctgtgaaccg tctgcccaag gccgagcctg ccgcatgttg a            1011
```

<210> SEQ ID NO 182
<211> LENGTH: 336
<212> TYPE: PRT
<213> ORGANISM: Artificial Sequence
<220> FEATURE:
<223> OTHER INFORMATION: PDH-101 variant

<400> SEQUENCE: 182

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Gln Gly Trp Gln Pro Arg Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
    275                 280                 285
```

```
Phe Thr Pro His Ile Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335
```

<210> SEQ ID NO 183
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 183

```
atgctgccga aactcgttat aactcaccga gtacacgatg agatcctgca actgctggcg      60
ccacattgcg agctgataac caaccagacc gacagcacgc tgacgcgcga ggaaattctg     120
gcacgctgtc gggatgctca ggcgatgatg gcgttcatgc cgatcgggt cgatgcagat      180
tttcttgctg cctgccctga gctgcgtgta atcggctgcg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatctgcgg     360
gcagcagatg cgttcgtccg ctctggcaag ttccagggct ggcaaccacg gttctacggc     420
acggggctgg ataacgctac ggtcggcttc cttggcatgg cgccatcgg actggccatg     480
gctgatcgct tgcagggatg gggcgcgacc ctgcagtacc acgcgcggaa ggctctggat     540
acacaaaccg agcaacggct cggcctgcgc caggtgtcgt gcgaagaact cttcgccagc     600
tcggacttca tcctgctggc gcttcccttg aatgccgata ccctgcatct ggtcaacgcc     660
gagctgcttg ccctcgtacg gccgggcgct ctgcttgtaa acccctgtcg tggctcggta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcacatag gtcggcagt gcgcgcggtg     900
cgcctggaga ttgaacgttg tgcagcgcag aacatcctcc aggcattggc aggtgagcgc     960
ccaatcaacg ctgtgaaccg tctgcccaag gccgagcctg ccgcatgttg a             1011
```

<210> SEQ ID NO 184
<211> LENGTH: 336
<212> TYPE: PRT
<213> ORGANISM: Artificial Sequence
<220> FEATURE:
<223> OTHER INFORMATION: PDH-101 variant

<400> SEQUENCE: 184

```
Met Leu Pro Lys Leu Val Ile Thr His Arg Val His Asp Glu Ile Leu
1               5                   10                  15

Gln Leu Leu Ala Pro His Cys Glu Leu Ile Thr Asn Gln Thr Asp Ser
                20                  25                  30

Thr Leu Thr Arg Glu Glu Ile Leu Ala Arg Cys Arg Asp Ala Gln Ala
            35                  40                  45

Met Met Ala Phe Met Pro Asp Arg Val Asp Ala Asp Phe Leu Ala Ala
        50                  55                  60

Cys Pro Glu Leu Arg Val Ile Gly Cys Ala Leu Lys Gly Phe Asp Asn
65                  70                  75                  80
```

```
Phe Asp Val Asp Ala Cys Thr Ala Arg Gly Val Trp Leu Thr Phe Val
             85                  90                  95
Pro Asp Leu Leu Thr Val Pro Thr Ala Glu Leu Ala Ile Gly Leu Ala
        100                 105                 110
Val Gly Leu Gly Arg His Leu Arg Ala Ala Asp Ala Phe Val Arg Ser
        115                 120                 125
Gly Lys Phe Gln Gly Trp Gln Pro Arg Phe Tyr Gly Thr Gly Leu Asp
    130                 135                 140
Asn Ala Thr Val Gly Phe Leu Gly Met Gly Ala Ile Gly Leu Ala Met
145                 150                 155                 160
Ala Asp Arg Leu Gln Gly Trp Gly Ala Thr Leu Gln Tyr His Ala Arg
                165                 170                 175
Lys Ala Leu Asp Thr Gln Thr Glu Gln Arg Leu Gly Leu Arg Gln Val
            180                 185                 190
Ser Cys Glu Glu Leu Phe Ala Ser Ser Asp Phe Ile Leu Leu Ala Leu
        195                 200                 205
Pro Leu Asn Ala Asp Thr Leu His Leu Val Asn Ala Glu Leu Leu Ala
    210                 215                 220
Leu Val Arg Pro Gly Ala Leu Leu Val Asn Pro Cys Arg Gly Ser Val
225                 230                 235                 240
Val Asp Glu Ala Ala Val Leu Ala Ala Leu Glu Arg Gly Gln Leu Gly
                245                 250                 255
Gly Tyr Ala Ala Asp Val Phe Glu Met Glu Asp Trp Ala Arg Ala Asp
            260                 265                 270
Arg Pro Gln Gln Ile Asp Pro Ala Leu Leu Ala His Pro Asn Thr Leu
        275                 280                 285
Phe Thr Pro His Ile Gly Ser Ala Val Arg Ala Val Arg Leu Glu Ile
    290                 295                 300
Glu Arg Cys Ala Ala Gln Asn Ile Leu Gln Ala Leu Ala Gly Glu Arg
305                 310                 315                 320
Pro Ile Asn Ala Val Asn Arg Leu Pro Lys Ala Glu Pro Ala Ala Cys
                325                 330                 335
```

<210> SEQ ID NO 185
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 185

```
atgctgccga aactcgttat aactcaccga gtacacgaag agatcctgca actgctggcg    60
ccacattgcg agctgataac caaccagacc gacagcacgc tgacgcgcga ggaaattctg   120
gcacgctgtg cagatgctca ggcgatgatg gcgttcatgc ccgatcgggt cgatgcagat   180
tttcttcagg cctgccctga gctgcgtgta atcggctgcg cgctcaaggg cttcgacaat   240
ttcgatgtgg acgcctgtac tcggcgcggg gtctggctga ccttcgtgcc tgatctgttg   300
acggtcccga ctgccgagct ggcgatcgga ctggcggtgg ggctggggcg catctgcgg   360 gcagcagatg cgttcgtccg ctctggcaag ttccggggct ggcaaccacg gttctacggc   420
acggggctgg ataacgctac ggtcggcttc cttggcatgg gcgccatcgg actggccatg   480
gctgatcgct tgcagggatg gggcgcgacc ctgcagtacc acgcgcggaa ggctctggat   540
acacaaaccg agcaacggct cggcctgcgc caggtgtcgt gcgaagaact cttcgccagc   600
tcggacttca tcctgctggc gcttcccttg aatgccgata ccctgcatct ggtcaacgcc   660
```

```
gagctgcttg ccctcgtacg gccgggcgct ctgcttgtaa acccctgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag ggtcggcagt gcgcgcggtg    900
cgcctggaga ttgaacgttg tgcagcgcag aacatcctcc aggcattggc aggtgagcgc    960
ccaatcaacg ctgtgaaccg tctgcccaag gccgagcctg ccgcatgttg a            1011
```

<210> SEQ ID NO 186
<211> LENGTH: 336
<212> TYPE: PRT
<213> ORGANISM: Artificial Sequence
<220> FEATURE:
<223> OTHER INFORMATION: PDH-101 variant

<400> SEQUENCE: 186

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Ala Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Arg Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Arg Gly Trp Gln Pro Arg Phe Tyr Gly Thr Gly Leu Asp
    130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ser Cys Glu Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300
```

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335

<210> SEQ ID NO 187
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 187

```
atgctgccga aactcgttat aactcaccga gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggctgcg cgctcaaggg cttcgacaat     240
ttcgatgtgg acgcctgtac tgcccgcggg gtctggctga ccttcgtgcc tgatctgttg     300
acggtcccga ctgccgagct ggcgatcgga ctggcggtgg ggctggggcg catctgcgg     360
gcagcagatg cgttcgtccg ctctggcaag ttccggggct ggcaaccacg gttctacggc     420
acggggctgg ataacgctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accccgtcg tggctcggta     720
gtggatgaag ccgccgtgct cgcggcgctt gagcgaggcc agctcggcgg gtatgcggcg     780
gatgtattcg aaatggttga ctgggctcgc gcggaccggc cgcagcagat cgatcctgcg     840
ctgctcgcgc atccgaatac gctgttcact ccgcacatag ggtcggcagt gcgcgcggtg     900
cgcctggaga ttgaacgttg tgcagcgcag aacatcctcc aggcattggc aggtgagcgc     960
ccaatcaacg ctgtgaaccg tctgcccaag gccgagcctg ccgcatgttg a             1011
```

<210> SEQ ID NO 188
<211> LENGTH: 336
<212> TYPE: PRT
<213> ORGANISM: Artificial Sequence
<220> FEATURE:
<223> OTHER INFORMATION: PDH-101 variant

<400> SEQUENCE: 188

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Asp Ala Phe Val Arg Ser
        115                 120                 125

Gly Lys Phe Arg Gly Trp Gln Pro Arg Phe Tyr Gly Thr Gly Leu Asp
    130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
        180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Val Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Glu Ile
        290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335

<210> SEQ ID NO 189
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 189
atgctgccga aactcgttat aactcaccga gtacacgaag agatcctgca actgctggcg      60
ccacattgcg agctgataac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta atcggctgcg cgctcaaggg cttcgacaat     240
ttcgatgtgg acgcctgtac tgcccgcggg gtctggctga ccttcgtgcc tgatctgttg     300
acggtcccga ctgccgagct ggcgatcgga ctggcggtgg gctgggggcg catctgcgg      360 gcagcagatg cgttcgtccg ctctggcaag ttccggggct ggcaaccacg gttctacggc     420
acggggctgg ataacgctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accccgtgcg tggctcggta     720

```
gtggatgaag ccgccgtgct cgcggcgctt gagcgaggcc agctcggcgg gtatgcggcg    780
gatgtattcg aaatgtggga ctgggctcgc gcggaccggc cgcagcagat cgatcctgcg    840
ctgctcgcgc atccgaatac gctgttcact ccgcacatag ggtcggcagt gcgcgcggtg    900
cgcctggaga ttgaacgttg tgcagcgcag aacatcctcc aggcattggc aggtgagcgc    960
ccaatcaacg ctgtgaaccg tctgcccaag gccgagcctg ccgcatgttg a            1011
```

<210> SEQ ID NO 190
<211> LENGTH: 336
<212> TYPE: PRT
<213> ORGANISM: Artificial Sequence
<220> FEATURE:
<223> OTHER INFORMATION: PDH-101 variant

<400> SEQUENCE: 190

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Arg Gly Trp Gln Pro Arg Phe Tyr Gly Thr Gly Leu Asp
    130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Trp Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320
```

Pro Ile Asn Ala Val Asn Arg Leu Pro Lys Ala Glu Pro Ala Ala Cys
            325                 330                 335

<210> SEQ ID NO 191
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 191

| | | | | | |
|---|---|---|---|---|---|
| atgctgccga | aactcgttat | aactcaccga | gtacacgaag | agatcctgca | actgctggcg | 60 |
| ccacattgcg | agctgataac | caaccagacc | gacagcacgc | tgacgcgcga | ggaaattctg | 120 |
| cgccgctgtc | gcgatgctca | ggcgatgatg | gcgttcatgc | cgatcgggt | cgatgcagac | 180 |
| tttcttcaag | cctgccctga | gctgcgtgta | atcggctgcg | cgctcaaggg | cttcgacaat | 240 |
| ttcgatgtgg | acgcctgtac | tgcccgcggg | gtctggctga | ccttcgtgcc | tgatctgttg | 300 |
| acggtcccga | ctgccgagct | ggcgatcgga | ctggcggtgg | ggctggggcg | catctgcgg | 360 |
| gcagcagatg | cgttcgtccg | ctctggcaag | ttccggggct | ggcaaccacg | gttctacggc | 420 |
| acggggctgg | ataacgctac | ggtcggcttc | cttggcatgg | gcgccatcgg | actggccatg | 480 |
| gctgatcgct | gcagggatg | gggcgcgacc | ctgcagtacc | acgcgcggaa | ggctctggat | 540 |
| acacaaaccg | agcaacggct | cggcctgcgc | aggtggcgt | gcagcgaact | cttcgccagc | 600 |
| tcggacttca | tcctgctggc | gcttcccttg | aatgccgata | ccctgcatct | ggtcaacgcc | 660 |
| gagctgcttg | ccctcgtacg | gccgggcgct | ctgcttgtaa | accccgtcg | tggctcggta | 720 |
| gtggatgaag | ccgccgtgct | cgcggcgctt | gagcgaggcc | agctcggcgg | gtatgcggcg | 780 |
| gatgtattcg | aaatgtctga | ctgggctcgc | gcggaccggc | cgcagcagat | cgatcctgcg | 840 |
| ctgctcgcgc | atccgaatac | gctgttcact | ccgcacatag | ggtcggcagt | gcgcgcggtg | 900 |
| cgcctggaga | ttgaacgttg | tgcagcgcag | aacatcctcc | aggcattggc | aggtgagcgc | 960 |
| ccaatcaacg | ctgtgaaccg | tctgcccaag | gccgagcctg | ccgcatgttg | a | 1011 |

<210> SEQ ID NO 192
<211> LENGTH: 336
<212> TYPE: PRT
<213> ORGANISM: Artificial Sequence
<220> FEATURE:
<223> OTHER INFORMATION: PDH-101 variant

<400> SEQUENCE: 192

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
            115                 120                 125

Gly Lys Phe Arg Gly Trp Gln Pro Arg Phe Tyr Gly Thr Gly Leu Asp
        130                 135                 140

Asn Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Ser Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335

<210> SEQ ID NO 193
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 193
atgctgccga aactcgttat aactcaccga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgcg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg gctggggcg gcatctgcgg      360 gcagcagatg cgttcgtccg ctctggcaag ttccagggct ggcaggacca gttctacggc     420
acggggctgg atggagctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtta accccgtgcg tggctcggta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840

```
ctgctcgcgc atccgaatac gctgttcact ccgcaccttg ggtcggcagt gcgcgcggtg      900
cgcctggaga ttgaacgttg tgcggcgcag aacatcctcc aggcattggc aggtgagcgc      960
ccaattaacg ctgtgaaccg tctgcccaag gccgagcctg ccgcatgttg a              1011
```

<210> SEQ ID NO 194
<211> LENGTH: 336
<212> TYPE: PRT
<213> ORGANISM: Artificial Sequence
<220> FEATURE:
<223> OTHER INFORMATION: PDH-101 variant

<400> SEQUENCE: 194

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Gln Gly Trp Gln Asp Gln Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335
```

<210> SEQ ID NO 195
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 195

```
atgctgccga aactcgttat aactcaccga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgcg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg catctgcgg      360
gcagcagatg cgttcgtccg ctctggcaag ttccagggct ggcagccaat tttctacggc     420
acggggctgg atggagctac ggtcggcttc cttggcatgg cgccatcgg  actggccatg     480
gctgatcgct gcagggatg gggcgcgacc ctgcagtacc acgcgcggaa ggctctggat     540
acacaaaccg agcaacggct cggcctgcgc aggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttatta ccccctgtcg tggctcggta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcacatag ggtcggcagt gcgcgcggtg     900
cgcctggaga ttgaacgttg tgtggcgcag aacatcctcc aggcattggc aggtgagcgc     960
ccaattgacg ctgtgaaccg tctgcccaag gccgagcctg ccgcatgttg a             1011
```

<210> SEQ ID NO 196
<211> LENGTH: 336
<212> TYPE: PRT
<213> ORGANISM: Artificial Sequence
<220> FEATURE:
<223> OTHER INFORMATION: PDH-101 variant

<400> SEQUENCE: 196

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125
```

| | | | | | | | | | | | |
|---|---|---|---|---|---|---|---|---|---|---|---|
|Gly|Lys|Phe|Gln|Gly|Trp|Gln|Pro|Ile|Phe|Tyr|Gly Thr Gly Leu Asp|
| |130| | | |135| | | |140| | |

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
            165                 170                 175

Lys Ala Leu Asp Thr Gln Thr Glu Gln Arg Leu Gly Leu Arg Gln Val
               180                 185                 190

Ala Cys Ser Glu Leu Phe Ala Ser Ser Asp Phe Ile Leu Leu Ala Leu
            195                 200                 205

Pro Leu Asn Ala Asp Thr Leu His Leu Val Asn Ala Glu Leu Leu Ala
210                 215                 220

Leu Val Arg Pro Gly Ala Leu Leu Ile Asn Pro Cys Arg Gly Ser Val
225                 230                 235                 240

Val Asp Glu Ala Ala Val Leu Ala Ala Leu Glu Arg Gly Gln Leu Gly
               245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
         275                 280                 285

Phe Thr Pro His Ile Gly Ser Ala Val Arg Ala Val Arg Leu Glu Ile
290                 295                 300

Glu Arg Cys Val Ala Gln Asn Ile Leu Gln Ala Leu Ala Gly Glu Arg
305                 310                 315                 320

Pro Ile Asp Ala Val Asn Arg Leu Pro Lys Ala Glu Pro Ala Ala Cys
               325                 330                 335

<210> SEQ ID NO 197
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 197

```
atgctgccga aactcgttat aactcaccga gtacacgaag agatcctgca actgctggcg    60
ccacattgcg agctgataac caaccagacc gacagcacgc tgacgcgcga ggaaattctg   120
cggcgctgtg cagatgctca ggcgatgatg cgttcatgc cgatcgggt cgatgcagac    180
tttcttcaag cctgccctga gctgcgtgta atcggctgcg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gctggggcg catctgcgg    360
gcagcagatg cgttcgtccg ctctggcaag ttccagggct gggctgacat tttctacggc   420
acggggctgg atggagctac ggtcggcttc cttggcatgg gcgccatcgg actggccatg   480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtta cccctgtcg tggctcggta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg   900
```

```
cgcctggaga ttgaacgttg tgcagcgcag aacatcctcc aggcattggc aggtgagcgc      960
ccaattaacg ctgtgaaccg tctgcccaag gccgagcctg ccgcatgttg a              1011
```

<210> SEQ ID NO 198
<211> LENGTH: 336
<212> TYPE: PRT
<213> ORGANISM: Artificial Sequence
<220> FEATURE:
<223> OTHER INFORMATION: PDH-101 variant

<400> SEQUENCE: 198

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Gln Gly Trp Ala Asp Ile Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
                325                 330                 335
```

<210> SEQ ID NO 199

-continued

<211> LENGTH: 1011
<212> TYPE: DNA
<213> ORGANISM: Artificial Sequence
<220> FEATURE:
<223> OTHER INFORMATION: PDH-101 variant

<400> SEQUENCE: 199

```
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg gcatctgcgg    360
gcagcagatg cgttcgtccg ctctggcaag ttccagggct ggcagccaat tttctacggc    420
acggggctgg atggagctac ggtcggcttc cttggcatgg gcgccatcgg actggccatg    480
gctgatcgct gcagggatgg ggcgcgacc  ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtaa accctgtcg  tggctctgta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg gtcggcagt  gcgcgcggtg    900
cgcctggaga ttgaacgttg tgcagcgcag aacatcctcc aggcattggc aggtgagcgc    960
ccaattgacg ctgtgaaccg tctgcccaag gccgagcctg ccgcatgttg a            1011
```

<210> SEQ ID NO 200
<211> LENGTH: 336
<212> TYPE: PRT
<213> ORGANISM: Artificial Sequence
<220> FEATURE:
<223> OTHER INFORMATION: PDH-101 variant

<400> SEQUENCE: 200

```
Met Leu Pro Lys Leu Val Ile Thr His Arg Val His Glu Glu Ile Leu
1               5                   10                  15
Gln Leu Leu Ala Pro His Cys Glu Leu Ile Thr Asn Gln Thr Asp Ser
            20                  25                  30
Thr Leu Thr Arg Glu Glu Ile Leu Arg Arg Cys Ala Asp Ala Gln Ala
        35                  40                  45
Met Met Ala Phe Met Pro Asp Arg Val Asp Ala Asp Phe Leu Gln Ala
    50                  55                  60
Cys Pro Glu Leu Arg Val Ile Gly Cys Ala Leu Lys Gly Phe Asp Asn
65                  70                  75                  80
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
            100                 105                 110
Val Gly Leu Gly Arg His Leu Arg Ala Ala Asp Ala Phe Val Arg Ser
        115                 120                 125
Gly Lys Phe Gln Gly Trp Gln Pro Ile Phe Tyr Gly Thr Gly Leu Asp
    130                 135                 140
```

```
Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
            165                 170                 175

Lys Ala Leu Asp Thr Gln Thr Glu Gln Arg Leu Gly Leu Arg Gln Val
        180                 185                 190

Ala Cys Ser Glu Leu Phe Ala Ser Ser Asp Phe Ile Leu Leu Ala Leu
    195                 200                 205

Pro Leu Asn Ala Asp Thr Leu His Leu Val Asn Ala Glu Leu Leu Ala
210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
            245                 250                 255

Gly Tyr Ala Ala Asp Val Phe Glu Met Glu Asp Trp Ala Arg Ala Asp
        260                 265                 270

Arg Pro Gln Gln Ile Asp Pro Ala Leu Leu Ala His Pro Asn Thr Leu
    275                 280                 285

Phe Thr Pro His Leu Gly Ser Ala Val Arg Ala Val Arg Leu Glu Ile
290                 295                 300

Glu Arg Cys Ala Ala Gln Asn Ile Leu Gln Ala Leu Ala Gly Glu Arg
305                 310                 315                 320

Pro Ile Asp Ala Val Asn Arg Leu Pro Lys Ala Glu Pro Ala Ala Cys
            325                 330                 335

<210> SEQ ID NO 201
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 201
atgctgccga aactcgttat aactcaccga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgcg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatctgcgg     360
gcagcagatg cgttcgtccg ctctggcaag ttccagggct ggcaaccacg gttctacggc     420
acggggctgg atggagctac ggtcggcttc cttggcatgg gcgccatcgg actggccatg     480
gctgatcgct tgcagggatg gggcgcgacc ctgcagtacc acgcgcggaa ggctctggat     540
acacaaaccg agcaacggct cggcctgcgc caggtggcgt gcgaggaact cttcgccagc     600
tcggacttca tcctgctggc gcttcccttg aatgccgata ccctgcatct ggtcaacgcc     660
gagctgcttg ccctcgtacg gccgggcgct ctgcttgtta accctgtcg tggctcggta     720 gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg     900 cgcctggaga ttgaacgttg tgcagcgcag aacatcctcc aggcattggc aggtgagcgc     960
ccaattgacg ctgtgaaccg tctgcccaag gccgagcctg ccgcatgtta a            1011
```

<210> SEQ ID NO 202
<211> LENGTH: 336
<212> TYPE: PRT
<213> ORGANISM: Artificial Sequence
<220> FEATURE:
<223> OTHER INFORMATION: PDH-101 variant

<400> SEQUENCE: 202

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Gln Gly Trp Gln Pro Arg Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Glu Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 203
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 203

```
atgctgccga aactcgttat aactcaccga gtacacgaag agatcctgca actgctggcg        60
ccacattgcg agctgataac caaccagacc gacagcacgc tgacgcgcga ggaaattctg       120
cggcgctgtg cagatgctca ggcgatgatg gcgttcatgc ccgatcgggt cgatgcagac       180
tttcttcaag cctgccctga gctgcgtgta atcggctgcg cgctcaaggg cttcgacaat       240
ttcgatgtgg acgcctgtac tgcacgcggg gtctggctga ccttcgtgcc tgatctgttg       300
acggtcccga ctgccgagct ggcgatcgga ctggcgtcgg gctggggcg catctgcgg         360
gcagcagatg cgttcgtccg ctctggcaag ttccagggct ggcaaccacg gttctacggc       420
acggggctgg atgagctac ggtcggcttc cttggcatgg cgccatcgg actggccatg         480
gctgatcgct tgcagggatg gggcgcgacc ctgcagtacc acgcgcggaa ggctctggat       540
acacaaaccg agcaacggct cggcctgcgc caggtggcgt gcagcgaact cttcgccagc       600
tcggacttca tcctgctggc gcttcccttg aatgccgata ccctgcatct ggtcaacgcc       660
gagctgcttg ccctcgtacg gccgggcgct ctgcttgtaa accccgtcg tggctcggta        720
gtggatgaag ccgccgtgct cgcggcgctt gagcgaggcc agctcggcgg gtatgcggcg       780
gatgtattcg aaatggaaga ctgggctcgc gcggaccggc cgcagcagat cgatcctgcg       840
ctgctcgcgc atccgaatac gctgttcact ccgcacatag ggtcggcagt gcgcgcggtg       900
cgcctggaga ttgaacgttg tgcagcgcag aacatcctcc aggcattggc aggtgagcgc       960
ccaattaacg ctgtgaaccg tctgcccaag gccgagcctg ccgcatgttg a               1011
```

<210> SEQ ID NO 204
<211> LENGTH: 336
<212> TYPE: PRT
<213> ORGANISM: Artificial Sequence
<220> FEATURE:
<223> OTHER INFORMATION: PDH-101 variant

<400> SEQUENCE: 204

```
Met Leu Pro Lys Leu Val Ile Thr His Arg Val His Glu Glu Ile Leu
1               5                  10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Ser Gly Leu Gly Arg His Leu Arg Ala Ala Asp Ala Phe Val Arg Ser
        115                 120                 125

Gly Lys Phe Gln Gly Trp Gln Pro Arg Phe Tyr Gly Thr Gly Leu Asp
    130                 135                 140

Gly Ala Thr Val Gly Phe Leu Gly Met Gly Ala Ile Gly Leu Ala Met
145                 150                 155                 160
```

Ala Asp Arg Leu Gln Gly Trp Gly Ala Thr Leu Gln Tyr His Ala Arg
            165                 170                 175

Lys Ala Leu Asp Thr Gln Thr Glu Gln Arg Leu Gly Leu Arg Gln Val
        180                 185                 190

Ala Cys Ser Glu Leu Phe Ala Ser Ser Asp Phe Ile Leu Leu Ala Leu
    195                 200                 205

Pro Leu Asn Ala Asp Thr Leu His Leu Val Asn Ala Glu Leu Leu Ala
210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
            245                 250                 255

Gly Tyr Ala Ala Asp Val Phe Glu Met Glu Asp Trp Ala Arg Ala Asp
        260                 265                 270

Arg Pro Gln Gln Ile Asp Pro Ala Leu Leu Ala His Pro Asn Thr Leu
    275                 280                 285

Phe Thr Pro His Ile Gly Ser Ala Val Arg Ala Val Arg Leu Glu Ile
290                 295                 300

Glu Arg Cys Ala Ala Gln Asn Ile Leu Gln Ala Leu Ala Gly Glu Arg
305                 310                 315                 320

Pro Ile Asn Ala Val Asn Arg Leu Pro Lys Ala Glu Pro Ala Ala Cys
            325                 330                 335

<210> SEQ ID NO 205
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 205
atgctgccga aactcgttat aactcacaga gtacacgaag agatcctgca aatgctggcg       60
ccacattgcg agctgataac caaccagacc gacagcacgc tgacgcgcga ggaaattctg      120
cggcgctgtg cagatgctca ggcgatgatg gcgttcatgc cgatcgggt cgatgcagac       180 tttcttcaag cctgccctga gctgcgtgta atcggctgtg cgctcaaggg cttcgacaat      240
ttcgatgtgg acgcctgtac tgcacgcggg gtctggctga ccttcgtgcc tgatctgttg      300
acggtcccga ctgccgagct ggcgatcgga ctggcggtgg ggctggggcg gcatttccgg      360
gcagcagatg aattcgtccg ctctggcaag ttccagggct ggcagccaat tttctacggc      420
acggggctgg atggagcaac ggtcggcttc cttggcatgg gcgccatcgg actcgccatg      480
gctgatcgct tgcagggatg gggcgcgacc ctgcagtacc acgcgcggaa ggctctggat      540
acacaaaccg agcaacggct cggcctgcgc caggtggcgt gcagcgaact cttcgccagc      600
tcggacttca tcctgctggc gcttcccttg aatgccgata ccctgcatct ggtcaacgcc      660
gagctgcttg ccctcgtacg gccgggcgct ctgcttgtaa accccgtgcg tggctctgta      720
gtggatgaag ccgccgtgct cgcggcgctt gagcgaggcc agctcggcgg gtatgcggcg      780
gatgtattcg aaatggaaga ctgggctcgc gcggaccggc cgcagcagat cgatcctgcg      840
ctgctcgcgc atccgaatac gctgttcact ccgcaccttg gtcggcagt gcgcgcggtg      900 cgcctggaga ttgaacgttg tgcagcgcag aacatcctcc aggcattggc aggtgagcgc      960
ccaattgacg ctgtgaaccg tctgcccaag gccgagccca aggcccgctg a              1011

<210> SEQ ID NO 206

<211> LENGTH: 336
<212> TYPE: PRT
<213> ORGANISM: Artificial Sequence
<220> FEATURE:
<223> OTHER INFORMATION: PDH-101 variant

<400> SEQUENCE: 206

Met Leu Pro Lys Leu Val Ile Thr His Arg Val His Glu Glu Ile Leu
1               5                   10                  15

Gln Met Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Glu Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asp Ala Val Asn Arg Leu Pro Lys Ala Glu Pro Lys Ala Arg
                325                 330                 335

<210> SEQ ID NO 207
<211> LENGTH: 1011
<212> TYPE: DNA
<213> ORGANISM: Artificial Sequence
<220> FEATURE:
<223> OTHER INFORMATION: PDH-101 variant -continued

```
<400> SEQUENCE: 207
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc actcgcggac agctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accccgtcg tggctctgta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg ggtcggcagt gcgcgcggtg     900
cgcctggaga ttgaacgttg tgcagcgcag aacatcctcc aggcattgcg aggtgagcgc     960
ccaattgacg ctgtgaaccg tctgcccaag gccgagcctg ccgcatgttg a            1011
```

<210> SEQ ID NO 208
<211> LENGTH: 336
<212> TYPE: PRT
<213> ORGANISM: Artificial Sequence
<220> FEATURE:
<223> OTHER INFORMATION: PDH-101 variant

<400> SEQUENCE: 208

```
Met Leu Pro Lys Leu Val Ile Thr His Arg Val His Glu Glu Ile Leu
1               5                   10                  15
Gln Leu Leu Ala Pro His Cys Glu Leu Ile Thr Asn Gln Thr Asp Ser
            20                  25                  30
Thr Leu Thr Arg Glu Glu Ile Leu Arg Arg Cys Ala Asp Ala Gln Ala
        35                  40                  45
Met Met Ala Phe Met Pro Asp Arg Val Asp Ala Asp Phe Leu Gln Ala
    50                  55                  60
Cys Pro Glu Leu Arg Val Ile Gly Cys Ala Leu Lys Gly Phe Asp Asn
65                  70                  75                  80
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
            100                 105                 110
Val Gly Leu Gly Arg His Phe Arg Ala Ala Asp Ala Phe Val Arg Ser
        115                 120                 125
Gly Lys Phe Gln Gly Trp Gln Pro Ile Phe Tyr Gly Thr Gly Leu Asp
    130                 135                 140
Gly Ala Thr Val Gly Phe Leu Gly Met Gly Ala Ile Gly Lys Ala Met
145                 150                 155                 160
Ala Asp Arg Leu Gln Gly Trp Gly Ala Thr Leu Gln Tyr His Ser Arg
                165                 170                 175
```

```
Thr Ala Leu Asp Thr Gln Thr Glu Gln Arg Leu Gly Leu Arg Gln Val
                180                 185                 190
Ala Cys Ser Glu Leu Phe Ala Ser Ser Asp Phe Ile Leu Leu Ala Leu
            195                 200                 205
Pro Leu Asn Ala Asp Thr Leu His Leu Val Asn Ala Glu Leu Leu Ala
        210                 215                 220
Leu Val Arg Pro Gly Ala Leu Val Asn Pro Cys Arg Gly Ser Val
225                 230                 235                 240
Val Asp Glu Ala Ala Val Leu Ala Ala Leu Glu Arg Gly Gln Leu Gly
                245                 250                 255
Gly Tyr Ala Ala Asp Val Phe Glu Met Glu Asp Trp Ala Arg Ala Asp
            260                 265                 270
Arg Pro Gln Gln Ile Asp Pro Ala Leu Leu Ala His Pro Asn Thr Leu
        275                 280                 285
Phe Thr Pro His Leu Gly Ser Ala Val Arg Ala Val Arg Leu Glu Ile
    290                 295                 300
Glu Arg Cys Ala Ala Gln Asn Ile Leu Gln Ala Leu Arg Gly Glu Arg
305                 310                 315                 320
Pro Ile Asp Ala Val Asn Arg Leu Pro Lys Ala Glu Pro Ala Ala Cys
                325                 330                 335
```

<210> SEQ ID NO 209
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 209

```
atgctgccga aactcgttat aactcacaga gtacacgaag agatcctgca aatgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatttccgg     360
gcagcagatg aattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc acgcgcggac agctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctctgta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg     900
cgcctggaga ttgaacgttg tgcagcgcag aacatcctcc aggcattggc aggtgagcgc     960
ccaattgacg ctgtgaaccg tctgcccaag gccgagcctg ccgcatgttg a              1011
```

<210> SEQ ID NO 210
<211> LENGTH: 336
<212> TYPE: PRT
<213> ORGANISM: Artificial Sequence
<220> FEATURE:
<223> OTHER INFORMATION: PDH-101 variant

<400> SEQUENCE: 210

Met Leu Pro Lys Leu Val Ile Thr His Arg Val His Glu Glu Ile Leu
1               5                   10                  15

Gln Met Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Glu Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ala Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
    275                 280                 285

Phe Thr Pro His Leu Gly Ser Ala Val Arg Ala Val Arg Leu Glu Ile
290                 295                 300

Glu Arg Cys Ala Ala Gln Asn Ile Leu Gln Leu Ala Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 211
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 211
atgctgccga aactcgttat aactcacaga gtacacgaag agatcctgca aatgctggcg        60

```
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg cattccgg     360
gcagcagatg aattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagtgaact cttcgccagc    600
tcggacttca tcctgctggc gcttcccttg aatgccgata ccctgcatct ggtcaacgcc    660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgttg a            1011
```

<210> SEQ ID NO 212
<211> LENGTH: 336
<212> TYPE: PRT
<213> ORGANISM: Artificial Sequence
<220> FEATURE:
<223> OTHER INFORMATION: PDH-101 variant

<400> SEQUENCE: 212

```
Met Leu Pro Lys Leu Val Ile Thr His Arg Val His Glu Glu Ile Leu
1               5                   10                  15
Gln Met Leu Ala Pro His Cys Glu Leu Ile Thr Asn Gln Thr Asp Ser
            20                  25                  30
Thr Leu Thr Arg Glu Glu Ile Leu Arg Arg Cys Ala Asp Ala Gln Ala
        35                  40                  45
Met Met Ala Phe Met Pro Asp Arg Val Asp Ala Asp Phe Leu Gln Ala
    50                  55                  60
Cys Pro Glu Leu Arg Val Ile Gly Cys Ala Leu Lys Gly Phe Asp Asn
65                  70                  75                  80
Phe Asp Val Asp Ala Cys Thr Ala Arg Gly Val Trp Leu Thr Phe Val
                85                  90                  95
Pro Asp Leu Leu Thr Val Pro Thr Ala Glu Leu Ala Ile Gly Leu Ala
            100                 105                 110
Val Gly Leu Gly Arg His Phe Arg Ala Ala Asp Glu Phe Val Arg Ser
        115                 120                 125
Gly Lys Phe Gln Gly Trp Gln Pro Ile Phe Tyr Gly Thr Gly Leu Asp
    130                 135                 140
Gly Ala Thr Val Gly Phe Leu Gly Met Gly Ala Ile Gly Lys Ala Met
145                 150                 155                 160
Ala Asp Arg Leu Gln Gly Trp Gly Ala Thr Leu Gln Tyr His Ser Arg
                165                 170                 175
Thr Ala Leu Asp Thr Gln Thr Glu Gln Arg Leu Gly Leu Arg Gln Val
            180                 185                 190
```

```
Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
                260                 265                 270

Arg Pro Gln Gln Ile Asp Pro Ala Leu Leu Ala His Pro Asn Thr Leu
    275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335
```

<210> SEQ ID NO 213
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 213

```
atgctgccga aactcgttat aactcacaga gtacacgaag agatcctgca actgctggcg    60
ccacattgcg agctgataac caaccagacc gactcgacgc tgacgcgcga ggaaattctg   120
cggcgctgtg cagatgctca ggcgatgatg gcgttcatgc ccgatcgggt cgatgcagac   180
tttcttcaag cctgccctga gctgaaagta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gctgggggcg catctggtt   360
gcagcagatg cgttcgtccg ctctggcaag ttccagggct ggcagccaat tttctacggc   420
acggggctgg atggagctac ggtcggcttc cttggcatgg cgccatcgg actggccatg   480
gctgatcgct tgcagggatg gggcgcgacc ctgcagtacc acacccggaa ggctctggat   540
acacaaaccg agcaacggct cggcctgcgc caggtggcgt gcgaggaact cttcgccagc   600
tcggacttca tcctgctggc gcttcccttg aatgccgata ccctgcatct ggtcaacgcc   660
gagctgcttg ccctcgtacg gccgggcgct ctgcttgtta cccctgtcg tggctctgta   720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattggc aggtgagcgc   960
ccaattgacg ctgtgaaccg tctgcccaag gccgagcctg ccgcatgttg a          1011
```

<210> SEQ ID NO 214
<211> LENGTH: 336
<212> TYPE: PRT
<213> ORGANISM: Artificial Sequence
<220> FEATURE:
<223> OTHER INFORMATION: PDH-101 variant

<400> SEQUENCE: 214

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Lys Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Val Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Thr Arg
                165                 170                 175

Lys Ala Leu Asp Thr Gln Thr Glu Gln Arg Leu Gly Leu Arg Gln Val
            180                 185                 190

Ala Cys Glu Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asp Ala Val Asn Arg Leu Pro Lys Ala Glu Pro Ala Ala Cys
                325                 330                 335
```

<210> SEQ ID NO 215
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 215

```
atgctgccga aactcgttat aactcacaga gtacacgaag agatcctgca actgctggcg      60
ccacattgcg agctgataac caaccagacc gacgtcacgc tgacgcgcga ggaaattctg     120
```

```
cggcgctgtg cagatgctca ggcgatgatg gcgttcatgc ccgatcgggt cgatgcagac    180
tttcttcaag cctgccctga gctgagagta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg catctgcgc     360 gcagcagatg cgttcgtccg ctctggcaag ttccagggct ggcagccaat tttctacggc    420
acggggctgg atggagctac ggtcggcttc cttggcatgg gcgccatcgg actggccatg    480
gctgatcgct tgcagggatg gggcgcgacc ctgcagtacc acgcccggaa ggctctggat    540
acacaaactg agcaaaccct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg tccgggcgct ctgcttatta ccccctgtcg tggctctgta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg gtcggcagt  gcgcgcggtg    900 cgcctggaga ttgaacgttg tgcagcgcag aacatcctcc aggcattggc aggtgagcgc    960
ccaattgacg ctgtgaaccg tctgcccaag gccgagcctg ccgcaagctg a            1011
```

<210> SEQ ID NO 216
<211> LENGTH: 336
<212> TYPE: PRT
<213> ORGANISM: Artificial Sequence
<220> FEATURE:
<223> OTHER INFORMATION: PDH-101 variant

<400> SEQUENCE: 216

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Val
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Leu Ala Met
145                 150                 155                 160

Ala Asp Arg Leu Gln Gly Trp Gly Ala Thr Leu Gln Tyr His Ala Arg
                165                 170                 175

Lys Ala Leu Asp Thr Gln Thr Glu Gln Thr Leu Gly Leu Arg Gln Val
            180                 185                 190

Ala Cys Ser Glu Leu Phe Ala Ser Ser Asp Phe Ile Leu Leu Ala Leu
        195                 200                 205
```

```
Pro Leu Asn Ala Asp Thr Leu His Leu Val Asn Ala Glu Leu Leu Ala
    210                 215                 220

Leu Val Arg Pro Gly Ala Leu Leu Ile Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Ala Gly Glu Arg
305                 310                 315                 320

Pro Ile Asp Ala Val Asn Arg Leu Pro Lys Ala Glu Pro Ala Ala Ser
                325                 330                 335
```

<210> SEQ ID NO 217
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 217

```
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg ctatgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcatt ctgggcatgg cgccatcgg aaaagccatg     480
gctgatcgct tgcagggatg gggcgcgacc ctgcagtacc actcgcggac agctctggat     540
acacaaaccg agcaacggct cggcctgcgc aggtggcgt gcagcgaact cttagccagc     600
tcggacttca tcctgctggc gcttcccttg aatgccgata ccctgcatct ggtcaacgcc     660
gagctgcttg ccctcgtacg gccgggcgct ctgcttgtaa accccgtcg tggctctgta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg     900
cgcctggaga ttgaacgttg tgcagcgcag aacatcctcc aggcattgcg aggtgagcgc     960
ccaattgacg ctgtgaacag cccgcccaag gccgagcctg ccgcatgttg a            1011
```

<210> SEQ ID NO 218
<211> LENGTH: 336
<212> TYPE: PRT
<213> ORGANISM: Artificial Sequence
<220> FEATURE:
<223> OTHER INFORMATION: PDH-101 variant

<400> SEQUENCE: 218

Met Leu Pro Lys Leu Val Ile Thr His Arg Val His Glu Glu Ile Leu

```
1               5                   10                  15
Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Ile Gly Cys Ala Leu Lys Gly Tyr Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
            115                 120                 125

Gly Lys Phe Gln Gly Trp Gln Pro Ile Phe Tyr Gly Thr Gly Leu Asp
        130                 135                 140

Gly Ala Thr Val Gly Ile Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Leu Ala Ser Ser Asp Phe Ile Leu Leu Ala Leu
            195                 200                 205

Pro Leu Asn Ala Asp Thr Leu His Leu Val Asn Ala Glu Leu Leu Ala
        210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
            275                 280                 285

Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
305                 310                 315                 320

Pro Ile Asp Ala Val Asn Ser Pro Pro Lys Ala Glu Pro Ala Ala Cys
                325                 330                 335
```

<210> SEQ ID NO 219
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 219
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240

-continued

```
ttcgatgtgg acgcctgtac tgcacgcggg gtctggctga cctttgtgcc tgatctgttg     300
acggtcccga ctgccgagct ggcgatcgga ctggcgtgg ggctggggcg gcatttccgg      360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg gcggcccaga ccctgcatct ggtcaacgcc   660
gagctgcttg ccctcgtacg gccgggcgct ctgcttgtaa accctgtcg tggctctgta    720 gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900 cgcctggaga ttgaacgttg tgcagcgcag aacatcctcc aggcattgcg aggtgagcgc   960
ccacaagacg ctgtgaaccg tctgcccaag gccgagcctg ccgcatgttg a           1011
```

<210> SEQ ID NO 220
<211> LENGTH: 336
<212> TYPE: PRT
<213> ORGANISM: Artificial Sequence
<220> FEATURE:
<223> OTHER INFORMATION: PDH-101 variant

<400> SEQUENCE: 220

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Ala Ala Gln Thr Leu His Leu Val Asn Ala Glu Leu Leu Ala
    210                 215                 220
```

```
Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Arg Leu Glu Ile
    290                 295                 300

Glu Arg Cys Ala Ala Gln Asn Ile Leu Gln Ala Leu Arg Gly Glu Arg
305                 310                 315                 320

Pro Gln Asp Ala Val Asn Arg Leu Pro Lys Ala Glu Pro Ala Ala Cys
                325                 330                 335
```

<210> SEQ ID NO 221
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 221

```
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga cctttgtgcc tgatctgttg    300
acggtcccga ctgccgagct ggcgatcgga ctggcggtgg ggctggggcg gcatttccgg    360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac ccctctggat    540
acacaaacag agcaacggct cggcctgcgc caggtggcgc ttagcgaact cttcgccagc    600
tcggacttca tcctgctggc gcttcccttg gcggcccaga ccctgcatct ggtcaacgcc    660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggcg    780
gatgtattcg aaatggaaga ctgggctcgc gcggaccggc gcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccacaagacg ctgtgaaccg tctgcccaag gccgagcccg ccgcatgttg a            1011
```

<210> SEQ ID NO 222
<211> LENGTH: 336
<212> TYPE: PRT
<213> ORGANISM: Artificial Sequence
<220> FEATURE:
<223> OTHER INFORMATION: PDH-101 variant

<400> SEQUENCE: 222

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
```

```
                    20                  25                  30
Thr Leu Thr Arg Glu Glu Ile Leu Arg Arg Cys Ala Asp Ala Gln Ala
                35                  40                  45
Met Met Ala Phe Met Pro Asp Arg Val Asp Asp Phe Leu Gln Ala
             50                  55                  60
Cys Pro Glu Leu Arg Val Ile Gly Cys Ala Leu Lys Gly Phe Asp Asn
 65                  70                  75                  80
Phe Asp Val Asp Ala Cys Thr Ala Arg Gly Val Trp Leu Thr Phe Val
                 85                  90                  95
Pro Asp Leu Leu Thr Val Pro Thr Ala Glu Leu Ala Ile Gly Leu Ala
                100                 105                 110
Val Gly Leu Gly Arg His Phe Arg Ala Ala Asp Ala Phe Val Arg Ser
            115                 120                 125
Gly Lys Phe Gln Gly Trp Gln Pro Ile Phe Tyr Gly Thr Gly Leu Asp
        130                 135                 140
Gly Ala Thr Val Gly Phe Leu Gly Met Gly Ala Ile Gly Lys Ala Met
145                 150                 155                 160
Ala Asp Arg Leu Gln Gly Trp Gly Ala Thr Leu Gln Tyr His Ser Arg
                165                 170                 175
Thr Pro Leu Asp Thr Gln Thr Glu Gln Arg Leu Gly Leu Arg Gln Val
            180                 185                 190
Ala Leu Ser Glu Leu Phe Ala Ser Ser Asp Phe Ile Leu Leu Ala Leu
        195                 200                 205
Pro Leu Ala Ala Gln Thr Leu His Leu Val Asn Ala Glu Leu Leu Ala
    210                 215                 220
Leu Val Arg Pro Gly Ala Leu Leu Val Asn Pro Cys Arg Gly Ser Val
225                 230                 235                 240
Val Asp Glu Ala Ala Val Leu Ala Ala Leu Glu Arg Gly Gln Leu Gly
                245                 250                 255
Gly Tyr Ala Ala Asp Val Phe Glu Met Glu Asp Trp Ala Arg Ala Asp
            260                 265                 270
Arg Pro Gln Gln Ile Asp Pro Ala Leu Leu Ala His Pro Asn Thr Leu
        275                 280                 285
Phe Thr Pro His Leu Gly Ser Ala Val Arg Ala Val Arg Leu Glu Ile
    290                 295                 300
Glu Arg Cys Ala Ala Gln Asn Ile Leu Gln Ala Leu Arg Gly Glu Arg
305                 310                 315                 320
Pro Gln Asp Ala Val Asn Arg Leu Pro Lys Ala Glu Pro Ala Ala Cys
                325                 330                 335

<210> SEQ ID NO 223
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 223
atgctgccga aactcgttat aactcacaga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccattgtgcc tgatctgttg    300
```

-continued

```
acggtcccga ctgccgagct ggcgatcgga ctggcggtgg ggctggggcg gcatttccgg    360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgctggc gcttcccttg gcggcccaga ccctgcatct ggtcaacgcc    660
gagctgcttg ccctcgtacg gccgggcgct ctgcttgtaa accccgtcg tggctctgta     720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccaatggacg ctgtgaaccg tctgcccaag gccgagcctg ccgcatgttg a            1011
```

<210> SEQ ID NO 224
<211> LENGTH: 336
<212> TYPE: PRT
<213> ORGANISM: Artificial Sequence
<220> FEATURE:
<223> OTHER INFORMATION: PDH-101 variant

<400> SEQUENCE: 224

```
Met Leu Pro Lys Leu Val Ile Thr His Arg Val His Glu Glu Ile Leu
1               5                   10                  15
Gln Leu Leu Ala Pro His Cys Glu Leu Ile Thr Asn Gln Thr Asp Ser
            20                  25                  30
Thr Leu Thr Arg Glu Glu Ile Leu Arg Arg Cys Ala Asp Ala Gln Ala
        35                  40                  45
Met Met Ala Phe Met Pro Asp Arg Val Asp Ala Asp Phe Leu Gln Ala
    50                  55                  60
Cys Pro Glu Leu Arg Val Ile Gly Cys Ala Leu Lys Gly Phe Asp Asn
65                  70                  75                  80
Phe Asp Val Asp Ala Cys Thr Ala Arg Gly Val Trp Leu Thr Ile Val
                85                  90                  95
Pro Asp Leu Leu Thr Val Pro Thr Ala Glu Leu Ala Ile Gly Leu Ala
            100                 105                 110
Val Gly Leu Gly Arg His Phe Arg Ala Ala Asp Ala Phe Val Arg Ser
        115                 120                 125
Gly Lys Phe Gln Gly Trp Gln Pro Ile Phe Tyr Gly Thr Gly Leu Asp
    130                 135                 140
Gly Ala Thr Val Gly Phe Leu Gly Met Gly Ala Ile Gly Lys Ala Met
145                 150                 155                 160
Ala Asp Arg Leu Gln Gly Trp Gly Ala Thr Leu Gln Tyr His Ser Arg
                165                 170                 175
Thr Ala Leu Asp Thr Gln Thr Glu Gln Arg Leu Gly Leu Arg Gln Val
            180                 185                 190
Ala Cys Ser Glu Leu Phe Ala Ser Ser Asp Phe Ile Leu Leu Ala Leu
        195                 200                 205
Pro Leu Ala Ala Gln Thr Leu His Leu Val Asn Ala Glu Leu Leu Ala
    210                 215                 220
Leu Val Arg Pro Gly Ala Leu Val Asn Pro Cys Arg Gly Ser Val
225                 230                 235                 240
```

Val Asp Glu Ala Ala Val Leu Ala Ala Leu Glu Arg Gly Gln Leu Gly
            245                 250                 255

Gly Tyr Ala Ala Asp Val Phe Glu Met Glu Asp Trp Ala Arg Ala Asp
        260                 265                 270

Arg Pro Gln Gln Ile Asp Pro Ala Leu Leu Ala His Pro Asn Thr Leu
            275                 280                 285

Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
305                 310                 315                 320

Pro Met Asp Ala Val Asn Arg Leu Pro Lys Ala Glu Pro Ala Ala Cys
            325                 330                 335

<210> SEQ ID NO 225
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 225
atgctgccga aactcgttat aactcacaga gtacacgaag agatcctgca actgctggcg      60
ccacattgcg agctgataac caaccagacc gacgtcacgc tgacgcgcga ggaaattctg     120
cggcgctgtg cagatgctca ggcgatgatg gcgttcatgc ccgatcgggt cgatatggac     180
tttcttcaag cctgccctga gctgagagta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg acatttccgg     360
gcagcagatg aattcgtccg ctctggcaag ttccagggct ggcagccaat tttctacggc     420
acggggctgg atggagcaac ggtcggcttc cttggcatgg gcgccatcgg aaaagccatg     480
gctgatcgct gcagggatgg ggcgcgacc ctgcagtacc actcgcggag cgctctggat     540
acacaaaccg agcaacggct cggcctgcgc catgtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctctgta      720 gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg      900 cgcctggaga ttgaacgttg tgcagcgcag aacatcctcc aggcattgcg aggtgagcgc     960
ccaattgacg ctgtgaacga tctgcccaag gccgagcctg ccgcatgttg a              1011

<210> SEQ ID NO 226
<211> LENGTH: 336
<212> TYPE: PRT
<213> ORGANISM: Artificial Sequence
<220> FEATURE:
<223> OTHER INFORMATION: PDH-101 variant

<400> SEQUENCE: 226

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Val
            20                  25                  30

Thr Leu Thr Arg Glu Glu Ile Leu Arg Arg Cys Ala Asp Ala Gln Ala

```
            35                  40                  45
Met Met Ala Phe Met Pro Asp Arg Val Asp Met Asp Phe Leu Gln Ala
         50                  55                  60

Cys Pro Glu Leu Arg Val Ile Gly Cys Ala Leu Lys Gly Phe Asp Asn
 65                  70                  75                  80

Phe Asp Val Asp Ala Cys Thr Ala Arg Gly Val Trp Leu Thr Phe Val
                 85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Glu Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Ser Ala Leu Asp Thr Gln Thr Glu Gln Arg Leu Gly Leu Arg His Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Asp Leu Pro Lys Ala Glu Pro Ala Ala Cys
                325                 330                 335
```

<210> SEQ ID NO 227
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 227

| | | | | |
|---|---|---|---|---|
| atgctgccga aactcgttat aactcacaga gtacacgaag agatcctgca actgctggcg | 60 |
| ccacattgcg agctgataac caaccagacc gacagcacgc tgacgcgcga ggaaattctg | 120 |
| cggcgctgtg cagatgctca ggcgatgatg gcgttcatgc ccgatcgggt cgatgcagac | 180 |
| tttcttcaag cctgccctga gctgcgtgta atcggctgtg cgctcaaggg cttcgacaat | 240 |
| ttcgatgtgg acgcctgtac tgcacgcggg gtctggctga ccttcgtgcc tgatctgttg | 300 |
| acggtcccga ctgccgagct ggcgatcgga ctggcggtgg ggctggggcg gcatttccgg | 360 |
| gcagcagatg cattcgtccg ctctggcaag ttccagggct ggcagccaat tttctacggc | 420 |

```
acgggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgctggc gcttcccttg aatgccgata ccccgcatct ggtcaacgcc    660
gagctgcttg ccctcgtacg gccgggcgct ctgcttgtaa accccgtcg tggctctgta    720 gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg gtcggcagt gcgcgcggtg    900 cgcctggaga ttgaacgttg tgcagcgcag aacatcctcc aggcattgcg aggtgagcgc    960
ccaattgacg ctgtgaaccg tctgcccaag gccgagcctg ccgcatgttg a           1011
```

<210> SEQ ID NO 228
<211> LENGTH: 336
<212> TYPE: PRT
<213> ORGANISM: Artificial Sequence
<220> FEATURE:
<223> OTHER INFORMATION: PDH-101 variant

<400> SEQUENCE: 228

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Pro His Leu Val Asn Ala Glu Leu Leu Ala
    210                 215                 220

Leu Val Arg Pro Gly Ala Leu Val Asn Pro Cys Arg Gly Ser Val
225                 230                 235                 240

Val Asp Glu Ala Ala Val Leu Ala Leu Glu Arg Gly Gln Leu Gly
                245                 250                 255
```

```
Gly Tyr Ala Ala Asp Val Phe Glu Met Glu Asp Trp Ala Arg Ala Asp
                260                 265                 270

Arg Pro Gln Gln Ile Asp Pro Ala Leu Leu Ala His Pro Asn Thr Leu
            275                 280                 285

Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 229
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 229
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc actcgcggac agctctggat     540
acacaaaccg agcaacggct cggcctgcgc caggtggcgt gcagcgaact cttcgccagc     600
tcggacttca tcctgaatgc gcttcccttg aatgccgata ccctgcatct ggtcaacgcc     660
gagctgcttg ccctcgtacg gccgggcgct ctgcttgtaa accctgtcg tggctctgta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg     900
cgcctggaga ttgaacgttg tgcagcgcag aacatcctcc aggcattgcg aggtgagcgc     960
ccaattgacg ctgtgaaccg tctgcccaag gccgagcctg ccgcatgttg a            1011

<210> SEQ ID NO 230
<211> LENGTH: 336
<212> TYPE: PRT
<213> ORGANISM: Artificial Sequence
<220> FEATURE:
<223> OTHER INFORMATION: PDH-101 variant

<400> SEQUENCE: 230

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Ala Asp Ala Gln Ala
            35                  40                  45

Met Met Ala Phe Met Pro Asp Arg Val Asp Ala Asp Phe Leu Gln Ala
```

|   |   |   |   | 50 |   |   |   |   | 55 |   |   |   |   | 60 |   |

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Asn Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 231
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 231
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtga acgcctgtac tgcacgcggg gtctggctga ccttcgtgcc tgatctgttg     300
acggtcccgt tgccgagctg gcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480

```
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtaa accccgtcg tggctctgta    720 gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg gtcggcagt gcgcgcggtg    900 cgcctggaga ttgaacgttg tgcagcgcag aacatcctcc aggcattgcg aggtgagcgc    960
ccaattgacg ctgtgaaccg tctgcccaag gccgagcctg ccgcatgttg a            1011
```

<210> SEQ ID NO 232
<211> LENGTH: 336
<212> TYPE: PRT
<213> ORGANISM: Artificial Sequence
<220> FEATURE:
<223> OTHER INFORMATION: PDH-101 variant

<400> SEQUENCE: 232

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Phe Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270
```

```
Arg Pro Gln Gln Ile Asp Pro Ala Leu Leu Ala His Pro Asn Thr Leu
            275                 280                 285

Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 233
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 233
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccgc ttgccgagct ggcgatcgga ctggcggtgg ggctggggcg gcatttccgg   360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtcg tggctctgta    720 gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900 cgcctggaga ttgaacgttg tgcagcgcag aacatcctcc aggcattgcg aggtgagcgc   960
ccaattgacg ctgtgaaccg tctgcccaag gccgagcctg ccgcatgttg a           1011

<210> SEQ ID NO 234
<211> LENGTH: 336
<212> TYPE: PRT
<213> ORGANISM: Artificial Sequence
<220> FEATURE:
<223> OTHER INFORMATION: PDH-101 variant

<400> SEQUENCE: 234

Met Leu Pro Lys Leu Val Ile Thr His Arg Val His Glu Glu Ile Leu
1               5                  10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
```

```
          65                  70                  75                  80
    Phe Asp Val Asp Ala Cys Thr Ala Arg Gly Val Trp Leu Thr Phe Val
                        85                  90                  95

Pro Asp Leu Leu Thr Val Pro Leu Ala Glu Leu Ala Ile Gly Leu Ala
                    100                 105                 110

Val Gly Leu Gly Arg His Phe Arg Ala Ala Asp Ala Phe Val Arg Ser
                115                 120                 125

Gly Lys Phe Gln Gly Trp Gln Pro Ile Phe Tyr Gly Thr Gly Leu Asp
            130                 135                 140

Gly Ala Thr Val Gly Phe Leu Gly Met Gly Ala Ile Gly Lys Ala Met
    145                 150                 155                 160

Ala Asp Arg Leu Gln Gly Trp Gly Ala Thr Leu Gln Tyr His Ser Arg
                    165                 170                 175

Thr Ala Leu Asp Thr Gln Thr Glu Gln Arg Leu Gly Leu Arg Gln Val
                180                 185                 190

Ala Cys Ser Glu Leu Phe Ala Ser Ser Asp Phe Ile Leu Leu Ala Leu
            195                 200                 205

Pro Leu Asn Ala Asp Thr Leu His Leu Val Asn Ala Glu Leu Leu Ala
        210                 215                 220

Leu Val Arg Pro Gly Ala Leu Leu Val Asn Pro Cys Arg Gly Ser Val
    225                 230                 235                 240

Val Asp Glu Ala Ala Val Leu Ala Ala Leu Glu Arg Gly Gln Leu Gly
                    245                 250                 255

Gly Tyr Ala Ala Asp Val Phe Glu Met Glu Asp Trp Ala Arg Ala Asp
                260                 265                 270

Arg Pro Gln Gln Ile Asp Pro Ala Leu Leu Ala His Pro Asn Thr Leu
            275                 280                 285

Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
    305                 310                 315                 320

Pro Ile Asp Ala Val Asn Arg Leu Pro Lys Ala Glu Pro Ala Ala Cys
                    325                 330                 335

<210> SEQ ID NO 235
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 235
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc actcgcggac agctctggat     540
acacaaaccg agcaacggct cggcctgcgc caggtggcgt gcagcgaact cttcgccagc     600
```

```
tcggacttca tcctgctggc gcttcccttg aatgccgata ccctgcatct ggtcaacgcc    660
gagctgcttg ccctcgtacg gccgggcgct ctgcttgtaa acccctgtcg tggctctgta    720
gtggatgaag ccgccgtgct cgcggcgctt gagcgaggcc agctcggcgg tatgcggcg     780 gatgtattcg aaatgtctga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgttg a            1011
```

<210> SEQ ID NO 236
<211> LENGTH: 336
<212> TYPE: PRT
<213> ORGANISM: Artificial Sequence
<220> FEATURE:
<223> OTHER INFORMATION: PDH-101 variant

<400> SEQUENCE: 236

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Ser Asp Trp Ala Arg Ala Asp
            260                 265                 270

Arg Pro Gln Gln Ile Asp Pro Ala Leu Leu Ala His Pro Asn Thr Leu
        275                 280                 285
```

```
Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 237
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 237
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg gctggggcg catttccgg      360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc actcgcggac agctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctctgta      720
gtggatgaag ccgccgtgct cgcggcgctt gagcgaggcc agctcggcgg gtatgcggcg     780
gatcctttcg aaatggaaga ctgggctcgc gcggaccggc cgcagcagat cgatcctgcg     840
ctgctcgcgc atccgaatac gctgttcact ccgcaccttg ggtcggcagt gcgcgcggtg     900
cgcctggaga ttgaacgttg tgcagcgcag aacatcctcc aggcattgcg aggtgagcgc     960
ccaattgacg ctgtgaaccg tctgcccaag gccgagcctg ccgcatgttg a             1011

<210> SEQ ID NO 238
<211> LENGTH: 336
<212> TYPE: PRT
<213> ORGANISM: Artificial Sequence
<220> FEATURE:
<223> OTHER INFORMATION: PDH-101 variant

<400> SEQUENCE: 238

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
```

```
                85                  90                  95
Pro Asp Leu Leu Thr Val Pro Thr Ala Glu Leu Ala Ile Gly Leu Ala
                100                 105                 110
Val Gly Leu Gly Arg His Phe Arg Ala Ala Asp Ala Phe Val Arg Ser
            115                 120                 125
Gly Lys Phe Gln Gly Trp Gln Pro Ile Phe Tyr Gly Thr Gly Leu Asp
        130                 135                 140
Gly Ala Thr Val Gly Phe Leu Gly Met Gly Ala Ile Gly Lys Ala Met
145                 150                 155                 160
Ala Asp Arg Leu Gln Gly Trp Gly Ala Thr Leu Gln Tyr His Ser Arg
                165                 170                 175
Thr Ala Leu Asp Thr Gln Thr Glu Gln Arg Leu Gly Leu Arg Gln Val
                180                 185                 190
Ala Cys Ser Glu Leu Phe Ala Ser Ser Asp Phe Ile Leu Leu Ala Leu
            195                 200                 205
Pro Leu Asn Ala Asp Thr Leu His Leu Val Asn Ala Glu Leu Leu Ala
        210                 215                 220
Leu Val Arg Pro Gly Ala Leu Leu Val Asn Pro Cys Arg Gly Ser Val
225                 230                 235                 240
Val Asp Glu Ala Ala Val Leu Ala Ala Leu Glu Arg Gly Gln Leu Gly
                245                 250                 255
Gly Tyr Ala Ala Asp Pro Phe Glu Met Glu Asp Trp Ala Arg Ala Asp
                260                 265                 270
Arg Pro Gln Gln Ile Asp Pro Ala Leu Leu Ala His Pro Asn Thr Leu
            275                 280                 285
Phe Thr Pro His Leu Gly Ser Ala Val Arg Ala Val Arg Leu Glu Ile
        290                 295                 300
Glu Arg Cys Ala Ala Gln Asn Ile Leu Gln Ala Leu Arg Gly Glu Arg
305                 310                 315                 320
Pro Ile Asp Ala Val Asn Arg Leu Pro Lys Ala Glu Pro Ala Ala Cys
                325                 330                 335
```

<210> SEQ ID NO 239
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 239

```
atgctgccga aactcgttat aactcacaga gtacacgaag agatcctgca actgctggcg     60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg ggctggggcg gcatttccgg   360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
```

```
gagctgcttg ccctcgtacg gccgggcgct ctgcttgtaa acccctgtcg tggctctgta    720
gtggatgaag ccgccgtgct cgcggcgctt gagcgaggcc agctcggcgg gtatgcggcg    780
gatgatttcg aaatggaaga ctgggctcgc gcggaccggc cgcagcagat cgatcctgcg    840
ctgctcgcgc atccgaatac gctgttcact ccgcaccttg gtcggcagt gcgcgcggtg     900 cgcctggaga ttgaacgttg tgcagcgcag aacatcctcc aggcattgcg aggtgagcgc    960
ccaattgacg ctgtgaaccg tctgcccaag gccgagcctg ccgcatgttg a            1011
```

<210> SEQ ID NO 240
<211> LENGTH: 336
<212> TYPE: PRT
<213> ORGANISM: Artificial Sequence
<220> FEATURE:
<223> OTHER INFORMATION: PDH-101 variant

<400> SEQUENCE: 240

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Asp Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300
```

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 241
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 241

| | |
|---|---|
| atgctgccga aactcgttat aactcacaga gtacacgaag agatcctgca actgctggcg | 60 |
| ccacattgcg agctgataac caaccagacc gacagcacgc tgacgcgcga ggaaattctg | 120 |
| cggcgctgtg cagatgctca ggcgatgatg gcgttcatgc cgatcgggt cgatgcagac | 180 |
| tttcttcaag cctgccctga gctgcgtgta atcggctgtg cgctcaaggg cttcgacaat | 240 |
| ttcgatgcgg acgcctgtac tgcacgcggg gtctggctga ccttcgtgcc tgatctgttg | 300 |
| acggtcccga ctgccgagct ggcgatcgga ctggcggtgg ggctggggcg gcatttccgg | 360 |
| gcagcagatg cattcgtccg ctctggcaag ttccagggct ggcagccaat tttctacggc | 420 |
| acggggctgg atggagcaac ggtcggcttc cttggcatgg gcgccatcgg aaaagccatg | 480 |
| gctgatcgct tgcagggatg gggcgcgacc ctgcagtacc actcgcggac agctctggat | 540 |
| acacaaaccg agcaacggct cggcctgcgc caggtggcgt gcagcgaact cttcgccagc | 600 |
| tcggacttca tcctgctggc gcttcccttg aatgccgata ccctgcatct ggtcaacgcc | 660 |
| gagctgcttg ccctcgtacg gccgggcgct ctgcttgtaa accctgtcg tggctctgta | 720 |
| gtggatgaag ccgccgtgct cgcggcgctt gagcgaggcc agctcggcgg gtatgcggcg | 780 |
| gatgtattcg aaatggcgga ctgggctcgc gcggaccggc cgcagcagat cgatcctgcg | 840 |
| ctgctcgcgc atccgaatac gctgttcact ccgcaccttg gtcggcagt gcgcgcggtg | 900 |
| cgcctggaga ttgaacgttg tgcagcgcag aacatcctcc aggcattgcg aggtgagcgc | 960 |
| ccaattgacg ctgtgaaccg tctgcccaag gccgagcctg ccgcatgttg a | 1011 |

<210> SEQ ID NO 242
<211> LENGTH: 336
<212> TYPE: PRT
<213> ORGANISM: Artificial Sequence
<220> FEATURE:
<223> OTHER INFORMATION: PDH-101 variant

<400> SEQUENCE: 242

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Ala Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Ile Gly Cys Ala Leu Lys Gly Phe Asp Asn
65                  70                  75                  80

Phe Asp Ala Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala

```
            100                 105                 110
Val Gly Leu Gly Arg His Phe Arg Ala Ala Asp Ala Phe Val Arg Ser
            115                 120                 125

Gly Lys Phe Gln Gly Trp Gln Pro Ile Phe Tyr Gly Thr Gly Leu Asp
        130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Ala Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335
```

<210> SEQ ID NO 243
<211> LENGTH: 1011
<212> TYPE: DNA
<213> ORGANISM: Artificial Sequence
<220> FEATURE:
<223> OTHER INFORMATION: PDH-101 variant

<400> SEQUENCE: 243

```
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gctggggcg gcatttccgg   360 gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtgcg tggctctgta   720
gtggatgaag ccgccgtgct cgcggcgctt gagcgaggcc agctcggcgg gtatgcggcg   780
```

```
gatgtattcg aaatggaaga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccaattaatg cggtgaaccg tctgcccaag gccgagcctg ccgcatgttg a            1011
```

<210> SEQ ID NO 244
<211> LENGTH: 336
<212> TYPE: PRT
<213> ORGANISM: Artificial Sequence
<220> FEATURE:
<223> OTHER INFORMATION: PDH-101 variant

<400> SEQUENCE: 244

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
                20                  25                  30

Thr Leu Thr Arg Glu Glu Ile Leu Arg Arg Cys Ala Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320
```

```
Pro Ile Asn Ala Val Asn Arg Leu Pro Lys Ala Glu Pro Ala Ala Cys
            325                 330                 335
```

<210> SEQ ID NO 245
<211> LENGTH: 1008
<212> TYPE: DNA
<213> ORGANISM: Artificial Sequence
<220> FEATURE:
<223> OTHER INFORMATION: PDH-101 variant

<400> SEQUENCE: 245

```
atgctgccga aactcgttat aactcacaga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgcgg acgcctgtac tgcacgcggg gtctggctga ccttcgtgcc tgatctgttg    300
acggtcccgt tggccgagct ggcgatcgga ctggcggtgg ggctggggcg gcatttccgg    360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgaatgc gcttcccttg aatgccgata ccctgcatct ggtcaacgcc    660
gagctgcttg ccctcgtacg gccgggcgct ctgcttgtaa accccgtgcg tggctctgta    720
gtggatgaag ccgccgtgct cgcggcgctt gagcgaggcc agctcggcgg gtatgcggcg    780
gatgtgttcg aaatggagga ctgggctcgc gcggaccggc cgcagcagat cgatcctgcg    840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgt             1008
```

<210> SEQ ID NO 246
<211> LENGTH: 336
<212> TYPE: PRT
<213> ORGANISM: Artificial Sequence
<220> FEATURE:
<223> OTHER INFORMATION: PDH-101 variant

<400> SEQUENCE: 246

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Ala Asp Ala Cys Thr Ala Arg Gly Val Trp Leu Thr Phe Val
                85                  90                  95

Pro Asp Leu Leu Thr Val Pro Leu Ala Glu Leu Ala Ile Gly Leu Ala
            100                 105                 110

Val Gly Leu Gly Arg His Phe Arg Ala Ala Asp Ala Phe Val Arg Ser
```

```
                    115                 120                 125
Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Asn Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 247
<211> LENGTH: 1008
<212> TYPE: DNA
<213> ORGANISM: Artificial Sequence
<220> FEATURE:
<223> OTHER INFORMATION: PDH-101 variant

<400> SEQUENCE: 247
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgta ccctcaaggg cttcgacaat     240
ttcgatgcgg acgcctgtac tgcacgcggg gtctggctga ccttcgtgcc tgatctgttg     300
acggtcccga ctgccgagct ggcgatcgga ctggcggtgg gctggggcg  gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc actcgcggac agctctggat     540
acacaaaccg agcaacggct cggcctgcgc caggtggcgt gcagcgaact cttcgccagc     600
tcggacttca tcctgaatgc gcttcccttg aatgccgata ccctgcatct ggtcaacgcc     660
gagctgcttg ccctcgtacg gccgggcgct ctgcttgtaa accccgtcg  tggctctgta     720
gtggatgaag ccgccgtgct cgcggcgctt gagcgaggcc agctcggcgg gtatgcggcg     780
gatgtgttcg aaatggagga ctgggctcgc gcggaccggc cgcagcagat cgatcctgcg     840
```

```
ctgctcgcgc atccgaatac gctgttcact ccgcaccttg ggtcggcagt gcgcgcggtg      900
cgcctggaga ttgaacgttg tgcagcgcag aacatcctcc aggcattgcg aggtgagcgc      960
ccaattgacg ctgtgaaccg tctgcccaag gccgagcctg ccgcatgt                  1008
```

<210> SEQ ID NO 248
<211> LENGTH: 336
<212> TYPE: PRT
<213> ORGANISM: Artificial Sequence
<220> FEATURE:
<223> OTHER INFORMATION: PDH-101 variant

<400> SEQUENCE: 248

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Thr Leu Lys Gly Phe Asp Asn
65                  70                  75                  80

Phe Asp Ala Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Asn Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335
```

<210> SEQ ID NO 249
<211> LENGTH: 1008
<212> TYPE: DNA
<213> ORGANISM: Artificial Sequence
<220> FEATURE:
<223> OTHER INFORMATION: PDH-101 variant

<400> SEQUENCE: 249

```
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc cgatcgggt cgatgcagac      180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccgt tggccgagct ggcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct gcagggatg gggcgcgacc ctgcagtacc actcgcggac agctctggat     540
acacaaaccg agcaacggct cggcctgcgc aggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accccgtcg tggctctgta     720
gtggatgaag ccgccgtgct cgcggcgctt gagcgaggcc agctcggcgg gtatgcggcg     780
gatctgttcg aaatggagga ctgggctcgc gcggaccggc cgcagcagat cgatcctgcg     840
ctgctcgcgc atccgaatac gctgttcact ccgcaccttg ggtcggcagt gcgcgcggtg     900
cgcctggaga ttgaacgttg tgcagcgcag aacatcctcc aggcattgcg aggtgagcgc     960
ccaattgacg ctgtgaaccg tctgcccaag gccgagcctg ccgcatgt              1008
```

<210> SEQ ID NO 250
<211> LENGTH: 336
<212> TYPE: PRT
<213> ORGANISM: Artificial Sequence
<220> FEATURE:
<223> OTHER INFORMATION: PDH-101 variant

<400> SEQUENCE: 250

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Leu Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
```

```
                130                 135                 140
Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Leu Phe Glu Met Glu Asp Trp Ala Arg Ala Asp
                260                 265                 270

Arg Pro Gln Gln Ile Asp Pro Ala Leu Leu His Pro Asn Thr Leu
            275                 280                 285

Phe Thr Pro His Leu Gly Ser Ala Val Arg Ala Val Arg Leu Glu Ile
        290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 251
<211> LENGTH: 1008
<212> TYPE: DNA
<213> ORGANISM: Artificial Sequence
<220> FEATURE:
<223> OTHER INFORMATION: PDH-101 variant

<400> SEQUENCE: 251
atgctgccga aactcgttat aactcacaga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg ccctcaaggg cttcgacaat    240
ttcgatgtgg acgcctgtac tgcacgcggg gtctggctga ccttcgtgcc tgatctgttg    300
acggtcccgt tggccgagct ggcgatcgga ctggcggtgg ggctggggcg gcatttccgg    360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct gcagggatg gggcgcgacc ctgcagtacc actcgcggac agctctggat    540
acacaaaccg agcaacggct cggcctgcgc caggtgcgt gcagcgaact cttcgccagc    600
tcggacttca tcctgaatgc gcttcccttg aatgccgata ccctgcatct ggtcaacgcc    660
gagctgcttg ccctcgtacg gccgggcgct ctgcttgtaa accccgtgcg tggctctgta    720
gtggatgaag ccgccgtgct cgcggcgctt gagcgaggcc agctcggcgg gtatgcggcg    780
gatgtgttcg aaatggagga ctgggctcgc gcggaccggc cgcagcagat cgatcctgcg    840
ctgctcgcgc atccgaatac gctgttcact ccgcaccttg gtcggcagt gcgcgcggtg    900 cgcctggaga ttgaacgttg tgcagcgcag aacatcctcc aggcattgcg aggtgagcgc    960
```

```
ccaattgacg ctgtgaaccg tctgcccaag gccgagcctg ccgcatgt            1008
```

<210> SEQ ID NO 252
<211> LENGTH: 336
<212> TYPE: PRT
<213> ORGANISM: Artificial Sequence
<220> FEATURE:
<223> OTHER INFORMATION: PDH-101 variant

<400> SEQUENCE: 252

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Leu Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Asn Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335
```

<210> SEQ ID NO 253
<211> LENGTH: 1008

```
<212> TYPE: DNA
<213> ORGANISM: Artificial Sequence
<220> FEATURE:
<223> OTHER INFORMATION: PDH-101 variant

<400> SEQUENCE: 253
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg ggctggggcg gcatttccgg     360
gcagcagatg cattcgtccg ctctggcaag ttccagggct ggcagccaat ttttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtaa accccgtcg tggctctgta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg gcgggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgt                 1008

<210> SEQ ID NO 254
<211> LENGTH: 336
<212> TYPE: PRT
<213> ORGANISM: Artificial Sequence
<220> FEATURE:
<223> OTHER INFORMATION: PDH-101 variant

<400> SEQUENCE: 254

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
```

```
                145                 150                 155                 160
Ala Asp Arg Leu Gln Gly Trp Gly Ala Thr Leu Gln Tyr His Ser Arg
                    165                 170                 175

Thr Ala Leu Asp Thr Gln Thr Glu Gln Arg Leu Gly Leu Arg Gln Val
                    180                 185                 190

Ala Cys Ser Glu Leu Phe Ala Ser Ser Asp Phe Ile Leu Leu Ala Leu
                    195                 200                 205

Pro Leu Asn Ala Asp Thr Leu His Leu Val Asn Ala Glu Leu Leu Ala
            210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                    245                 250                 255

Gly Tyr Ala Ala Asp Val Phe Glu Met Glu Asp Trp Ala Arg Ala Asp
                    260                 265                 270

Arg Pro Gln Gln Ile Asp Pro Ala Leu Leu Ala His Pro Asn Thr Leu
                    275                 280                 285

Phe Thr Pro His Leu Gly Arg Ala Val Arg Ala Val Arg Leu Glu Ile
            290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                    325                 330                 335

<210> SEQ ID NO 255
<211> LENGTH: 1008
<212> TYPE: DNA
<213> ORGANISM: Artificial Sequence
<220> FEATURE:
<223> OTHER INFORMATION: PDH-101 variant

<400> SEQUENCE: 255
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgggcc tgatctgttg     300
acggtcccga ctgccgagct ggcgatcgga ctggcggtgg gctggggcg gcatttccgg      360 gcagcagatg cattcgtccg ctctggcaag ttccagggct ggcagccaat tttctacggc     420
acggggctgg atggagcaac ggtcggcttc cttggcatgg cgccatcgg aaaagccatg      480 gctgatcgct tgcagggatg gggcgcgacc ctgcagtacc actcgcggac agctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctctgta      720 gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg     900 cgcctggaga ttgaacgttg tgcagcgcag aacatcctcc aggcattgcg aggtgagcgc     960
ccaattgacg ctgtgaaccg tctgcccaag gccgagcctg ccgcatgt              1008
```

```
<210> SEQ ID NO 256
<211> LENGTH: 336
<212> TYPE: PRT
<213> ORGANISM: Artificial Sequence
<220> FEATURE:
<223> OTHER INFORMATION: PDH-101 variant

<400> SEQUENCE: 256

Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Gly
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335

<210> SEQ ID NO 257
<211> LENGTH: 1008
<212> TYPE: DNA
<213> ORGANISM: Artificial Sequence
<220> FEATURE:
```

<223> OTHER INFORMATION: PDH-101 variant

<400> SEQUENCE: 257

```
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga tggccgagct ggcgatcgga ctggcggtgg ggctggggcg gcatttccgg     360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc actcgcggac agctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accctgtcg tggctctgta     720
gtggatgaag ccgccgtgct cgcggcgctt gagcgaggcc agctcggcgg gtatgcggcg     780
gatgtattcg aaatgaaga ctgggctcgc gcggaccggc cgcagcagat cgatcctgcg     840
ctgctcgcgc atccgaatac gctgttcact ccgcaccttg gtcggcagt gcgcgcggtg     900
cgcctggaga ttgaacgttg tgcagcgcag aacatcctcc aggcattgcg aggtgagcgc     960
ccaattgacg ctgtgaaccg tctgcccaag gccgagcctg ccgcatgt              1008
```

<210> SEQ ID NO 258
<211> LENGTH: 336
<212> TYPE: PRT
<213> ORGANISM: Artificial Sequence
<220> FEATURE:
<223> OTHER INFORMATION: PDH-101 variant

<400> SEQUENCE: 258

```
Met Leu Pro Lys Leu Val Ile Thr His Arg Val His Glu Glu Ile Leu
1               5                  10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Met Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Ser Arg
```

165                 170                 175
Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
            195                 200                 205

Pro Leu Asn Ala Asp Thr Leu His Leu Val Asn Ala Glu Leu Leu Ala
            210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
            245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
            275                 280                 285

Phe Thr Pro His Leu Gly Ser Ala Val Arg Ala Val Arg Leu Glu Ile
            290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
            325                 330                 335

<210> SEQ ID NO 259
<211> LENGTH: 1008
<212> TYPE: DNA
<213> ORGANISM: Artificial Sequence
<220> FEATURE:
<223> OTHER INFORMATION: PDH-101 variant

<400> SEQUENCE: 259
atgctgccga aactcgttat aactcacaga gtacacgaag agatcctgca actgctggcg      60
ccacattgcg agctgataac caaccagacc gacagcacgc tgacgcgcga ggaaattctg     120
cggcgctgtg cagatgctca ggcgatgatg gcgttcatgc ccgatcgggt cgatgcagac     180
tttcttcaag cctgccctga gctgcgtgta atcggctgtg cgctcaaggg cttcgacaat     240
ttcgatgtgg acgcctgtac tgcacgcggg gtctggctga ccttcgtgcc tgatctgttg     300
acggtcccga ctgccgagct ggcgatcgga ctggcggtgg gctggggcg gcatttccgg      360
gcagcagatg cattcgtccg ctctggcaag ttccagggct ggcagccaat tttctacggc     420
acggggctgg atggagcaac ggtcggcttc cttggcatgg gcgccatcgg aaaagccatg     480
gctgatcgct tgcagggatg gggcgcgacc ctgcagtacc acgaagcgac agctctggat     540
acacaaaccg agcaacggct cggcctgcgc caggtggcgt gcagcgaact cttcgccagc     600
tcggacttca tcctgctggc gcttcccttg aatgccgata ccctgcatct ggtcaacgcc     660
gagctgcttg ccctcgtacg gccgggcgct ctgcttgtaa accccgtcg tggctctgta     720
gtggatgaag ccgccgtgct cgcggcgctt gagcgaggcc agctcggcgg gtatgcggcg     780
gatgtattcg aaatggaaga ctgggctcgc gcggaccggc cgcagcagat cgatcctgcg     840
ctgctcgcgc atccgaatac gctgttcact ccgcaccttg gtcggcagt gcgcgcggtg     900
cgcctggaga ttgaacgttg tgcagcgcag aacatcctcc aggcattgcg aggtgagcgc     960
ccaattgacg ctgtgaaccg tctgcccaag gccgagcctg ccgcatgt                1008

<210> SEQ ID NO 260
<211> LENGTH: 336

<212> TYPE: PRT
<213> ORGANISM: Artificial Sequence
<220> FEATURE:
<223> OTHER INFORMATION: PDH-101 variant

<400> SEQUENCE: 260

```
Met Leu Pro Lys Leu Val Ile Thr His Arg Val His Glu Glu Ile Leu
1               5                   10                  15

Gln Leu Leu Ala Pro His Cys Glu Leu Ile Thr Asn Gln Thr Asp Ser
            20                  25                  30

Thr Leu Thr Arg Glu Glu Ile Leu Arg Arg Cys Ala Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Ile Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Phe Arg Ala Ala Asp Ala Phe Val Arg Ser
        115                 120                 125

Gly Lys Phe Gln Gly Trp Gln Pro Ile Phe Tyr Gly Thr Gly Leu Asp
    130                 135                 140

Gly Ala Thr Val Gly Phe Leu Gly Met Gly Ala Ile Gly Lys Ala Met
145                 150                 155                 160

Ala Asp Arg Leu Gln Gly Trp Gly Ala Thr Leu Gln Tyr His Glu Ala
                165                 170                 175

Thr Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Leu His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Gln Gln Ile Asp Pro Ala Leu Leu Ala His Pro Asn Thr Leu
        275                 280                 285

Phe Thr Pro His Leu Gly Ser Ala Val Arg Ala Val Arg Leu Glu Ile
    290                 295                 300

Glu Arg Cys Ala Ala Gln Asn Ile Leu Gln Ala Leu Arg Gly Glu Arg
305                 310                 315                 320

Pro Ile Asp Ala Val Asn Arg Leu Pro Lys Ala Glu Pro Ala Ala Cys
                325                 330                 335
```

KETOREDUCTASE POLYPEPTIDES AND POLYNUCLEOTIDES

The present application is Divisional of co-pending of U.S. patent application Ser. No. 16/605,576, filed Oct. 16, 2019, a national stage application filed under 35 USC § 371 and claims priority to international application to PCT International Application No. PCT/US2018/027450, filed Apr. 13, 2018, which claims priority to U.S. Prov. Pat. Appln. Ser. No. 62/491,161, filed Apr. 27, 2017, all of which are hereby incorporated by reference, in their entireties and for all purposes.

REFERENCE TO SEQUENCE LISTING, TABLE OR COMPUTER PROGRAM

The Sequence Listing concurrently submitted herewith under 37 C.F.R. § 1.821 in a computer readable form (CRF) via EFS-Web as file name CX2-166USP1_Corrected_ST25.txt is herein incorporated by reference. The electronic copy of the Sequence Listing was created on Oct. 8, 2019, with a file size of 544 Kbytes.

FIELD OF THE INVENTION

The present invention provides engineered ketoreductase and phosphite dehydrogenase enzymes having improved properties as compared to a naturally occurring wild-type ketoreductase and phosphite dehydrogenase enzymes, as well as polynucleotides encoding the engineered ketoreductase and phosphite dehydrogenase enzymes, host cells capable of expressing the engineered ketoreductase and phosphite dehydrogenase enzymes, and methods of using the engineered ketoreductase and phosphite dehydrogenase enzymes to synthesize a chiral catalyst used in the synthesis of antiviral compounds, such as nucleoside inhibitors. The present invention further provides methods of using the engineered enzymes to deracemize a chiral alcohol in a one-pot, multi-enzyme system.

BACKGROUND

Enzymes belonging to the ketoreductase (KRED) or carbonyl reductase class (EC1.1.1.184) are useful for the synthesis of optically active alcohols from the corresponding prochiral ketone substrate and by stereoselective reduction of corresponding racemic aldehyde substrates. KREDs typically convert ketone and aldehyde substrates to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state), but most often not both.

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic ketone and aldehyde reductions or for biocatalytic alcohol oxidation, or by use of purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase, phosphite dehydrogenase etc. can be used in conjunction with the ketoreductase. It is desirable to identify other ketoreductase enzymes that can be used to carryout conversion of various keto substrates to corresponding chiral alcohol products or conversion of various alcohol substrates to corresponding ketone products.

SUMMARY OF THE INVENTION

The present invention provides engineered ketoreductase and phosphite dehydrogenase enzymes having improved properties as compared to a naturally occurring wild-type ketoreductase and phosphite dehydrogenase enzymes, as well as polynucleotides encoding the engineered ketoreductase and phosphite dehydrogenase enzymes, host cells capable of expressing the engineered ketoreductase and phosphite dehydrogenase enzymes, and methods of using the engineered ketoreductase and phosphite dehydrogenase enzymes to synthesize a chiral catalyst used in the synthesis of antiviral compounds, such as nucleoside inhibitors. The present invention further provides methods of using the engineered enzymes to deracemize a chiral alcohol in a one-pot, multi-enzyme system.

In addition, the present invention provides engineered phosphite dehydrogenase enzymes having improved properties as compared to a naturally occurring wild-type phosphite dehydrogenase enzyme, as well as polynucleotides encoding the engineered phosphite dehydrogenase enzymes, host cells capable of expressing the engineered phosphite dehydrogenase enzymes, and methods of using the engineered phosphite dehydrogenase enzymes to deracemize a chiral alcohol in a one-pot, multi-enzyme system.

The present invention provides engineered ketoreductase ("KRED") enzymes that are capable of stereoselectively deracemizing a racemic alcohol substrate to an optically pure alcohol product in a one-pot, multi-enzyme system, and having an improved property when compared with the naturally-occurring, wild-type KRED enzyme obtained from *Candida parapsilosis* (SEQ ID NO:2), wild-type KRED enzyme obtained from *Sporidiobolus salmonicolor* (SEQ ID NO: 112), or when compared with other engineered ketoreductase enzymes. In addition, the present invention provides engineered phosphite dehydrogenase ("PDH") enzymes capable of preferentially recycling NADPH in the same one-pot, multi-enzyme system.

In some further embodiments, the engineered enzymes have one or more improved properties in addition to altered enzymatic activity. For example, in some embodiments, the engineered ketoreductase polypeptides have increased stereoselectivity, as compared to the wild-type ketoreductase enzyme for reducing the substrate to the product and/or preferentially oxidize the (S) enantiomer. Improvements in enzyme properties include, but are not limited to increases in thermostability, solvent stability, and/or reduced product inhibition.

The present invention provides engineered ketoreductase variants having at least 85%, 90%, 91%, 92%, 93%, 94%, 95%, 96%, 97%, 98%, 99% or more sequence identity to SEQ ID NO: 2, 112, 124, and/or 138.

The present invention also provides engineered ketoreductase variants have at least 85%, 90%, 91%, 92%, 93%, 94%, 95%, 96%, 97%, 98%, 99% or more sequence identity to SEQ ID NO:2, and at least one substitution or substitution set at one or more positions selected from positions 37, 37/211, 37/211/229, 37/229, 45, 52, 52/57/110/272/296, 52/57/272, 52/57/272/274/279/296, 52/57/272/279/296, 55/57/276, 56, 57, 57/104/114, 57/104/114/229, 57/286, 79/83/275/276, 83, 83/275/276, 83/276, 104, 110, 114, 138/146/258/289, 211, 211/229, 228, 229, 263, 268, 272, 274, 275/276, 276, 279, and 309, wherein the positions are numbered with reference to SEQ ID NO:2. In some additional embodiments, the engineered ketoreductase variants comprise at least one substitution or substitution set selected from 37R, 37R/21R, 37R/211R/229R, 37R/229R, 45R, 52D, 52D/57L/272H, 52S, 52S/57L/110T/272H/296F, 52S/57L/272H/279H/296F, 52S/57L/272H/274V/279H/296F, 55F/57A/276M, 56L, 57I, 57I/104G/114H, 57L, 57L/104G/114H/229R, 57X/286X, 79T/83S/275N/276M, 83I, 83S/275N/276M, 83S/276M, 104G, 110T, 114H/K/M, 138V/146S/258V/289S, 211R, 211R/229R, 228S, 229R, 263H/Y, 268M/W, 272H/I/L/P/Q/S/T/V/W, 274I/V, 275N/276M, 276/M, 279H/Q/R and 309F, wherein the positions are numbered with reference to SEQ ID NO:2. In some further embodiments, the engineered ketoreductase variants comprise at least one substitution or substitution set selected from K37R, K37R/K211R, K37R/K211R/G229R, K37R/G229R, H45R, Y52D, Y52D/C57L/G272H, Y52S, Y52S/C57L/K110T/G272H/L296F, Y52S/C57L/G272H/I279H/L296F, Y52S/C57L/G272H/L274V/I279H/L296F, L55F/C57A/L276M, D56L, C57I, C57I/A104G/G114H, C57L, C57L/A104G/G114H/G229R, C57X/W286X, I79T/V83S/A275N/L276M, V83I, V83S/A275N/L276M, V83S/L276M, A104G, K110T, G114H/K/M, S138V/A146S/M258V/T289S, K211R, K211R/G229R, P228S, G229R, G263H/Y, S268M/W, G272H/I/L/P/Q/S/T/V/W, L274I/V, A275N/L276M, L276F/M, I279H/Q/R, and R309F, wherein the positions are numbered with reference to SEQ ID NO:2.

The present invention also provides engineered ketoreductase variants having at least 85%, 90%, 91%, 92%, 93%, 94%, 95%, 96%, 97%, 98%, 99% or more sequence identity to SEQ ID NO:112, and at least one substitution or substitution set at one or more positions selected from positions 24/106/136/220/258/260/314/315, 24/106/214/250/258/260/314/315, 24/220/314/315, 122/159/316/318, 135, 139/207, 159/251/272/277/316/318/330, and 207, wherein the positions are numbered with reference to SEQ ID NO:112. In some embodiments, the engineered ketoreductase variants comprise at least one substitution or substitution set selected from 24I/106P/136A/220G/258V/260A/314R/315A, 24I/106P/214L/250V/258V/260A/314R/315A, 24I/220G/314R/315A, 122E/159V/316E/318L, 135F, 139V/207S, 159V/251Q/272F/277P/316E/318L/330L, and 207G, wherein the positions are numbered with reference to SEQ ID NO:112. In some additional embodiments, the engineered ketoreductase variants comprise at least one substitution or substitution set selected from V24I/T106P/S136A/S220G/L258V/C260A/P314R/S315A, V24I/T106P/F214L/A250V/L258V/C260A/P314R/S315A, V24I/S220G/P314R/S315A, T122E/I159V/L316E/I318L, V135F, I139V/N207S, I159V/V251Q/Y272F/T277P/L316E/I318L/I330L, and N207G, wherein the positions are numbered with reference to SEQ ID NO:112.

The present invention also provides engineered ketoreductase variants having at least 85%, 90%, 91%, 92%, 93%, 94%, 95%, 96%, 97%, 98%, 99% or more sequence identity to SEQ ID NO:124, and at least one substitution set selected from positions 2/101/179/182/228/238/282, 3/95, 3/95/228/314, 24/95/228, 95, 95/135/139/207, and 159/228/309/330, wherein the positions are numbered with reference to SEQ ID NO:124. In some embodiments, the engineered ketoreductase variants comprise at least one substitution or substitution set selected from 2T/101P/179L/182M/228R/238L/282E, 3Y/95T, 3Y/95T/228T/314R, 24I/95T/228T, 95T, 95T/135F/139V/207N, and 159V/228L/309Q/330L, wherein the positions are numbered with reference to SEQ ID NO:124. In some further embodiments, the engineered ketoreductase variants comprise at least one substitution or substitution set selected from A2T/Y101P/A179L/T182M/M228R/A238L/T282E, K3Y/V95T, K3Y/V95T/M228T/P314R, V24I/V95T/M228T, V95T, V95T/V135F/I139V/G207N, and I159V/M228L/K309Q/I330L, wherein the positions are numbered with reference to SEQ ID NO:124.

The present invention also provides engineered ketoreductase variants having at least 85%, 90%, 91%, 92%, 93%, 94%, 95%, 96%, 97%, 98%, 99% or more sequence identity to SEQ ID NO:138, and at least one substitution or substitution set at one or more positions selected from positions 19, 24/43/47/49/67/68/70/91/220, 24/68/91/218/220, 67, 72, 74/75/78/108, 75/78/99/108/215/224, 78/107, 95, 96, and 114, wherein the positions are numbered with reference to SEQ ID NO:138. In some embodiments, the engineered ketoreductase variants comprise at least one substitution or substitution set selected from 19S, 24I/43V/47E/49N/67V/68E/70P/91V/220G, 24I/68E/91V/218N/220G, 67W, 72Q, 74A/75E/78F/108V, 75E/78F/99P/108V/2155/224A, 78F/107G, 95C, 96G, and 114V, wherein the positions are numbered with reference to SEQ ID NO:138. In some further embodiments, the engineered ketoreductase variants comprise at least one substitution or substitution set selected from G19S, V24I/A43V/S47E/L49N/A67V/V68E/E70P/I91V/S220G, V24I/V68E/I91V/T218N/S220G, A67W, M72Q, K74A/Q75E/Y78F/A108V, Q75E/Y78F/N99P/A108V/D215S/S224A, Y78F/P107G, T95C, S96G, and N114V, wherein the positions are numbered with reference to SEQ ID NO:138.

The present invention also provides engineered ketoreductase variants comprising polypeptide sequences comprising sequences having at least 90% sequence identity to SEQ ID NO:2, 112, 124, and/or 138. In some embodiments, the engineered ketoreductase variants comprise polypeptide sequences comprising sequences having at least 95% sequence identity to SEQ ID NO:2, 112, 124, and/or 138. In some further embodiments, the engineered ketoreductase variants comprise polypeptide sequences set forth in SEQ ID NO:2, 112, 124, or 138. In some additional embodiments, the engineered ketoreductase variants comprise polypeptide sequences encoding variants provided in Table 5.1, 6.1, 7.1, and/or 8.1. In some further embodiments, the engineered ketoreductase variants comprise polypeptide sequences selected from the even-numbered sequences set forth in SEQ ID NOS: 4 to 170.

The present invention also provides engineered polynucleotide sequences encoding the engineered ketoreductase variants provided herein. In some embodiments, the engineered polynucleotide sequence comprises a polynucleotide sequence that is at least 85%, 90%, 91%, 92%, 93%, 94%, 95%, 96%, 97%, 98%, 99% or more identical to a sequence selected from the odd-numbered sequences set forth in SEQ ID NOS: 3 to 169. The present invention also provides vectors comprising the engineered polynucleotide sequences encoding the engineered ketoreductase variants provided herein. In some embodiments, the vectors further comprise at least one control sequence.

The present invention also provides host cells comprising the vectors comprising polynucleotides encoding the engineered ketoreductase variants provided herein.

The present invention also provides methods producing the engineered ketoreductase variants provided herein, comprising culturing the host cells provided herein under conditions that the engineered ketoreductase variant is produced by the host cell. In some embodiments, the methods further comprise the step of recovering the engineered ketoreductase variant produced by the host cell.

The present invention also provides immobilized engineered ketoreductase variants.

The present invention further provides compositions comprising at least one engineered ketoreductase variant provided herein. In some embodiments, the compositions comprise at least one immobilized engineered ketoreductase variant provided herein.

The present invention also provides engineered phosphite dehydrogenase variants having at least 85%, 90%, 91%, 92%, 93%, 94%, 95%, 96%, 97%, 98%, 99% or more sequence identity to SEQ ID NO: 172 and/or 208.

The present invention also provides engineered phosphite dehydrogenase variants having at least 85%, 90%, 91%, 92%, 93%, 94%, 95%, 96%, 97%, 98%, 99% or more sequence identity to SEQ ID NO:172, and at least one substitution or substitution set at one or more positions selected from positions 10/73/78/137/323/325, 10/73/78/233/323, 10/73/137, 13/41/63/132/193/195, 18/44/119/124/132/137/145/158/175/177/293/317/323, 18/44/119/124/132/137/145/158/177/293/323, 18/44/119/124/132/137/145/293/323/334/336, 32/44/132/137/145/186/233/293/323/336, 41/44/88/193/195, 44/69/120/132/137/145/175/195/293/323, 44/113/132/145, 44/119/132/137/145/158/175/177/293/317/323, 44/132/135/136/137/145/293, 44/132/136/137/145/293, 44/132/137/145/233/308/323, 44/132/137/145/293/323, 44/132/145, 44/132/145/195/293/323, 137/233/303/323, and 266, wherein the positions are numbered with reference to SEQ ID NO:172. In some embodiments, the engineered phosphite dehydrogenase variants comprise at least one substitution or substitution set selected from 10K/73A/78Y/137Q/323D/325A, 10K/73A/78Y/233I/323D, 10K/73A/137Q, 13D/41A/63A/132Q/193S/195E, 18M/44A/119F/124E/132Q/137I/145G/158K/175S/177T/293L/317R/323D, 18M/44A/119F/124E/132Q/137I/145G/158K/177T/293L/323D, 18M/44A/119F/124E/132Q/137I/145G/293L/323D/334K/336R, 32V/44A/132Q/137I/145G/186T/233I/293L/323D/336S, 41A/44A/88R/193S/195E, 44A/69K/120V/132Q/137I/145G/175T/195E/293L/323D, 44A/113S/132Q/145G, 44A/119F/132Q/137I/145G/158K/175S/177T/293L/317R/323D, 44A/132Q/135A/136D/137I/145G/293L, 44A/132Q/136D/137Q/145G/293L, 44A/132Q/137I/145G/233I/308V/323D, 44A/132Q/137I/145G/293L/323D, 44A/132Q/145G, 44A/132Q/145G/195E/293L/323D, 137Q/233I/303A/323D, and 266S/V/W, wherein the positions are numbered with reference to SEQ ID NO:172. In some further embodiments, the engineered phosphite dehydrogenase variants comprise at least one substitution or substitution set selected from R10K/C73A/F78Y/R137Q/N323D/V325A, R10K/C73A/F78Y/V233I/N323D, R10K/C73A/R137Q, E13D/R41A/Q63A/R132Q/A193S/S195E, L18M/R44A/L119F/A124E/R132Q/R137I/N145G/L158K/A175S/K177T/I293L/A317R/N323D, L18M/R44A/L119F/A124E/R132Q/R137I/N145G/L158K/K177T/I293L/N323D, L18M/R44A/L119F/A124E/R132Q/R137I/N145G/I293L/N323D/A334K/C336R, S32V/R44A/R132Q/R137I/N145G/R186T/V233I/I293L/N323D/C336S, R41A/R44A/A88R/A193S/S195E, R44A/R69K/R120V/R132Q/R137I/N145G/A175T/S195E/I293L/N323D, R44A/V113S/R132Q/N145G, R44A/L119F/R132Q/R137I/N145G/L158K/A175S/K177T/I293L/A317R/N323D, R44A/R132Q/Q135A/P136D/R137I/N145G/I293L, R44A/R132Q/P136D/R137Q/N145G/I293L, R44A/R132Q/R137I/N145G/V233I/A308V/N323D, R44A/R132Q/R137I/N145G/I293L/N323D, R44A/R132Q/N145G, R44A/R132Q/N145G/S195E/I293L/N323D, R137Q/V233I/E303A/N323D, and E266S/V/W, wherein the positions are numbered with reference to SEQ ID NO:172.

The present invention also provides engineered phosphite dehydrogenase variants having at least 85%, 90%, 91%, 92%, 93%, 94%, 95%, 96%, 97%, 98%, 99% or more sequence identity to SEQ ID NO:208, and at least one substitution or substitution set at one or more positions selected from positions 32/59/124/177/191/327, 78/150/198/327/328, 83/266, 95/211/213/322, 104, 178/194/211/213/322, 206, 211/213/322, 215, 262, 266, and 323, wherein the positions are numbered with reference to SEQ ID NO:208. In some embodiments, the engineered phosphite dehydrogenase variants comprise at least one substitution or substitution set selected from 32V/59M/124E/177S/191H/327D, 78Y/150I/198L/327S/328P, 83A/266A, 95I/211A/213Q/322M, 104F/L, 178P/194L/211A/213Q/322Q, 206N, 211A/213Q/322Q, 215P, 262D/P, 266S, and 323N, wherein the positions are numbered with reference to SEQ ID NO:208. In some further embodiments, the engineered phosphite dehydrogenase variants comprise at least one substitution or substitution set selected from S32V/A59M/A124E/T177S/Q191H/R327D, F78Y/F150I/F198L/R327S/L328P, V83A/E266A, F95I/N211A/D213Q/I322M, T104F/L, A178P/C194L/N211A/D213Q/I322Q, L206N, N211A/D213Q/I322Q, L215P, V262D/P, E266S, and D323N, wherein the positions are numbered with reference to SEQ ID NO:208.

The present invention also provides engineered phosphite dehydrogenase variants comprising a polypeptide sequence comprising a sequence having at least 90% sequence identity to SEQ ID NO:172 and/or 208. In some embodiments, the engineered phosphite dehydrogenase variants comprise polypeptide sequences comprising sequences having at least 95% sequence identity to SEQ ID NO:172 and/or 208. In some further embodiments, the engineered phosphite dehydrogenase variants comprise polypeptide sequences set forth in SEQ ID NO:172 or 208. In some additional embodiments, the engineered phosphite dehydrogenase variants comprise polypeptide sequences encoding variants provided in Table 9.1, 10.1, and/or 11.1. In yet some additional embodiments, the engineered phosphite dehydrogenase variants comprise polypeptide sequences selected from the even-numbered sequences set from in SEQ ID NOS: 174 to 260.

The present invention also provides immobilized engineered phosphite dehydrogenase variants. In some embodiments, the present invention provides a mixture of at least one immobilized engineered ketoreductase variant provided herein and at least one engineered phosphite dehydrogenase variant provided herein.

The present invention also provides compositions comprising at least one phosphite dehydrogenase variant provided herein. In some embodiments, the present invention further provides compositions comprising mixtures of at least one engineered ketoreductase variant provided herein and at least one engineered phosphite dehydrogenase provided herein.

The present invention also provides engineered polynucleotide sequences encoding the engineered phosphite dehydrogenase variants provided herein. In some embodiments, the engineered polynucleotide sequences comprise polynucleotide sequences that are at least 85%, 90%, 91%, 92%, 93%, 94%, 95%, 96%, 97%, 98%, 99% or more identical to a sequence selected from the odd-numbered sequences set forth in SEQ ID NOS: 3 to 169.

The present invention also provides vectors comprising the engineered polynucleotide sequence encoding the engineered phosphite dehydrogenase variants provided herein. In some embodiments, the vectors further comprise at least one control sequence. In yet some further embodiments, the vectors comprise at least one engineered polynucleotide sequence encoding an engineered phosphite dehydrogenase variant provided herein and at least one engineered polynucleotide sequence encoding an engineered ketoreductase variant provided herein. The present invention also provides host cells comprising the vectors provided herein.

The present invention also provides methods for producing the engineered phosphite dehydrogenase variants provided herein, comprising culturing the host cell comprising a vector comprising at least one engineered polynucleotide sequence encoding at least one engineered phosphite dehydrogenase of the present invention, under conditions that the engineered phosphite dehydrogenase variant is produced by the host cell. In some embodiments, the host cells comprise vectors comprising polynucleotide sequences comprising at least one engineered ketoreductase and at least one engineered phosphite dehydrogenase provided herein. In some additional embodiments, the host cells comprise at least one ketoreductase not provided herein, but comprise at least one engineered phosphite dehydrogenase variant provided herein. In some further embodiments, the host cells comprise at least on phosphite dehydrogenase not provided herein, but comprise at least one engineered ketoreductase variant provided herein. In some embodiments, the methods further comprise the step of recovering the engineered phosphite dehydrogenase variant produced by the host cell. In embodiments with host cells that produce at least one ketoreductase and at least one phosphite dehydrogenase, some methods further comprise the step of recovering the ketoreductase and/or phosphite dehydrogenase produced by the host cells.

The present invention also provides methods deracemizing chiral alcohols comprising providing at least one engineered ketoreductase variant provided herein, providing at least one engineered phosphite dehydrogenase variant provided herein, at least one chiral alcohol, and at least one co-factor, under conditions such that the chiral alcohol is deracemized. In some embodiments, the methods are conducted in a one pot reaction, while in some alternative embodiments, multiple reaction vessels are used.

DESCRIPTION OF THE INVENTION

Figure 1:
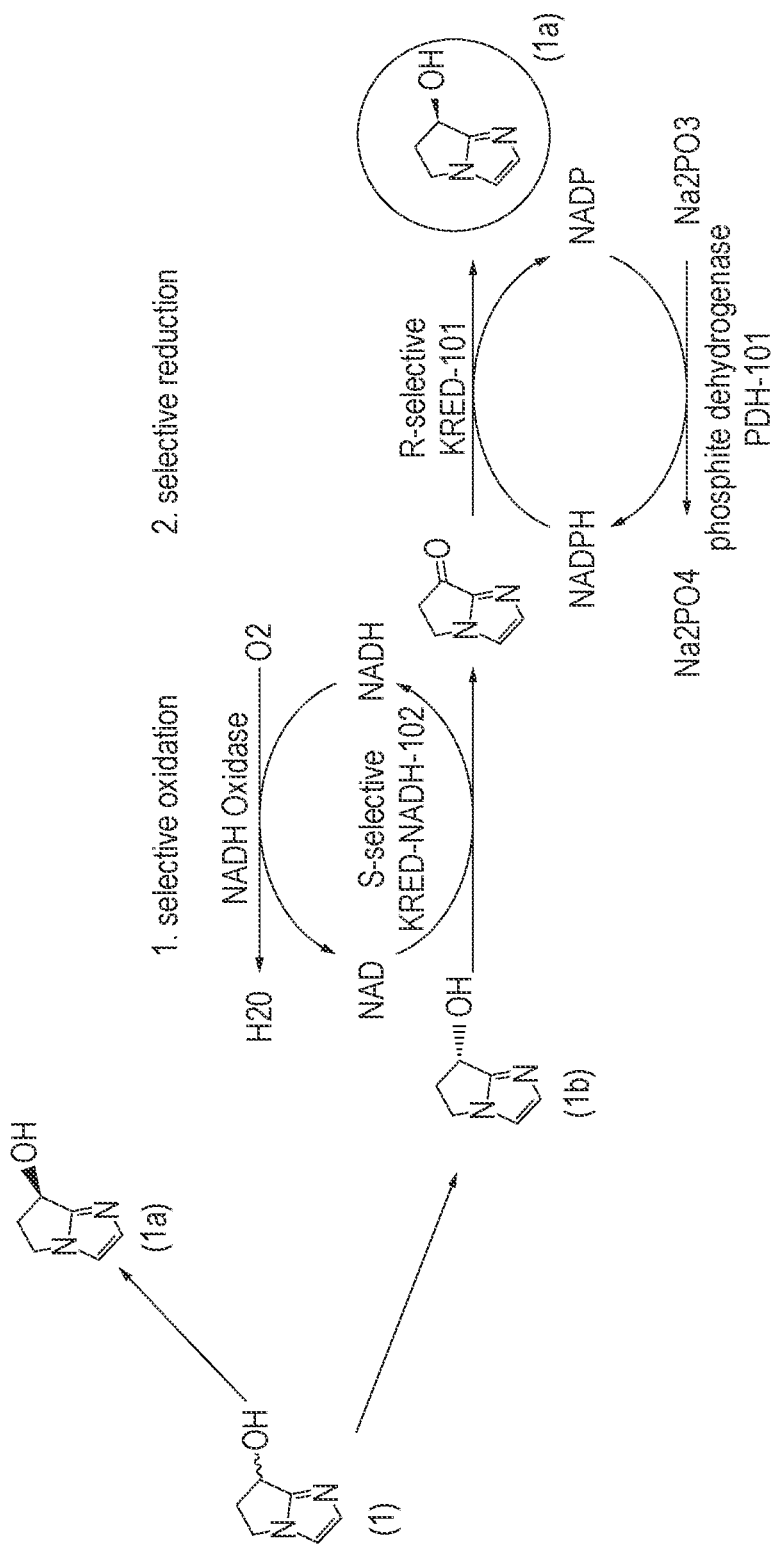
FIG. 1 provides the reaction scheme addressed by the present invention.

The present invention provides engineered ketoreductase enzymes and engineered phosphite dehydrogenase enzymes having improved properties as compared to a naturally occurring wild-type ketoreductase and phosphite dehydrogenase enzyme, as well as polynucleotides encoding the engineered ketoreductase and engineered phosphite dehydrogenase enzymes, host cells capable of expressing the engineered ketoreductase and engineered phosphite dehydrogenase enzymes, and methods of using the engineered ketoreductase and engineered phosphite dehydrogenase enzymes to deracemize a racemic alcohol in a one-pot, multi-enzyme system.

Definitions

In reference to the present invention, the technical and scientific terms used in the descriptions herein will have the meanings commonly understood by one of ordinary skill in the art, unless specifically defined otherwise. Accordingly, the following terms are intended to have the following meanings. All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation and amino acid sequences are written left to right in amino to carboxy orientation, respectively.

The headings provided herein are not limitations of the various aspects or embodiments of the invention that can be had by reference to the specification as a whole. Accordingly, the terms defined below are more fully defined by reference to the specification as a whole.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively deracemizing an alcohol of formula (I) to the corresponding product of formula (II) in an one-pot, multi-enzyme system, as shown in Scheme 1 (See, FIG. 1).

Phosphite dehydrogenase and "PDH" are used interchangeably herein to refer to a polypeptide having an enzymatic capability of regenerating NADPH co-factor.

As used herein, the term "one-pot reaction" refers to the production of a product from a starting material using multiple enzymes (i.e., KREDs and PDHs) in one reaction vessel.

As used herein, the terms "protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

As used herein, "polynucleotide" and "nucleic acid" refer to two or more nucleosides that are covalently linked together. The polynucleotide may be wholly comprised of ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more nonstandard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases (e.g., inosine, xanthine, hypoxanthine, etc.). Preferably, such modified or synthetic nucleobases will be encoding nucleobases.

As used herein, "coding sequence" refers to that portion of a nucleic acid (e.g., a gene) that encodes an amino acid sequence of a protein.

As used herein, "naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

As used herein, "non-naturally occurring" or "engineered" or "recombinant" when used in the present invention with reference to (e.g., a cell, nucleic acid, or polypeptide), refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

As used herein, "percentage of sequence identity," "percent identity," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (See e.g., Altschul et al., J. Mol. Biol. 215: 403-410 [1990]; and Altschul et al., Nucleic Acids Res. 3389-3402 [1977]). Software for performing BLAST analyses is publicly available through the National Center for Biotechnology Information website.

Briefly, the BLAST analyses involve first identifying high scoring sequence pairs (HSPs) by identifying short words of length Win the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc Natl Acad Sci USA 89:10915 [1989]).

Numerous other algorithms are available and known in the art that function similarly to BLAST in providing percent identity for two sequences. Optimal alignment of sequences for comparison can be conducted using any suitable method known in the art (e.g., by the local homology algorithm of Smith and Waterman, Adv. Appl. Math. 2:482 [1981]; by the homology alignment algorithm of Needleman and Wunsch, J. Mol. Biol. 48:443 [1970]; by the search for similarity method of Pearson and Lipman, Proc. Natl. Acad. Sci. USA 85:2444 [1988]; and/or by computerized implementations of these algorithms [GAP, BESTFIT, FASTA, and TFASTA in the GCG Wisconsin Software Package]), or by visual inspection, using methods commonly known in the art. Additionally, determination of sequence alignment and percent sequence identity can employ the BESTFIT or GAP programs in the GCG Wisconsin Software package (Accelrys, Madison Wis.), using the default parameters provided.

As used herein, "reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

As used herein, "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. As used herein, a reference to a residue position, such as "Xn" as further described below, is to be construed as referring to "a residue corresponding to", unless specifically denoted otherwise. Thus, for example, "X94" refers to any amino acid at position 94 in a polypeptide sequence.

As used herein, "stereoselectivity" refers to the preferential formation in a chemical or enzymatic reaction of one stereoisomer over another stereoisomer or another set of stereoisomers. Stereoselectivity can be partial, where the formation of a stereoisomer is favored over another, or it may be complete where only one stereoisomer is formed. When the stereoisomers are enantiomers, the stereoselectivity is referred to as enantioselectivity, the fraction (typically reported as a percentage) of one enantiomer in the sum of both enantiomers. It is commonly alternatively reported in the art (typically as a percentage) as the enantiomeric excess (e.e.) calculated therefrom according to the formula [major enantiomer—minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess. It is also to be understood that stereoselectivity is not limited to single stereoisomers and can be described for sets of stereoisomers.

As used herein, "highly stereoselective" refers to a chemical or enzymatic reaction that is capable of converting a substrate to its corresponding chiral alcohol product, with at least about 75% stereomeric excess.

As used herein, "increased enzymatic activity" and "increased activity" refer to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of ketoreductase) as compared to a reference enzyme. Exemplary methods to determine enzyme activity are provided in the Examples. Any property relating to enzyme activity may be affected, including the classical enzyme properties of Km, Vmax or kcat, changes of which can lead to increased enzymatic activity. The ketoreductase activity can be measured by any one of standard assays used for measuring ketoreductases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

As used herein, "conversion" refers to the enzymatic transformation of a substrate to the corresponding product.

As used herein "percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

As used herein, "thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

As used herein, "solvent stable" refers to the ability of a polypeptide to maintain similar activity (e.g., more than e.g., 60% to 80%) after exposure to varying concentrations (e.g., 5-99%) of solvent compared to the untreated enzyme.

As used herein, "amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X40 as compared to SEQ ID NO:2" refers to a difference of the amino acid residue at the polypeptide position corresponding to position 40 of SEQ ID NO:2. Thus, if the reference polypeptide of SEQ ID NO:2 has a histidine at position 40, then a "residue difference at position X40 as compared to SEQ ID NO:2" refers to an amino acid substitution of any residue other than histidine at the position of the polypeptide corresponding to position 40 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances, the present invention also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present invention can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X192A/G). The present invention includes engineered polypeptide sequences comprising one or more amino acid differences that include either/or both conservative and non-conservative amino acid substitutions. The amino acid sequences of the specific recombinant carbonic anhydrase polypeptides included in the Sequence Listing of the present invention include an initiating methionine (M) residue (i.e., M represents residue position 1). The skilled artisan, however, understands that this initiating methionine residue can be removed by biological processing machinery, such as in a host cell or in vitro translation system, to generate a mature protein lacking the initiating methionine residue, but otherwise retaining the enzyme's properties. Consequently, the term "amino acid residue difference relative to SEQ ID NO:2 at position Xn" as used herein may refer to position "Xn" or to the corresponding position (e.g., position (X−1)n) in a reference sequence that has been processed so as to lack the starting methionine.

As used herein, the phrase "conservative amino acid substitutions" refers to the interchangeability of residues having similar side chains, and thus typically involves substitution of the amino acid in the polypeptide with amino acids within the same or similar defined class of amino acids. By way of example and not limitation, in some embodiments, an amino acid with an aliphatic side chain is substituted with another aliphatic amino acid (e.g., alanine, valine, leucine, and isoleucine); an amino acid with a hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively. Exemplary conservative substitutions are provided in Table 1.

TABLE 1

Exemplary Conservative Amino Acid Substitutions

| Residue | Possible Conservative Substitutions |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | Non-polar |

As used herein, the phrase "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

As used herein, "insertion" refers to modification of the polypeptide by addition of one or more amino acids to the reference polypeptide. In some embodiments, the improved engineered ketoreductase enzymes comprise insertions of one or more amino acids to the naturally occurring ketoreductase polypeptide as well as insertions of one or more amino acids to engineered ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant KREDs listed in the Tables provided in the Examples.

As used herein, "fragment" refers to a polypeptide that has an amino-terminal and/or carboxy-terminal deletion, but where the remaining amino acid sequence is identical to the corresponding positions in the sequence. Fragments can typically have about 80%, about 90%, about 95%, about 98%, or about 99% of the full-length ketoreductase polypeptide, for example the polypeptide of SEQ ID NO:4. In some embodiments, the fragment is "biologically active" (i.e., it exhibits the same enzymatic activity as the full-length sequence).

As used herein, "isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the engineered ketoreductase polypeptides of the present invention can be an isolated polypeptide.

As used herein, "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered ketoreductase polypeptide composition will comprise about 60% or more, about 70% or more, about 80% or more, about 90% or more, about 91% or more, about 92% or more, about 93% or more, about 94% or more, about 95% or more, about 96% or more, about 97% or more, about 98% or more, or about 99% of all macromolecular species by mole or % weight present in the composition. Solvent species, small molecules (<500 Daltons), and elemental ion species are not considered macromolecular species. In some embodiments, the isolated improved ketoreductase polypeptide is a substantially pure polypeptide composition.

As used herein, when used with reference to a nucleic acid or polypeptide, the term "heterologous" refers to a sequence that is not normally expressed and secreted by an organism (e.g., a wild-type organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector). In some embodiments, "heterologous polynucleotide" refers to any polynucleotide that is introduced into a host cell by laboratory techniques, and includes polynucleotides that are removed from a host cell, subjected to laboratory manipulation, and then reintroduced into a host cell.

As used herein, "codon optimized" refers to changes in the codons of the polynucleotide encoding a protein to those preferentially used in a particular organism such that the encoded protein is efficiently expressed in the organism of interest. In some embodiments, the polynucleotides encoding the ketoreductase enzymes may be codon optimized for optimal production from the host organism selected for expression.

As used herein, "control sequence" is defined herein to include all components, which are necessary or advantageous for the expression of a polynucleotide and/or polypeptide of the present invention. Each control sequence may be native or foreign to the polynucleotide of interest. Such control sequences include, but are not limited to, a leader, polyadenylation sequence, propeptide sequence, promoter, signal peptide sequence, and transcription terminator.

As used herein, "operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

As used herein, the phrases "cofactor regeneration system" and "cofactor recycling system" refer to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

As used herein, "suitable reaction conditions" refer to those conditions in the biocatalytic reaction solution (e.g., ranges of enzyme loading, substrate loading, cofactor loading, temperature, pH, buffers, co-solvents, etc.) under which ketoreductase polypeptides of the present invention are capable of stereoselectively deracemizing a substrate compound to a product compound. Exemplary "suitable reaction conditions" are provided in the present invention and illustrated by the Examples.

As used herein, "loading," such as in "compound loading," "enzyme loading," or "cofactor loading" refers to the concentration or amount of a component in a reaction mixture at the start of the reaction.

As used herein, "substrate" in the context of a biocatalyst mediated process refers to the compound or molecule acted on by the biocatalyst. For example, an exemplary substrate for the ketoreductase biocatalyst in the process disclosed herein is compound (1).

As used herein "product" in the context of a biocatalyst mediated process refers to the compound or molecule resulting from the action of the biocatalyst.

As used herein, "equilibration" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

As used herein, "oxo" refers to =O.

As used herein, "oxy" refers to a divalent group —O—, which may have various substituents to form different oxy groups, including ethers and esters.

As used herein, "carboxy" refers to —COOH.

As used herein, "carbonyl" refers to —C(O)—, which may have a variety of substituents to form different carbonyl groups including acids, acid halides, aldehydes, amides, esters, and ketones.

As used herein, "hydroxy" refers to —OH.

As used herein, "optional" and "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included.

As used herein, "optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

Engineered Enzyme Polypeptides

Ketoreductase (KRED) or carbonyl reductase biocatalysts (EC 1.1.1.184) are useful for the synthesis of alcohols from aldehydes and ketones, and optically active secondary alcohols from the corresponding prostereoisomeric ketone substrates. KREDs may also catalyze the reverse reaction, (i.e., oxidation of an alcohol substrate to the corresponding aldehydes/ketone product). The reduction of aldehydes and ketones and the oxidation of alcohols by KREDs uses a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD+ and NADP+ serve as electron acceptors.

KREDs can be found in a wide range of bacteria and yeasts, as known in the art (See e.g., Hummel and Kula Eur. J. Biochem., 184:1-13 [1989]). Numerous KRED genes and enzyme sequences have been reported, including those of *Candida magnoliae* (Genbank Acc. No. JC7338; GI:11360538); *Candida parapsilosis* (Genbank Acc. No. BAA24528.1; G:2815409), *Sporobolomyces salmonicolor* (Genbank Acc. No. AF160799; G:6539734), *Lactobacillus kefir* (Genbank Acc. No. AAP94029.1; GI: 33112056), *Lactobacillus brevis* (Genbank Acc. No. 1NXQ_A; GI: 30749782), and *Thermoanaerobium brockii* (Genbank Acc. No. P14941; GI: 1771790).

The stereoselectivity of ketoreductases have been applied to the preparation of important pharmaceutical building blocks (See e.g., Broussy et al., Org. Lett., 11:305-308 [2009]). Specific applications of naturally occurring or engineered KREDs in biocatalytic processes to generate useful chemical compounds have been demonstrated for reduction of 4-chloroacetoacetate esters (See e.g., Zhou, J. Am. Chem. Soc., 105:5925-5926 [1983]; Santaniello, J. Chem. Res., (S)132-133 [1984]; U.S. Pat. Nos. 5,559,030; 5,700,670; and 5,891,685), reduction of dioxocarboxylic acids (See e.g., U.S. Pat. No. 6,399,339), reduction of tert-butyl (S)-chloro-5-hydroxy-3-oxohexanoate (See e.g., U.S. Pat. No. 6,645,746; and WO 01/40450), reduction pyrrolotriazine-based compounds (See e.g., U.S. Appln. Publ. No. 2006/0286646); reduction of substituted acetophenones (See e.g., U.S. Pat. Nos. 6,800,477 and 8,748,143); and reduction of ketothiolanes (WO 2005/054491).

The present invention provides engineered ketoreductases capable of deracemizing the substrate compound (1), (6,7-dihydro-5H-pyrrolo[1,2-a]imidazol-7-ol), in one-pot, multi-enzyme system as shown in the following reaction and FIG. 1.

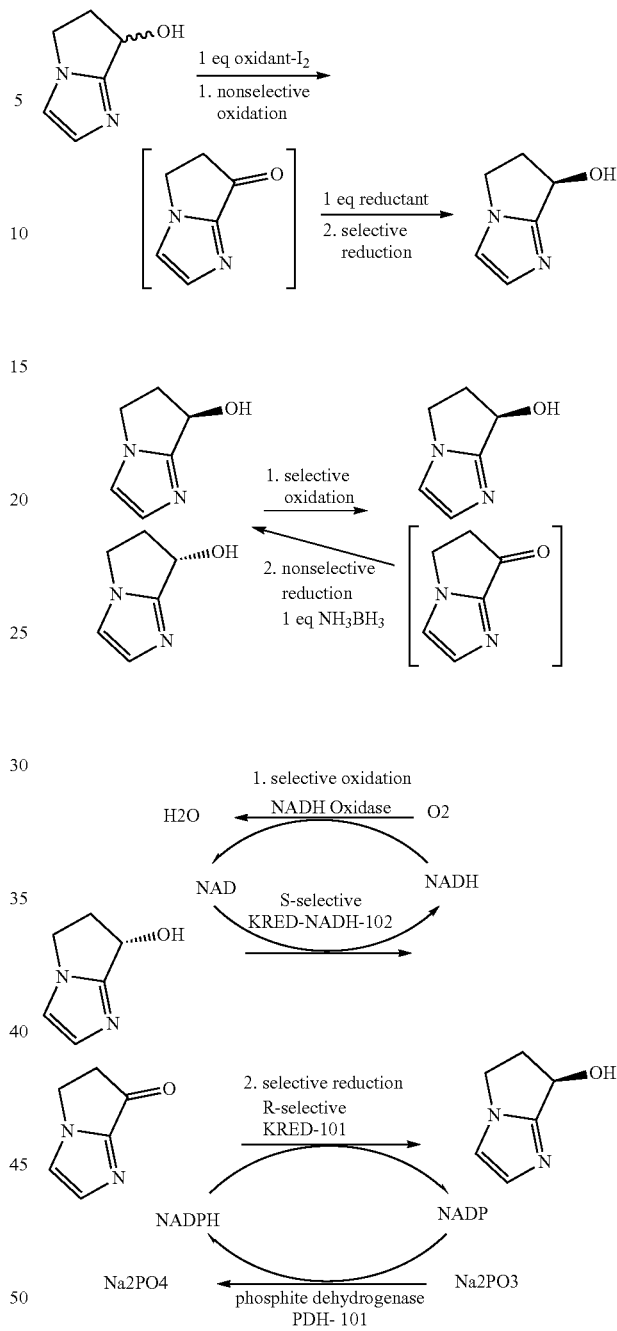

The present invention further provides improved ketoreductase enzymes and improved phosphite dehydrogenase enzymes, and methods for using the engineered ketoreductase and phosphite dehydrogenase enzymes to deracemize chiral compounds in one-pot, multi-enzyme system.

It is important to note that the desired product can be obtained in a one-pot, one-step, multi-enzyme system only if the oxidation and reduction reactions are orthogonal, compatible and non-interacting. These conditions are only satisfied if the oxidative ketoreductase and its corresponding recycling enzyme use one co-factor exclusively (e.g., NAD+), and reductive ketoreductase and its corresponding recycling enzyme use the opposite co-factor exclusively (i.e., NADPH).

Figure 2:
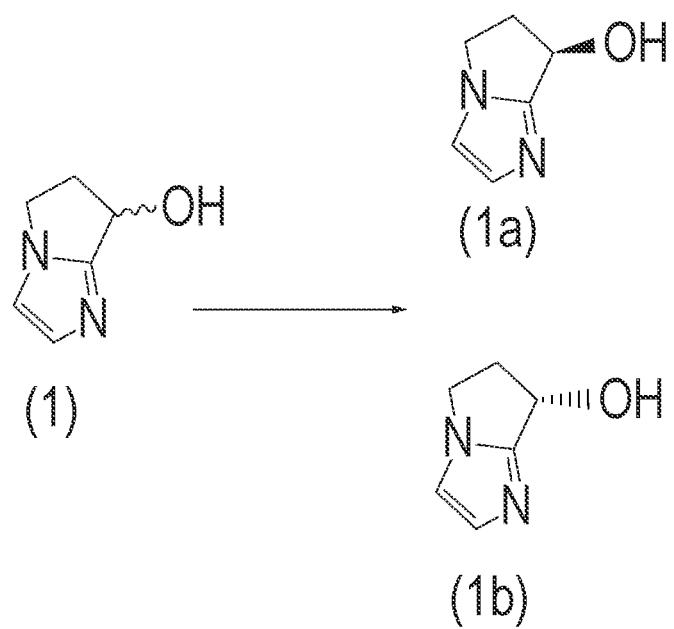
FIG. 2 provides the structures of substrate and product isomers.

Compound (1) has one chiral center and can exist in two different diastereomeric forms (1a and 1b). The deracemization reaction by a tandem of ketoreductases can result in two different enantiomeric products (1a-1b), as shown in FIG. 2 and below.

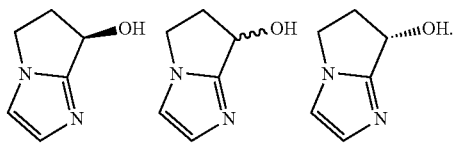

However, (1a) is the only desired product. The evolution program used in the development of the present invention was designed to improve activity of an S-selective ketoreductase that would oxidize the S-alcohol in the racemic mixture, generating a ketone substrate for an R-selective ketoreductase. Further, evolution program was designed to improve the selectivity, activity and cofactor preference of the R-selective ketoreductase. Evolution was also designed to improve activity, stability and cofactor preference of a phosphite dehydrogenase to enable deracemization of substrate (1) to product (1a) with minimal amount of ketone and (1b) in a one-pot, one-step, multi-enzyme process.

The ketoreductase polypeptide of SEQ ID NO:2 was selected as the initial backbone for development of the improved S-selective enzymes provided by the present invention. This enzyme was chosen as the starting backbone as ketone (2) was produced via oxidation of only (1b), leaving (1a). The ketoreductase polypeptide of SEQ ID NO:2 uses NAD$^+$ as a co-factor with an efficiency greater than 200:1 over NADP+ and can be coupled with a commercially available NADH oxidase to recycle the co-factor.

The ketoreductase polypeptide of SEQ ID NO:2 was selected as the initial backbone for development of R-selective enzymes to reduce a ketone to product (1a) with initial selectivity of 92.7% e.e. Enantioselectivity values are calculated herein according to equation (1) provided below.

$$\{[(1a \text{ amount})-(1b \text{ amount})]/[(1a \text{ amount})+(1b \text{ amount})]\} \times 100 \qquad (1)$$

Indeed, the non-naturally occurring ketoreductase polypeptides of the present invention are ketoreductases engineered to have improved properties as compared to the naturally occurring ketoreductase of SEQ ID NO:2.

A phosphite dehydrogenase polypeptide was selected as the initial backbone for development of the improved PDH enzymes. This enzyme is equally efficient recycling both NADH and NADPH.

In some embodiments, the engineered ketoreductase polypeptides are capable of converting the substrate compound to product with an activity that is increased at least about 1.2 fold, 1.5 fold, 2 fold, 3 fold, 4 fold, 5 fold, 10 fold, 20 fold, 30 fold, 40 fold, 50 fold, or 100 fold relative to the activity of the reference polypeptide of SEQ ID NO:2 under suitable reaction conditions. In some embodiments, the engineered ketoreductase polypeptides are capable of converting the substrate compound to product with a percent conversion of at least about 40%, at least about 50%, at least about 60%, at least about 70%, at least about 80%, or at least about 90%, at least about 95%, at least about 98%, at least about 99%, in a reaction time of about 48 h, about 36 h, about 24 h, or even shorter length of time, under suitable reaction conditions.

In some embodiments, the engineered ketoreductases and phosphite dehydrogenases are capable of converting substrate compound (1) to product compound (1a) in enantiomeric excess over compound (1b) in a one-pot, one-step, multi-enzyme system. In some embodiments, the engineered ketoreductases and phosphite dehydrogenases are capable of converting compound (1) to compound (1a) in diastereomeric excess over compound (b) under suitable reaction conditions.

As will be appreciated by those of skill in the art, some of the above-defined categories, unless otherwise specified, are not mutually exclusive. Thus, amino acids having side chains exhibiting two or more physico-chemical properties can be included in multiple categories. The appropriate classification of any amino acid or residue will be apparent to those of skill in the art, especially in light of the detailed invention provided herein.

In some embodiments, the improved engineered ketoreductase enzymes and engineered phosphite dehydrogenase enzymes comprise amino acid residue deletions in the naturally occurring ketoreductase or phosphite dehydrogenase polypeptides or deletions of amino acid residues in other engineered ketoreductase or phosphite dehydrogenase polypeptides. Thus, in some embodiments of the invention, the deletions comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase or phosphite dehydrogenase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As described herein, the ketoreductase or phosphite dehydrogenase polypeptides of the invention can be in the form of fusion polypeptides in which the ketoreductases or phosphite dehydrogenase polypeptides are fused to other polypeptides, such as antibody tags (e.g., myc epitope) or purifications sequences (e.g., His tags). Thus, in some embodiments, the ketoreductase and/or phosphite dehydrogenase polypeptides find use with or without fusions to other polypeptides.

In some embodiments, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); 8-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised are apparent to those of skill in the art. These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(8-benzylester), Gln(xanthyl), Asn(N-8-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzymes and engineered phosphite dehydrogenase enzymes can be targeted to a specific property of the enzyme.

Polynucleotides Encoding Engineered Enzymes

In another aspect, the present invention provides polynucleotides encoding the engineered ketoreductase enzymes and engineered phosphite dehydrogenase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase and/or engineered phosphite dehydrogenase can be introduced into appropriate host cells to express the corresponding ketoreductase or phosphite dehydrogenase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes and/or improved phosphite dehydrogenase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made by selecting combinations based on the possible codon choices, and all such variations are to be considered specifically disclosed for any polypeptide disclosed herein, including the amino acid sequences presented in the Tables in the Examples. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

In some embodiments, the engineered ketoreductase or phosphite dehdyrogease sequences comprise sequences that comprise positions identified to be beneficial, as described in the Examples.

In some embodiments, isolated polynucleotides encoding an improved ketoreductase or phosphite dehydrogenase polypeptides are manipulated in a variety of ways to provide for improved expression and/or production of the polypeptides. Manipulation of the isolated polynucleotide prior to its insertion into a vector may be desirable or necessary, depending on the expression vector used. The techniques for modifying polynucleotides and nucleic acid sequences utilizing recombinant DNA methods are well known in the art.

For bacterial host cells, suitable promoters for directing transcription of the nucleic acid constructs of the present invention, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl. Acad. Sci. USA 75: 3727-3731 [1978]), as well as the tac promoter (See e.g., DeBoer et al., Proc. Natl Acad. Sci. USA 80: 21-25 [1983]). Additional suitable promoters are known to those in the art.

For filamentous fungal host cells, suitable promoters for directing the transcription of the nucleic acid constructs of the present invention include promoters obtained from the genes for *Aspergillus oryzae* TAKA amylase, *Rhizomucor* miehei aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters include, but are not limited to those from the genes for *Saccharomyces cerevisiae* enolase (ENO-1), *Saccharomyces cerevisiae* galactokinase (GAL), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, as well as other useful promoters for yeast host cells (See e.g., Romanos et al., Yeast 8:423-488 [1992]).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase, as well as other useful terminators for yeast host cells known in the art (See e.g., Romanos et al., supra).

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase, as well as additional useful polyadenylation sequences for yeast host cells known in the art (See e.g., Guo et al., Mol. Cell. Biol., 15:5983-5990 [1995]).

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA, as well as additional signal peptides known in the art (See e.g., Simonen et al., Microbiol. Rev., 57: 109-137 [1993]).

Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase, as well as additional useful signal peptide coding regions (See e.g., Romanos et al., 1992, supra).

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention or the PDH polypeptide of the present invention would be operably linked with the regulatory sequence.

Thus, in some embodiments, the present invention is also directed to a recombinant expression vector comprising a polynucleotide encoding an engineered ketoreductase polypeptide or a variant thereof, or an engineered phosphite dehydrogenase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector (i.e., a vector that exists as an extrachromosomal entity), the replication of which is independent of chromosomal replication, (e.g., a plasmid, an extrachromosomal element, a minichromosome, or an artificial chromosome). The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker can be a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A on or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (See e.g., Ehrlich, Proc.

Natl. Acad. Sci. USA 75:1433 [1978]).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include, but are not limited to p3×FLAG™™ expression vectors (Sigma-Aldrich), which include a CMV promoter and hGH polyadenylation site for expression in mammalian host cells and a pBR322 origin of replication and ampicillin resistance markers for amplification in *E. coli*. Other commercially available suitable expression vectors include but are not limited to the pBluescriptII SK(−) and pBK-CMV vectors (Stratagene), and plasmids derived from pBR322 (Gibco BRL), pUC (Gibco BRL), pREP4, pCEP4 (Invitrogen) or pPoly (See, Lathe et al., Gene 57:193-201 [1987]).

Host Cells for Expression of Engineered Polypeptides

The present invention also provides a host cell comprising a polynucleotide encoding an improved ketoreductase polypeptide or an improved phosphite dehydrogenase polypeptide of the present invention, the polynucleotide being operatively linked to one or more control sequences for expression of the ketoreductase enzyme or the phosphite dehydrogenase enzyme in the host cell. Host cells for use in expressing the KRED polypeptides encoded by the expression vectors of the present invention or the PDH polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture media and growth conditions for the above-described host cells are well known in the art.

Polynucleotides for expression of the ketoreductase or the phosphite dehydrogenase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

*Escherichia coli* W3110 is a host strain that finds use in the present invention, although it is not intended that the present invention be limited to this specific host strain. The expression vector was created by operatively linking a polynucleotide encoding an improved enzyme into the plasmid pCK110900 operatively linked to the lac promoter under control of the lacI repressor. The expression vector also contained the P15a origin of replication and the chloramphenicol resistance gene. Cells containing the subject polynucleotide in *Escherichia coli* W3110 can be isolated by subjecting the cells to chloramphenicol selection.

Methods of Generating Engineered Ketoreductase Polypeptides and Engineered Phosphite Dehydrogenase Polypeptides.

In some embodiments, to make the improved KRED polynucleotides and polypeptides of the present invention, the naturally-occurring ketoreductase enzyme that catalyzes the reduction reaction is obtained (or derived) from *Candida parasilosis* or *Sporodiobolus salmonicolor*. In some embodiments, the parent polynucleotide sequence is codon optimized to enhance expression of the ketoreductase in a specified host cell. As an illustration, the parental polynucleotide sequence encoding the wild-type KRED polypeptide of *Sporodiobolus salmonicolor* was constructed from oligonucleotides prepared based upon the known polypeptide sequence of *Sporodiobolus salmonicolor* KRED sequence available from the Genbank database. The parental polynucleotide sequence was codon optimized for expression in *E. coli* and the codon-optimized polynucleotide cloned into an expression vector, placing the expression of the ketoreductase gene under the control of the lac promoter and lacI repressor gene. Clones expressing the active ketoreductase in *E. coli* were identified and the genes sequenced to confirm their identity.

In some embodiments, the engineered ketoreductases are obtained by subjecting the polynucleotide encoding the naturally occurring ketoreductase to mutagenesis and/or directed evolution methods, as discussed above. Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). The stereochemistry of the products can be ascertained by various known techniques, and as provided in the Examples. Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides of the invention can be prepared by chemical synthesis (e.g., using the classical phosphoramidite method described by Beaucage et al., Tet. Lett., 22:1859-69 [1981], or the method described by Matthes et al., EMBO J., 3:801-05 [1984], as it is typically practiced in automated synthetic methods). According to the phosphoramidite method, oligonucleotides are synthesized (e.g., in an automatic DNA synthesizer), purified, annealed, ligated and cloned in appropriate vectors. In addition, essentially any nucleic acid can be obtained from any of a variety of commercial sources (e.g., The Midland Certified Reagent Company, Midland, Tex., The Great American Gene Company, Ramona, Calif., ExpressGen Inc. Chicago, Ill., Operon Technologies Inc., Alameda, Calif., and many others).

Engineered ketoreductase enzymes and engineered phosphite dehydrogenase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name Cel-Lytic B™ (Sigma-Aldrich).

Chromatographic techniques for isolation of the ketoreductase and/or phosphite dehydrogenase polypeptides include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques are used to isolate the improved ketoreductase enzymes and/or improved phosphite dehydrogenase enzymes. For affinity chromatography purification, any antibody which specifically binds the ketoreductase polypeptide or the phosphite dehydrogenase polypeptide may be used. For the production of antibodies, various host animals, including but not limited to rabbits, mice, rats, etc., may be immunized by injection with the ketoreductase or the phosphite dehydrogenase. The ketoreductase polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*Bacillus* Calmette Guerin) and *Corynebacterium parvum*.

The ketoreductases and/or the phosphite dehydrogenases may be prepared and used in the form of cells expressing the enzymes, as crude extracts, or as isolated or purified preparations. The ketoreductases and/or the phosphite dehydrogenases may be prepared as lyophilizates, in powder form (e.g., acetone powders), or prepared as enzyme solutions. In some embodiments, the ketoreductases or the phosphite dehydrogenases can be in the form of substantially pure preparations.

In some embodiments, the ketoreductase polypeptides and/or the phosphite dehydrogenase polypeptides can be attached to a solid substrate. The substrate can be a solid phase, surface, and/or membrane. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture. The reduced NAD(P)H form can be optionally regenerated from the oxidized $NAD(P)^+$ form using a cofactor regeneration system. The term "cofactor regeneration system" refers to a set of reactants that participate in a reaction that reduces the oxidized form of the cofactor (e.g., $NADP^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD+ or NADP+, respectively, are known in the art and may be used in the methods described herein.

EXPERIMENTAL

Various features and embodiments of the invention are illustrated in the following representative examples, which are intended to be illustrative, and not limiting.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and pg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); RT (room temperature); CDS (coding sequence); DNA (deoxyribonucleic acid); RNA (ribonucleic acid); HPLC (high performance liquid chromatography); FIOPC (fold improvement over positive control); HTP (high throughput); LB (Luria broth); Sigma-Aldrich (Sigma-Aldrich, St. Louis, Mo.); Millipore (Millipore, Corp., Billerica Mass.); Difco (Difco Laboratories, BD Diagnostic Systems, Detroit, Mich.); Daicel (Daicel, West Chester, Pa.); Genetix (Genetix USA, Inc., Beaverton, Oreg.); Molecular Devices (Molecular Devices, LLC, Sunnyvale, Calif.); Applied Biosystems (Applied Biosystems, part of Life Technologies, Corp., Grand Island, N.Y.), Agilent (Agilent Technologies, Inc., Santa Clara, Calif.); Thermo Scientific (part of Thermo Fisher Scientific, Waltham, Mass.); Corning (Corning, Inc., Palo Alto, Calif.); and Bio-Rad (Bio-Rad Laboratories, Hercules, Calif.).

Example 1

Figure 3:
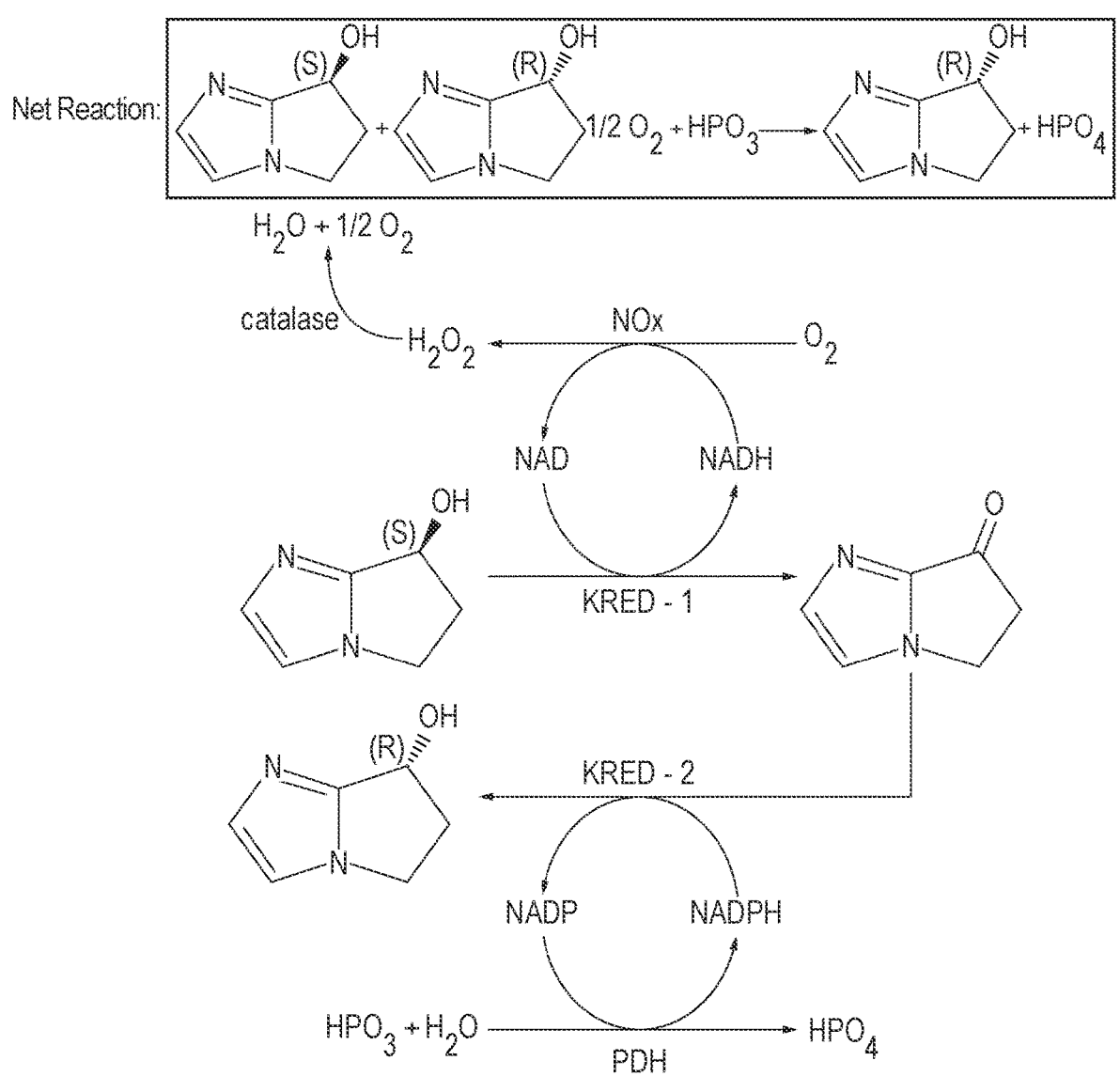
FIG. 3 provides the one-pot, multi-enzyme reaction scheme.
Figure 4:
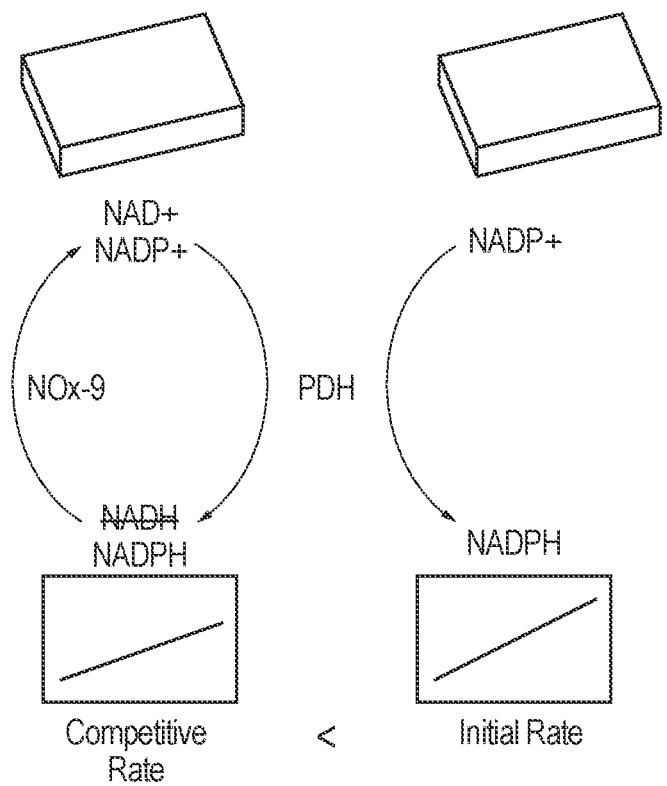
FIGS. 4 and 5 provide the cofactor competition assay schemes.
Figure 5:
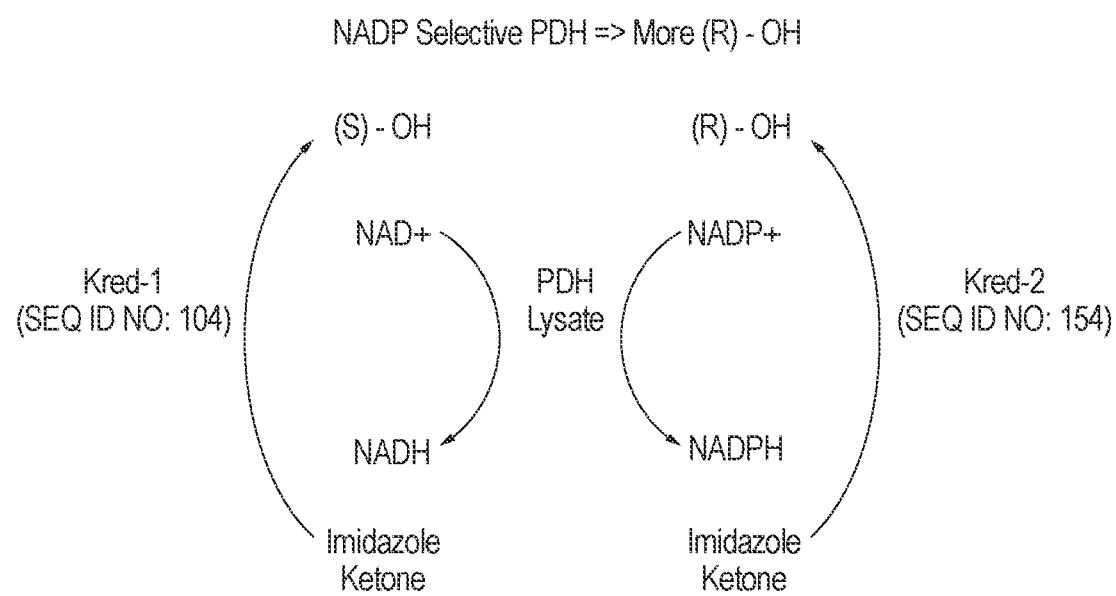
Figure 6:
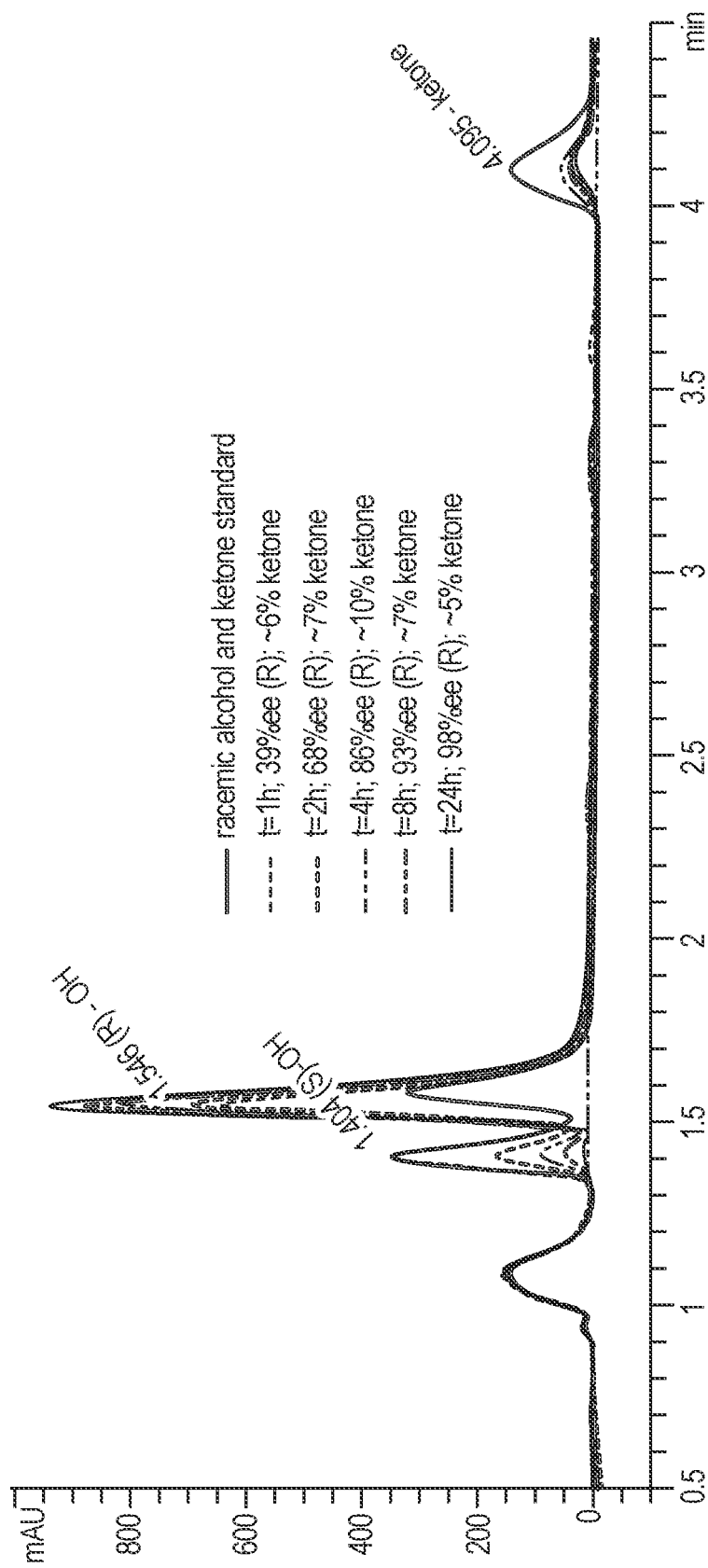
FIG. 6 provides the HPLC chromatogram of products obtained in one-pot, multi-enzyme reactions.

Ketoreductase and Phosphite Dehydrogenase Gene Construction and Expression Vectors The wild-type *Candida parapsilois* ketoreductase (KRED) encoding gene was amplified from genomic DNA and cloned into expression vector pCK11 0900 (See, FIG. 3 of US Pat. Appln. Publn. No. 2006/0195947, herein incorporated by reference) under the control of a lac promoter. The expression vector also contained the P15a origin of replication and the chloramphenicol resistance gene. The activity of the wild-type ketoreductase was confirmed as described in WO2008/042876. Polynucleotides encoding engineered ketoreductases of the present invention were likewise cloned into vector pCK11 0900 for expression in *E. coli* W311 0. Directed evolution of the KRED gene was carried out by first selecting the parent gene (i.e., SEQ ID NOS: 2, 6, 104) followed by library construction of variant genes in which positions associated with certain structural features were subjected to mutagenesis. These libraries were then plated, grown-up, and screened using HTP assays as described in Examples 2, 5 and 12.

The wild-type *Sporidiobolus salmonicolor* ketoreductase (KRED) encoding gene was synthesized for expression in *E. coli* based on the reported amino acid sequence of the ketoreductase and a codon optimization algorithm as described in Example 1 of W2008/042876, incorporated herein by reference. The gene was synthesized using oligonucleotides composed of 42 nucleotides and cloned into expression vector pCK11 0900 (See, FIG. 3 of US Pat. Appln. Pubn. No. 2006/0195947, herein incorporated by reference) under the control of a lac promoter. The expression vector also contained the P15a origin of replication and the chloramphenicol resistance gene. The activity of the wild-type ketoreductase was confirmed as described in W2008/042876. Polynucleotides encoding engineered ketoreductases of the present invention were likewise cloned into vector pCK11 0900 for expression in *E. coli* W311 0. Directed evolution of the KRED gene was carried out by first selecting the parent gene (i.e., SEQ ID NOS: 112, 124, 138) followed by library construction of variant genes in which positions associated with certain structural features were subjected to mutagenesis. These libraries were then plated, grown, and screened using HTP assays as described in Examples 3, 6, 7, 8 and 12.

A variant of the wild-type *Pseudomonas stutzeri* phosphite dehydrogenase (PDH) encoding gene was cloned into expression vector pCK11 0900 (See, FIG. 3 of US Pat. Appln. Pubn. No. 2006/0195947, herein incorporated by reference) under the control of a lac promoter. The expression vector also contained the P15a origin of replication and the chloramphenicol resistance gene. The activity of the phosphite dehydrogenase was confirmed as described in WO2008/042876.

Polynucleotides encoding engineered phosphite dehydrogenases of the present invention were likewise cloned into vector pCK11 0900 for expression in *E. coli* W311 0. Directed evolution of the PDH gene was carried out by first selecting the parent gene (i.e., SEQ ID NOS: 172, 182, 200, 208, 260) followed by library construction of variant genes in which positions associated with certain structural features were subjected to mutagenesis. These libraries were then plated, grown, and screened using HTP assays as described in Examples 4, and 9 through 12.

Example 2

Production and Analysis of Engineered KRED Polypeptides for Oxidation

Plasmid libraries obtained through directed evolution and containing evolved ketoreductase genes were transformed into *E. coli* W3110 and placed on Luria-Bertani (LB) agar medium containing 1% glucose and 30 µg/ml chloramphenicol (CAM). After incubation for at least 16 h at 30° C., colonies were picked using a Q-Bot® robotic colony picker (Genetix) into a 96-well shallow well microtiter plate containing 200 µL of LB, 1% glucose, and 30 µg/ml CAM. Cells were grown 18-20 h at 30° C., with shaking at 200 rpm. Twenty µL of this culture was then transferred to 360 µL of Terrific Broth (TB), 1 mM MgCl$_2$, 2 mM ZnSO$_4$ and 30 µg/ml CAM. After incubation of deep well plates at 30° C. with shaking at 250 rpm for 2.5 h (OD$_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 µL of 20 mM Tris, 2 mM ZnSO$_4$, 1 mM MgCl$_2$ pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 5 and 12.

Example 3

Production and Analysis of Engineered KRED Polypeptides for Reduction

Plasmid libraries obtained through directed evolution and containing evolved ketoreductase genes were transformed into *E. coli* W3110 and placed on Luria-Bertani (LB) agar medium containing 1% glucose and 30 μg/ml chloramphenicol (CAM). After incubation for at least 16 h at 30° C., colonies were picked using a Q-Bot® robotic colony picker (Genetix) into a 96-well shallow well microtiter plate containing 200 μL of LB, 1% glucose, and 30 μg/ml CAM. Cells were grown 18-20 h at 30° C., with shaking at 200 rpm. Twenty μL of this culture was then transferred to 360 μL of Terrific Broth (TB), 1 mM MgSO$_4$, and 30 μg/ml CAM. After incubation of deep well plates at 30° C. with shaking at 250 rpm for 2.5 h (OD$_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 μL of 20 mM Tris, 1 mM MgSO$_4$, pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 6 through 8, and Example 12.

Example 4

Production and Analysis of Engineered Phosphite Dehydrogenase Polypeptides

Plasmid libraries obtained through directed evolution and containing evolved phosphite dehydrogenase genes were transformed into *E. coli* W3110 and placed on Luria-Bertani (LB) agar medium containing 1% glucose and 30 μg/ml chloramphenicol (CAM). After incubation for at least 16 h at 30° C., colonies were picked using a Q-bot robotic colony picker (Genetix) into a 96-well shallow well microtiter plate containing 200 μL of LB, 1% glucose, and 30 μg/ml CAM. Cells were grown 18-20 h at 30° C., with shaking at 200 rpm. Twenty μL of this culture was then transferred to 360 μL of Terrific Broth (TB) and 30 μg/ml CAM. After incubation of deep well plates at 30° C. with shaking at 250 rpm for 2.5 h (OD$_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 μL of 20 mM Tris, pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 9 through 12.

Example 5

KRED Variants of SEQ ID NO:2

*E. coli* KRED variants were generated as described in Example 1. To analyze the activity of the variants, 20 μL of supernatant produced as described in Example 2 were added to a mixture of 180 μL racemic alcohol substrate (50 g/L), with 4 g/L NAD$^+$, 10 g/L commercially available NADH oxidase (NOx-9) and 100 mM FAD in 100 mM sodium phosphite pH 8.0. Reactions were incubated at 30° C. for 16-18 h, and quenched via addition of 200 μL of 1M HCl. The quenched mixture was added to the sample and briefly mixed. Reaction samples were analyzed by UPLC to quantify residual substrate and products as described above. Significantly improved variants are provided in Table 5.1, below

TABLE 5.1

Variants With Improved Activity Compared to SEQ ID NO: 2

| SEQ ID NO: | Amino Acid Substitutions (Relative to SEQ ID NO: 2) | Improvement |
|---|---|---|
| 4 | R309F | +++ |
| 6 | C57L | +++ |
| 8 | G114K | +++ |
| 10 | G272V | +++ |
| 12 | G263Y | +++ |
| 14 | L276F | +++ |
| 16 | C57I | +++ |
| 18 | G272P | +++ |
| 20 | G272L | +++ |
| 22 | G114M | ++ |
| 24 | G272S | +++ |
| 26 | G272Q | +++ |
| 28 | G272H | +++ |
| 30 | G272T | +++ |
| 32 | G114H | +++ |
| 34 | G272I | +++ |
| 36 | C57X/W286X | +++ |
| 38 | G272W | ++ |
| 40 | I279H | ++ |
| 42 | G263H | +++ |
| 44 | H45R | +++ |
| 46 | S268M | ++ |
| 48 | S268W | ++ |
| 50 | L274V | ++ |
| 52 | V83I | ++ |
| 54 | Y52D | ++ |
| 56 | I279R | +++ |
| 58 | Y52S | +++ |
| 60 | I279Q | ++ |
| 62 | L274I | ++ |
| 64 | D56L | +++ |
| 66 | K110T | + |
| 68 | P228S | ++ |
| 70 | S138V/A146S/M258V/T289S | + |
| 72 | K211R | + |
| 74 | K37R | + |
| 76 | K37R/K211R/G229R | ++ |
| 78 | K211R/G229R | + |
| 80 | G229R | ++ |
| 82 | K37R/G229R | + |
| 84 | K37R/K211R | ++ |
| 86 | L276M | +++ |
| 88 | I79T/V83S/A275N/L276M | +++ |
| 90 | V83S/A275N/L276M | ++ |
| 92 | V83S/L276M | ++ |
| 94 | A275N/L276M | +++ |
| 96 | L55F/C57A/L276M | + |
| 98 | A104G | ++ |
| 100 | C57I/A104G/G114H | ++++ |
| 102 | C57L/A104G/G114H/G229R | ++++ |
| 104 | Y52S/C57L/G272H/I279H/L296F | ++++ |
| 106 | Y52D/C57L/G272H | ++++ |
| 108 | Y52S/C57L/G272H/L274V/I279H/L296F | ++++ |
| 110 | Y52S/C57L/K110T/G272H/L296F | ++++ |

| Key for Table 5.1 | |
|---|---|
| ++++ | >6 |
| +++ | >4 and <6 |

-continued

| Key for Table 5.1 | |
|---|---|
| ++ | >2.5 and <4 |
| + | >1.2 and <2.5 |

Example 6

KRED Variants of SEQ ID NO:112

*E. coli* KRED variants were generated as described in Example 1. To analyze the activity of the variants, 5 μL supernatant produced as described in Example 3 were added to 95 μL of 0.3 M phosphite buffer pH 7.9 containing 0.25 mM NADPH; 19 g/L ketone substrate and 5 g/L PDH. Reactions were incubated at room temperature for 16-18 hours with gentle shaking. Reactions were quenched via addition of 100 μL of 1M HCl. The quenched mixture (10 μL) was diluted into 190 μL of water. Reaction samples (10 μL) were analyzed by HPLC to quantify residual substrates and products as described above. Significantly improved variants are provided in Table 6.1, below.

TABLE 6.1

Variants With Improved Activity and Selectivity Compared to SEQ ID NO: 112

| SEQ ID NO: | Amino Acid Substitutions (Relative to SEQ ID NO: 112) | Activity Improvement | Selectivity Improvement |
|---|---|---|---|
| 114 | V24I/S220G/P314R/S315A | + | n.d. |
| 116 | V24I/T106P/S136A/S220G/L258V/C260A/P314R/S315A | + | n.d. |
| 118 | V24I/T106P/F214L/A250V/L258V/C260A/P314R/S315A | + | n.d. |
| 120 | T122I/I159V/L316E/I318L | ++ | n.d. |
| 122 | I159V/V251Q/Y272F/T277P/L316E/I318L/I330L | + | + |
| 124 | N207G | +++ | +++ |
| 126 | N207G | +++ | +++ |
| 128 | V135F | ++ | ++ |
| 130 | V135F | ++ | ++ |
| 132 | I139V/N207S | +++ | +++ |

| Key for Table 6.1 | | |
|---|---|---|
| | Activity | Selectivity |
| +++ | >4 | >5 |
| ++ | >2.5 and <4 | >2 and <5 |
| + | >1.5 and <2.5 | >1 and <2 |

Example 7

KRED Variants of SEQ ID NO:124

*E. coli* KRED variants were generated as described in Example 1. To analyze the activity of the variants, 7.5 μL supernatant produced as described in Example 3 were added to 192.5 μL of 0.3 M phosphite buffer pH 7.9 containing 0.25 mM NADPH; 50 g/L ketone substrate and 5 g/L PDH. Reactions were incubated at room temperature for 16-18 hours with gentle shaking. Reactions were quenched via addition of 100 μL of 1M HCl. The quenched mixture (10 μL) was diluted into 190 μL of water. Reaction samples (10 μL) were analyzed by HPLC to quantify residual substrates and products as described above. Significantly improved variants are provided in Table 7.1, below.

TABLE 7.1

Variants With Improved Activity Compared to SEQ ID NO: 124

| SEQ ID NO: | Amino Acid Substitutions (Relative to SEQ ID NO: 124) | Activity Improvement |
|---|---|---|
| 134 | V95T | +++ |
| 136 | V24I/V95T/M228T | +++ |
| 138 | V95T/V135F/I139V/G207N | ++++ |
| 140 | K3Y/V95T | +++ |
| 142 | K3Y/V95T/M228T/P314R | +++ |
| 144 | A2T/Y101P/A179L/T182M/M228R/A238L/T282E | ++ |
| 146 | I159V/M228L/K309Q/I330L | + |

| Key for Table 7.1 | |
|---|---|
| ++++ | >4 |
| +++ | >3 and <4 |
| ++ | >2 and <3 |
| + | >1.5 and <2 |

Example 8

KRED Variants of SEQ ID NO:138

*E. coli* KRED variants were generated as described in Example 1. To analyze the co-factor preference of the variants, four separate assays were utilized. First, 10 μL supernatant produced as described in Example 3 were added to 90 μL of 0.2 M phosphite buffer pH 7.9 containing 1 g/L ketone and 1 g/L of NADPH. The initial rate of NADPH consumption of the samples was analyzed via fluorescence with Ex λ=330 nm Em λ=445 nm, acquired for 180 seconds every 21 seconds.

Second, 20 μL supernatant produced as described in Example 3 were added to 190 μL of 0.2 M phosphite buffer pH 7.9 containing 1 g/L racemic alcohol and 2 g/L of NAD⁺. The initial rate of NAD⁺ consumption was analyzed via kinetic readings at UV 340 nm, data were acquired every 9 seconds for 5 minutes.

Third, 20 μL supernatant produced as described in Example 3 were added to 180 μL of 500 mM sodium phosphite containing 2 g/L imidazole ketone and 16.4 mM of NADPH; the samples were incubated at room temperature for 2 hr, shaking at 300 rpm. Reactions were quenched via addition of 200 μL of MeCN. After shaking for 5 minutes, 100 μL of the quenched reaction was transferred to a Millipore filter plate (45 micron pore size) with a co-star round bottom plate containing 100 μL of water to collect the filtrate and the mixture was spun at 4000 rpm for 2 minutes. Reaction samples (10 μL) were analyzed by HPLC to quantify residual substrate and product as described above.

Fourth, 20 μL supernatant produced as described in Example 3 were added to 180 μL of 500 mM sodium phosphite containing 2 g/L imidazole ketone and 16.4 mM of NADPH; the samples were incubated at room temperature for 2 hr, shaking at 300 rpm. Reactions were quenched via addition of 200 μL of MeCN. After shaking for 5 minutes, 100 μL of the quenched reaction was transferred to a Millipore filter plate (45 micron pore size) with a co-star round bottom plate containing 100 μL of water to collect the filtrate and the mixture was spun at 4000 rpm for 2 minutes.

Reaction samples (10 μL) were analyzed by HPLC to quantify residual substrate and product as described above. Co-factor specificity was calculated as (amount of product generated with NADPH)/
(amount of product generated with NADH)

Significantly improved variants are provided in Table 8.1, below.

TABLE 8.1

Variants With Improved Activity and Co-factor Specificity Compared to SEQ ID NO: 138

| SEQ ID NO: | Amino Acid Substitutions (Relative to SEQ ID NO: 138) | Activity Improvement | Co-factor Specificity Improvement |
|---|---|---|---|
| 148 | V24I/A43V/S47E/L49N/A67V/V68E/E70P/I91V/S220G | + | + |
| 150 | V24I/V68E/I91V/T218N/S220G | + | ++ |
| 152 | Y78F/P107G | + | ++ |
| 154 | K74A/Q75E/Y78F/A108V | ++ | +++ |
| 156 | Q75E/Y78F/N99P/A108V/D215S/S224A | ++ | +++ |
| 158 | G19S | +++ | ++ |
| 160 | T95C | +++ | + |
| 162 | S96G | +++ | + |
| 164 | G19S | +++ | + |
| 166 | M72Q | +++ | ++ |
| 168 | A67W | + | ++ |
| 170 | N114V | + | ++ |

Key for Table 8.1

| | Activity Improvement | Co-factor Specificity Improvement |
|---|---|---|
| +++ | >4 | >3 |
| ++ | >2 and <4 | >2 and <3 |
| + | >1 and <2 | >1 and <2 |

Example 9

PDH Variants of SEQ ID NO: 172

*E. coli* PDH variants were generated as described in Example 1. To analyze the activity of the variants, 5 μL supernatant produced as described in Example 3 were added to 95 μL of 0.5 M sodium phosphite buffer pH 7.9 containing 0.25 mM NADPH; 50 g/L ketone substrate and 2 g/L KRED of SEQ ID NO: 138. Reactions were incubated at 25° C. for 16-18 hours with gentle shaking. Reactions were quenched via addition of 100 μL of 1M HCL. The quenched mixture (10 μL) was diluted into 190NL of water. Reaction samples (10 NL) were analyzed by HPLC to quantify residual substrates and products as described above. Significantly improved variants are provided in Table 9.1, below.

TABLE 9.1

Variants With Improved Activity Compared to SEQ ID NO: 172

| SEQ ID NO: | Amino Acid Substitutions (Relative to SEQ ID NO: 172) | Activity Improvement |
|---|---|---|
| 174 | R10K/C73A/R137Q | + |
| 176 | R10K/C73A/F78Y/V233I/N323D | + |
| 178 | R137Q/V233I/E303A/N323D | + |
| 180 | R10K/C73A/F78Y/R137Q/N323D/V325A | + |
| 182 | R44A/R132Q/N145G | + |

TABLE 9.1-continued

Variants With Improved Activity Compared to SEQ ID NO: 172

| SEQ ID NO: | Amino Acid Substitutions (Relative to SEQ ID NO: 172) | Activity Improvement |
|---|---|---|
| 184 | E13D/R41A/Q63A/R132Q/A193S/S195E | + |
| 186 | R41A/R44A/A88R/A193S/S195E | + |
| 188 | E266V | + |
| 190 | E266W | + |
| 192 | E266S | + |
| 194 | R44A/R132Q/P136D/R137Q/N145G/I293L | ++ |
| 196 | R44A/R132Q/R137I/N145G/V233I/A308V/N323D | ++ |
| 198 | R44A/R132Q/Q135A/P136D/R137I/N145G/I293L | ++ |
| 200 | R44A/R132Q/R137I/N145G/I293L/N323D | ++ |
| 202 | R44A/R132Q/N145G/S195E/I293L/N323D | ++ |
| 204 | R44A/V113S/R132Q/N145G | ++ |
| 206 | L18M/R44A/L119F/A124E/R132Q/R137I/N145G/I293L/N323D/A334K/C336R | +++ |
| 208 | R44A/L119F/R132Q/R137I/N145G/L158K/A175S/K177T/I293L/A317R/N323D | +++ |
| 210 | L18M/R44A/L119F/A124E/R132Q/R137I/N145G/L158K/K177T/I293L/N323D | +++ |
| 212 | L18M/R44A/L119F/A124E/R132Q/R137I/N145G/L158K/A175S/K177T/I293L/A317R/N323D | +++ |
| 214 | R44A/R69K/R120V/R132Q/R137I/N145G/A175T/S195E/I293L/N323D | +++ |
| 216 | S32V/R44A/R132Q/R137I/N145G/R186T/V233I/I293L/N323D/C336S | +++ |

Key for Table 9.1

| +++ | >4 |
| --- | --- |
| ++ | >2 and <4 |
| + | >1 and <2 |

Example 10

PDH Variants of SEQ ID NO:208

*E. coli* PDH variants were generated as described in Example 1. To analyze the co-factor preference of the variants, supernatant produced as described in Example 3 was diluted 4-fold with 50 mM Tris-HCl buffer, pH 7.5. Twenty μL of the diluted lysate was added to 180 μL of 0.1 M sodium phosphite buffer pH 7.9 and incubated overnight to consume residual NAD and NADP present in the lysate. The variants were then screened in three separate assays to analyze their co-factor specificity. First, for the initial rate NADP assay, 0.2 mM NADP in 0.1 M sodium phosphite buffer pH 7.9 was added and initial rate measured via fluorescence assay over 2 minutes. Second, for initial rate NAD assay, 0.2 mM NAD+ in 0.1M sodium phosphite buffer pH 7.9 was added and initial rate measured via fluorescence assay over 2 minutes. Third, a co-factor competition assay was performed. For this assay, 100 mM phosphite pH 7.9 containing 100 uM NADP, 1 mM NAD and 1 g/L NADH oxidase NOx-9 was added to the reaction. NOx-9 consumes all NADH immediately, leaving only NADPH signal, reduced by competition between NADP and NAD+. Reactions were quenched via addition of 100 μL of 1M HCl. The quenched mixture (10 μL) was diluted into 190 μL of water. Diluted reaction samples (10 μL) were analyzed by HPLC to quantify residual substrates and products as described above. Significantly improved variants are provided in Table 10.1, below.

TABLE 10.1

Variants With Improved Co-factor Specificity Compared to SEQ ID NO: 208

| SEQ ID NO: | Amino Acid Substitutions (Relative to SEQ ID NO: 208) | NADP+ Initial Rate Improvement | Cofactor Specificity Improvement |
|---|---|---|---|
| 218 | F78Y/F150I/F198L/R327S/L328P | + | + |
| 220 | N211A/D213Q/I322Q | + | + |
| 222 | A178P/C194L/N211A/D213Q/I322Q | + | + |
| 224 | F95I/N211A/D213Q/I322M | + | + |
| 226 | S32V/A59M/A124E/T177S/Q191H/R327D | + | + |
| 228 | L215P | + | + |
| 230 | L206N | + | + |
| 232 | T104F | ++ | + |
| 234 | T104L | ++ | + |
| 236 | E266S | + | + |
| 238 | V262P | + | + |
| 240 | V262D | + | + |
| 242 | V83A/E266A | + | + |
| 244 | D323N | + | + |

| Key for Table 10.1 | |
|---|---|
| ++ | >2 |
| + | >1 and <2 |

Example 11

Additional PDH Variants of SEQ ID NO:208

*E. coli* PDH variants were generated as described in Example 1. To analyze the co-factor preference of the variants, supernatant produced as described in Example 3 was diluted 4-fold with 50 mM Tris-HCl buffer, pH 7.5. Twenty μL of the diluted lysate was added to 180 μL of 0.1 M sodium phosphite buffer pH 7.9 and incubated overnight to consume residual NAD and NADP present in the lysate. The variants were then screened in three separate assays to analyze their co-factor specificity. First, for the initial rate NADP assay 0.2 mM NADP in 0.1 M sodium phosphite buffer pH 7.9 was added and initial rate measured via fluorescence assay over 2 minutes. Second, for initial rate NAD assay, 0.2 mM NAD+ in 0.1M sodium phosphite buffer pH 7.9 was added and initial rate measured via fluorescence assay over 2 minutes. Third, a co-factor competition assay was performed. For this assay, three μL of pre-incubated lysate was added to 97 μL of 200 mM phosphite pH 7.9 containing 2 mM NAD, 0.2 mM NADP, 2 g/L KRED of SEQ ID NO:138, 4 g/L KRED of SEQ ID NO:104 and 10 g/L ketone (2). Reactions were quenched via addition of 100 μL of 1M HCl. The quenched mixture (10 μL) was diluted into 190 μL of water. Diluted reaction samples (10 μL) were analyzed by reverse phase HPLC to quantify residual substrate and both enantiomers of the product as described above. Significantly improved variants are provided in Table 11.1, below.

| SEQ ID NO: | Amino Acid Substitutions (Relative to SEQ ID NO: 208) | Cofactor Specificity Improvement |
|---|---|---|
| 246 | V83A/T104L/L206N | +++ |
| 248 | A74T/V83A/L206N | ++ |
| 250 | T104L/V262L | +++ |
| 252 | T104L/L206N | +++ |
| 254 | S295R | +++ |
| 256 | V96G | +++ |
| 258 | T104M | + |

| Key for Table 11.1 | |
|---|---|
| +++ | >8 |
| ++ | >4 and <8 |
| + | >2 and <4 |

Example 12

Production of Engineered Polypeptides and Performance Validation

Plasmids comprising variants obtained through directed evolution of the KRED of SEQ ID NO:2 and containing evolved ketoreductase genes were transformed into *E. coli* W3110 and placed on Luria-Bertani (LB) agar medium containing 1% glucose and 30 g/ml chloramphenicol (CAM). After incubation for at least 16 h at 30° C., a single colony was picked into 5 mL of LB, 1% glucose, and 30 μg/ml CAM. Cells were grown 18-20 h at 30° C., with shaking at 250 rpm. This culture was then transferred into Terrific Broth (TB), 2 mM ZnSO$_4$, 1 mM MgSO$_4$, and 30 g/ml CAM at a final OD$_{600}$ of ~0.02 and a final volume of 250 mL. After incubation of the flasks at 30° C. with shaking at 250 rpm for 3.5 h (OD$_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed in 50 mL ice cold 50 mM sodium phosphate pH 7.5 containing 2 mM ZnSO$_4$ and 1 mM MgSO$_4$, resuspended in 30 ml of the same buffer, and lysed using a cell disruptor at 18-20 kpsi. Lysates were clarified at 10000×g for 60 min, and clarified supernatants were lyophilized to an off white powder.

Plasmids of comprising variants obtained through directed evolution of the KRED of SEQ ID NOS:112 and 138, and containing evolved ketoreductase genes were transformed into *E. coli* W3110 and placed on Luria-Bertani (LB) agar medium containing 1% glucose and 30 μg/ml chloramphenicol (CAM). After incubation for at least 16 h at 30° C., a single colony was picked into 5 mL of LB, 1% glucose, and 30 μg/ml CAM. Cells were grown 18-20 h at 30° C., with shaking at 250 rpm. This culture was then transferred into Terrific Broth (TB), and 30 g/ml CAM at a final OD$_{600}$ of ~0.02 and a final volume of 250 mL. After incubation of the flasks at 30° C. with shaking at 250 rpm for 3.5 h (OD$_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed in 50 mL ice cold 50 mM sodium phosphate pH 7.5, resuspended in 30 ml of the same buffer, and lysed using a cell disruptor at 18-20 kpsi. Lysates were clarified at 10000×g for 60 min, and clarified supernatants were lyophilized to an off white powder.

Plasmids comprising variants obtained through directed evolution of the PDH of SEQ ID NOS:172 and 208, and containing evolved phosphite dehydrogenase genes were transformed into E. coli W3110 and placed on Luria-Bertani (LB) agar medium containing 1% glucose and 30 g/ml chloramphenicol (CAM). After incubation for at least 16 h at 30° C., a single colony was picked into 5 mL of LB, 1% glucose, and 30 μg/ml CAM. Cells were grown 18-20 h at 30° C., with shaking at 250 rpm. This culture was then transferred into Terrific Broth (TB), and 30 μg/ml CAM at a final $OD_{600}$ of ~0.02 and a final volume of 250 mL. After incubation of the flasks at 30° C. with shaking at 250 rpm for 3.5 h ($OD_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed in 50 mL ice cold 50 mM sodium phosphate pH 7.5, resuspended in 30 ml of the same buffer, and lysed using a cell disruptor at 18-20 kpsi. Lysates were clarified at 10000×g for 60 min, and clarified supernatants were lyophilized to an off white powder.

To evaluate the final compound under process like conditions, 50 g/L of racemic alcohol substrate in 500 mM sodium phosphite buffer pH 7.9, 0.1 g/L NAD, 0.1 g/L NADP, 2.5 g/L KRED of SEQ ID NO:104, 10 g/L commercially available NADH oxidase NOx-9, 2.5 g/L KRED of SEQ ID:154, 10 g/L PDH of SEQ ID NO:250 was stirred under stream of oxygen with 1% v/v antifoam at room temperature for 24 hours resulting in 93% conversion of substrate and 99.5% enantiomeric excess of (R)-alcohol 1a. Reaction samples were analyzed by reverse phase HPLC to quantify residual substrate and products as described above.

While various specific embodiments have been illustrated and described, it will be appreciated that various changes can be made without departing from the spirit and scope of the invention(s).

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. An engineered ketoreductase variant having at least 95% sequence identity to SEQ ID NO: 2, wherein said engineered ketoreductase variant comprises a substitution in the amino acid sequence at position 57, as compared to SEQ ID NO: 2.

2. The engineered ketoreductase variant of claim 1 having at least 95% sequence identity to SEQ ID NO:2, and further comprising at least one substitution or substitution set at one or more positions selected from positions 37, 37/211, 37/211/229, 37/229, 45, 52, 52/110/272/296, 52/272, 52/272/274/279/296, 52/272/279/296, 55/276, 56, 104/114, 104/114/229, 286, 79/83/275/276, 83, 83/275/276, 83/276, 104, 110, 114, 138/146/258/289, 211, 211/229, 228, 229, 263, 268, 272, 274, 275/276, 276, 279, and 309, wherein said positions are numbered with reference to SEQ ID NO:2.

3. The engineered ketoreductase variant of claim 1, comprising a polypeptide sequence having at least 97% sequence identity to SEQ ID NO: 2.

4. The engineered ketoreductase variant of claim 1, comprising a polypeptide sequence having at least 99% sequence identity to SEQ ID NO: 2.

5. The engineered ketoreductase variant of claim 1, wherein said engineered ketoreductase comprises a polypeptide sequence selected from the even-numbered sequences set forth in SEQ ID NOS: 6, 16, 36, 96, 100-110.

6. A composition comprising at least one engineered ketoreductase variant provided in claim 1.

* * * * *